US012697180B2

(12) United States Patent
Boyer et al.

(10) Patent No.: US 12,697,180 B2
(45) Date of Patent: Aug. 4, 2026

(54) INTERLOCKING COLLET SYSTEM FOR A SURGICAL DEVICE

(71) Applicant: MAKO Surgical Corp., Weston, FL (US)

(72) Inventors: Jonathan P. Boyer, Galesburg, MI (US); James E. Flatt, Kalamazoo, MI (US)

(*) Notice: Subject to any disclaimer, the term of this patent is extended or adjusted under 35 U.S.C. 154(b) by 803 days.

(21) Appl. No.: 17/484,903

(22) Filed: Sep. 24, 2021

(65) Prior Publication Data

US 2022/0087754 A1 Mar. 24, 2022

Related U.S. Application Data

(60) Provisional application No. 63/082,514, filed on Sep. 24, 2020.

(51) Int. Cl.
*A61B 34/30* (2016.01)
*A61B 17/00* (2006.01)
(Continued)

(52) U.S. Cl.
CPC .............. *A61B 34/30* (2016.02); *A61B 34/20* (2016.02); *A61B 34/70* (2016.02); *A61B 90/03* (2016.02);
(Continued)

(58) Field of Classification Search
CPC ......... A61B 34/30; A61B 34/20; A61B 34/70; A61B 90/03; A61B 2017/00477;
(Continued)

(56) References Cited

U.S. PATENT DOCUMENTS 2,143,010 A 1/1939 Imblum
2,679,101 A 5/1954 Steuer et al.
(Continued)

FOREIGN PATENT DOCUMENTS

EP 0070516 A2 1/1983
EP 0070516 A3 4/1985
(Continued)

OTHER PUBLICATIONS

English language abstract and machine-assisted English translation for EP 1 264 653 A2 extracted from espacenet.com database on Oct. 6, 2021, 25 pages.
(Continued)

*Primary Examiner* — Kathleen S Holwerda
*Assistant Examiner* — James R McGinnity
(74) *Attorney, Agent, or Firm* — Howard & Howard Attorneys PLLC

(57) ABSTRACT

An interlocking collet system includes an attachment comprising first and second attachment surfaces spaced from one another and a collet. The collet comprises a housing configured to extend along an axis. The housing defines a bore for selectively disposing and retaining the attachment therein in an installed position. First and second locking members are disposed within the bore and are moveable. At least one bias member is disposed within the bore and is arranged to position the first locking member in a first position in which the first locking member is configured to contact the first attachment surface. The at least one bias member is arranged to position the second locking member in a second position in which the second locking member is configured to contact the second attachment surface. The first and second locking members are configured to exert opposing axial forces on the attachment.

25 Claims, 23 Drawing Sheets

(51) Int. Cl.

| | |
|---|---|
| *A61B 34/00* | (2016.01) |
| *A61B 34/20* | (2016.01) |
| *A61B 90/00* | (2016.01) |

(52) U.S. Cl.
CPC .... *A61B 90/37* (2016.02); *A61B 2017/00477* (2013.01); *A61B 2034/2048* (2016.02); *A61B 2090/034* (2016.02)

(58) Field of Classification Search
CPC ...... A61B 2034/2048; A61B 2090/034; A61B 34/31–37
See application file for complete search history.

(56) References Cited

U.S. PATENT DOCUMENTS

| | | | |
|---|---|---|---|
| 3,070,380 A | 12/1962 | Holmberg |
| 3,400,459 A | 9/1968 | Stemler |
| 3,475,817 A | 11/1969 | Loge |
| 3,791,660 A | 2/1974 | Bostley |
| 3,835,858 A | 9/1974 | Hagen |
| 3,847,154 A | 11/1974 | Nordin |
| 3,867,943 A | 2/1975 | Nordin |
| 3,905,609 A | 9/1975 | Sussman |
| 4,030,617 A | 6/1977 | Richter |
| 4,071,029 A | 1/1978 | Richmond et al. |
| 4,283,764 A | 8/1981 | Crum et al. |
| 4,298,308 A | 11/1981 | Richter |
| 4,517,977 A | 5/1985 | Frost |
| 4,589,810 A | 5/1986 | Heindl et al. |
| 4,648,783 A | 3/1987 | Tan et al. |
| 4,692,073 A | 9/1987 | Martindell |
| 4,708,548 A | 11/1987 | Taylor et al. |
| 4,804,301 A | 2/1989 | Hunt |
| 4,867,618 A | 9/1989 | Brohammer |
| 4,895,146 A | 1/1990 | Draenert |
| 4,922,069 A | 5/1990 | Huizenga |
| 4,944,642 A | 7/1990 | Andersson |
| 4,975,056 A | 12/1990 | Eibofner |
| 5,013,194 A | 5/1991 | Wienhold |
| 5,022,857 A | 6/1991 | Matsutani et al. |
| 5,040,979 A | 8/1991 | Kuhn |
| 5,055,044 A | 10/1991 | Kuhn |
| 5,096,421 A | 3/1992 | Seney |
| 5,212,433 A | 5/1993 | Yasuyuki |
| 5,343,961 A | 9/1994 | Ichikawa |
| 5,363,474 A | 11/1994 | Sarugaku et al. |
| 5,458,445 A | 10/1995 | Bader et al. |
| 5,490,683 A | 2/1996 | Mickel et al. |
| 5,490,860 A | 2/1996 | Middle |
| 5,595,273 A | 1/1997 | Endoy et al. |
| 5,649,956 A | 7/1997 | Jensen et al. |
| 5,665,945 A | 9/1997 | Oshima |
| 5,682,886 A | 11/1997 | Delp et al. |
| 5,741,084 A | 4/1998 | Del Rio et al. |
| 5,741,263 A | 4/1998 | Umber et al. |
| 5,748,854 A | 5/1998 | Watanabe et al. |
| 5,762,458 A | 6/1998 | Wang et al. |
| 5,783,922 A | 7/1998 | Hashimoto et al. |
| 5,807,378 A | 9/1998 | Jensen et al. |
| 5,814,038 A | 9/1998 | Jensen et al. |
| 5,816,803 A | 10/1998 | Nakanishi |
| 5,855,583 A | 1/1999 | Wang et al. |
| 5,915,673 A | 6/1999 | Kazerooni |
| 6,007,550 A | 12/1999 | Wang et al. |
| 6,012,922 A | 1/2000 | Novak |
| 6,033,415 A | 3/2000 | Mittelstadt et al. |
| 6,045,564 A | 4/2000 | Walen |
| 6,062,575 A | 5/2000 | Mickel et al. |
| 6,063,095 A | 5/2000 | Wang et al. |
| 6,080,181 A | 6/2000 | Jensen et al. |
| 6,102,850 A | 8/2000 | Wang et al. |
| 6,132,448 A | 10/2000 | Perez et al. |
| 6,151,789 A | 11/2000 | Raab et al. |
| 6,160,324 A | 12/2000 | Terada et al. |
| 6,212,443 B1 | 4/2001 | Nagata et al. |
| 6,222,338 B1 | 4/2001 | Villaret |
| 6,238,152 B1 | 5/2001 | Fujimoto et al. |
| 6,325,808 B1 | 12/2001 | Bernard et al. |
| 6,331,181 B1 | 12/2001 | Tierney et al. |
| 6,352,532 B1 | 3/2002 | Kramer et al. |
| 6,385,508 B1 | 5/2002 | McGee et al. |
| 6,386,513 B1 | 5/2002 | Kazerooni |
| 6,396,232 B2 | 5/2002 | Haanpaa et al. |
| 6,413,264 B1 | 7/2002 | Jensen et al. |
| 6,436,107 B1 | 8/2002 | Wang et al. |
| 6,438,455 B2 | 8/2002 | Matsumoto |
| 6,491,701 B2 | 12/2002 | Tierney et al. |
| 6,494,892 B1 | 12/2002 | Ireland et al. |
| 6,562,055 B2 | 5/2003 | Walen |
| 6,587,750 B2 | 7/2003 | Gerbi et al. |
| 6,620,174 B2 | 9/2003 | Jensen et al. |
| 6,699,177 B1 | 3/2004 | Wang et al. |
| 6,733,218 B2 | 5/2004 | Del Rio et al. |
| 6,780,189 B2 | 8/2004 | Tidwell et al. |
| 6,821,120 B2 | 11/2004 | Suzuki et al. |
| 6,866,671 B2 | 3/2005 | Tierney et al. |
| 6,994,703 B2 | 2/2006 | Wang et al. |
| 7,001,391 B2 | 2/2006 | Estes et al. |
| 7,011,661 B2 | 3/2006 | Riedel et al. |
| 7,025,064 B2 | 4/2006 | Wang et al. |
| 7,025,761 B2 | 4/2006 | Wang et al. |
| 7,048,745 B2 | 5/2006 | Tierney et al. |
| 7,074,179 B2 | 7/2006 | Wang et al. |
| 7,090,448 B2 | 8/2006 | Stoll et al. |
| 7,118,582 B1 | 10/2006 | Wang et al. |
| 7,125,403 B2 | 10/2006 | Julian et al. |
| 7,176,399 B2 | 2/2007 | Graiger et al. |
| 7,249,602 B1 | 7/2007 | Emanuel |
| 7,331,967 B2 | 2/2008 | Lee et al. |
| 7,379,790 B2 | 5/2008 | Toth et al. |
| 7,524,320 B2 | 4/2009 | Tierney et al. |
| 7,549,992 B2 | 6/2009 | Shores et al. |
| 7,559,927 B2 | 7/2009 | Shores et al. |
| 7,658,740 B2 | 2/2010 | Shores et al. |
| 7,695,481 B2 | 4/2010 | Wang et al. |
| 7,747,311 B2 | 6/2010 | Quaid, III |
| 7,783,384 B2 | 8/2010 | Kraft |
| 7,865,266 B2 | 1/2011 | Moll et al. |
| 7,879,037 B2 | 2/2011 | Brunnett et al. |
| 7,947,050 B2 | 5/2011 | Lee et al. |
| 7,947,051 B2 | 5/2011 | Lee et al. |
| 7,953,509 B2 | 5/2011 | Murayama |
| 7,955,322 B2 | 6/2011 | Devengenzo et al. |
| 7,963,913 B2 | 6/2011 | Devengenzo et al. |
| 8,010,180 B2 | 8/2011 | Quaid et al. |
| 8,010,234 B2 | 8/2011 | Henne |
| 8,095,200 B2 | 1/2012 | Quaid, III |
| 8,123,740 B2 | 2/2012 | Madhani et al. |
| 8,142,447 B2 | 3/2012 | Cooper et al. |
| 8,170,717 B2 | 5/2012 | Sutherland et al. |
| 8,182,470 B2 | 5/2012 | Devengenzo et al. |
| 8,201,341 B2 | 6/2012 | Ferrari |
| 8,211,116 B2 | 7/2012 | Oostman, Jr. et al. |
| 8,226,072 B2 | 7/2012 | Murayama |
| 8,226,664 B2 | 7/2012 | Drews et al. |
| 8,277,474 B2 | 10/2012 | Norman et al. |
| 8,287,522 B2 | 10/2012 | Moses et al. |
| 8,288,670 B2 | 10/2012 | Nguyen |
| 8,333,588 B2 | 12/2012 | Putz et al. |
| 8,597,316 B2 | 12/2013 | McCombs |
| 8,690,876 B2 | 4/2014 | del Rio et al. |
| 8,794,100 B2 | 8/2014 | Isobe et al. |
| 8,800,939 B2 | 8/2014 | Karsak et al. |
| 8,801,713 B2 | 8/2014 | del Rio et al. |
| 9,008,757 B2 | 4/2015 | Wu |
| 9,119,655 B2 | 9/2015 | Bowling et al. |
| 9,120,222 B2 | 9/2015 | Grygorowicz et al. |
| 9,180,527 B2 | 11/2015 | Haimer |
| 9,456,864 B2 | 10/2016 | Witt et al. |
| 9,566,121 B2 | 2/2017 | Staunton et al. |
| 9,676,096 B2 | 6/2017 | Roberts et al. |
| 9,937,058 B2 | 4/2018 | Axelson, Jr. et al. |
| 10,456,207 B2 | 10/2019 | Flatt |

(56) References Cited

U.S. PATENT DOCUMENTS

| | | | |
|---|---|---|---|
| 10,675,050 | B2 | 6/2020 | Staunton et al. |
| 2002/0165549 | A1 | 11/2002 | Owusu-Akyaw et al. |
| 2003/0181934 | A1 | 9/2003 | Johnston et al. |
| 2004/0161723 | A1 | 8/2004 | Helfenbein |
| 2004/0236352 | A1 | 11/2004 | Wang et al. |
| 2005/0011740 | A1 | 1/2005 | Graiger et al. |
| 2005/0149003 | A1 | 7/2005 | Tierney et al. |
| 2005/0151902 | A1 | 7/2005 | Wang et al. |
| 2005/0222714 | A1 | 10/2005 | Nihei et al. |
| 2005/0228365 | A1 | 10/2005 | Wang et al. |
| 2005/0234433 | A1 | 10/2005 | Wang et al. |
| 2005/0277869 | A1 | 12/2005 | Boukhny |
| 2006/0011457 | A1 | 1/2006 | Robertson |
| 2006/0053974 | A1 | 3/2006 | Blust et al. |
| 2006/0178775 | A1 | 8/2006 | Zhang et al. |
| 2007/0012135 | A1 | 1/2007 | Tierney et al. |
| 2007/0021766 | A1 | 1/2007 | Belagali et al. |
| 2007/0265653 | A1 | 11/2007 | Suzuki |
| 2008/0167652 | A1 | 7/2008 | Reinhard |
| 2008/0208195 | A1 | 8/2008 | Shores et al. |
| 2008/0211634 | A1 | 9/2008 | Hopkins et al. |
| 2008/0228196 | A1 | 9/2008 | Wang et al. |
| 2008/0262654 | A1 | 10/2008 | Omori et al. |
| 2008/0281343 | A1 | 11/2008 | Dewey et al. |
| 2009/0000626 | A1 | 1/2009 | Quaid et al. |
| 2009/0000627 | A1 | 1/2009 | Quaid et al. |
| 2009/0012531 | A1 | 1/2009 | Quaid et al. |
| 2009/0012532 | A1 | 1/2009 | Quaid et al. |
| 2009/0024142 | A1 | 1/2009 | Ruiz Morales |
| 2009/0099520 | A1 | 4/2009 | Millman et al. |
| 2009/0259412 | A1 | 10/2009 | Brogardh |
| 2009/0326540 | A1* | 12/2009 | Estes ................ B23B 31/10741 |
| | | | 279/78 |
| 2010/0034605 | A1 | 2/2010 | Huckins et al. |
| 2010/0041991 | A1 | 2/2010 | Roundhill |
| 2010/0079099 | A1 | 4/2010 | Katsuki et al. |
| 2010/0152533 | A1 | 6/2010 | Mark |
| 2010/0152614 | A1 | 6/2010 | Mark |
| 2010/0152615 | A1 | 6/2010 | Mark et al. |
| 2010/0152756 | A1 | 6/2010 | Mark |
| 2010/0152758 | A1 | 6/2010 | Mark et al. |
| 2010/0152760 | A1 | 6/2010 | Mark |
| 2010/0152761 | A1 | 6/2010 | Mark |
| 2010/0152792 | A1 | 6/2010 | Ralph et al. |
| 2010/0152795 | A1 | 6/2010 | Mark |
| 2010/0168723 | A1 | 7/2010 | Suarez et al. |
| 2010/0176925 | A1 | 7/2010 | Tethrake et al. |
| 2010/0204713 | A1 | 8/2010 | Ruiz Morales |
| 2010/0249817 | A1 | 9/2010 | Mark |
| 2010/0331859 | A1 | 12/2010 | Omori |
| 2011/0010012 | A1 | 1/2011 | Murayama et al. |
| 2011/0015649 | A1 | 1/2011 | Anvari et al. |
| 2011/0034930 | A1 | 2/2011 | Buschmann et al. |
| 2011/0066161 | A1 | 3/2011 | Cooper |
| 2011/0082462 | A1 | 4/2011 | Suarez et al. |
| 2011/0087238 | A1 | 4/2011 | Wang et al. |
| 2011/0160910 | A1 | 6/2011 | Preisinger et al. |
| 2011/0213383 | A1 | 9/2011 | Lee et al. |
| 2011/0218551 | A1 | 9/2011 | Devengenzo et al. |
| 2011/0243673 | A1 | 10/2011 | Svagr |
| 2011/0301611 | A1* | 12/2011 | Garcia ................ A61B 17/8875 |
| | | | 606/104 |
| 2012/0029354 | A1 | 2/2012 | Mark et al. |
| 2012/0053606 | A1 | 3/2012 | Schmitz et al. |
| 2012/0078279 | A1 | 3/2012 | Mark |
| 2012/0089154 | A1 | 4/2012 | Green et al. |
| 2012/0109150 | A1 | 5/2012 | Quaid et al. |
| 2012/0109172 | A1 | 5/2012 | Schmitz et al. |
| 2012/0116391 | A1 | 5/2012 | Houser et al. |
| 2012/0130375 | A1 | 5/2012 | Gillard et al. |
| 2012/0157879 | A1 | 6/2012 | Mark et al. |
| 2012/0197182 | A1 | 8/2012 | Millman et al. |
| 2012/0209314 | A1 | 8/2012 | Weir et al. |
| 2012/0234126 | A1 | 9/2012 | Gosselin et al. |
| 2012/0259337 | A1 | 10/2012 | del Rio et al. |
| 2012/0277663 | A1 | 11/2012 | Millman et al. |
| 2012/0283706 | A1 | 11/2012 | Blust |
| 2012/0296203 | A1 | 11/2012 | Hartmann et al. |
| 2012/0319399 | A1 | 12/2012 | Schweizer et al. |
| 2012/0330429 | A1 | 12/2012 | Axelson, Jr. et al. |
| 2013/0060278 | A1* | 3/2013 | Bozung ................ A61B 34/70 |
| | | | 606/205 |
| 2013/0172903 | A1 | 7/2013 | Suarez et al. |
| 2013/0268120 | A1 | 10/2013 | Grygorowicz et al. |
| 2013/0277922 | A1 | 10/2013 | Estes |
| 2014/0232316 | A1 | 8/2014 | Philipp |
| 2014/0276949 | A1 | 9/2014 | Staunton et al. |
| 2014/0324050 | A1 | 10/2014 | Masson |
| 2015/0272571 | A1 | 10/2015 | Leimbach et al. |
| 2015/0272575 | A1 | 10/2015 | Leimbach et al. |
| 2016/0076590 | A1 | 3/2016 | Moratz |
| 2018/0110572 | A1 | 4/2018 | Flatt |
| 2018/0168639 | A1 | 6/2018 | Shelton, IV et al. |
| 2018/0271604 | A1 | 9/2018 | Grout et al. |
| 2018/0347301 | A1* | 12/2018 | Hilliard ................ E21B 21/10 |
| 2019/0000473 | A1 | 1/2019 | Shelton, IV et al. |
| 2019/0231447 | A1 | 8/2019 | Ebbitt et al. |
| 2019/0262009 | A1 | 8/2019 | Cheng |
| 2020/0093555 | A1 | 3/2020 | Flatt |

FOREIGN PATENT DOCUMENTS

| | | | |
|---|---|---|---|
| EP | 0456470 | A1 | 11/1991 |
| EP | 0788865 | A1 | 8/1997 |
| EP | 1264653 | A2 | 12/2002 |
| EP | 1629782 | A1 | 3/2006 |
| EP | 2272446 | A2 | 1/2011 |
| EP | 3181275 | A1 | 6/2017 |
| EP | 3388173 | A1 | 10/2018 |
| GB | 1458886 | A | 12/1976 |
| JP | 4355259 | B2 | 10/2009 |
| JP | 2014066345 | A | 4/2014 |
| WO | 2007002230 | A1 | 1/2007 |
| WO | 2007016060 | A2 | 2/2007 |
| WO | 2010075404 | A1 | 7/2010 |
| WO | 2012166807 | A1 | 12/2012 |
| WO | 2012178031 | A1 | 12/2012 |
| WO | 2013033566 | A1 | 3/2013 |

OTHER PUBLICATIONS

English language abstract and machine-assisted English translation for JP 2014-066345 A extracted from espacenet.com database on Oct. 6, 2021, 11 pages.

English language abstract and machine-assisted English translation for JP 4355259 B2 extracted from espacenet.com database on Oct. 6, 2021, 9 pages.

Hu, Gaofeng et al., "Study on Variable Pressure/Position Preload Spindle-Bearing System by Using Piezoelectric Actuators Under Close-Loop Control", International Journal of Machine Tools and Manufacture, vol. 125, https://www.sciencedirect.com/science/article/abs/pii/S089069551730158X, Feb. 2018, pp. 68-88.

Hwang, Young Kug et al., "Development of Automatic Variable Preload Device for Spindle Bearing by Using Centrifugal Force", International Journal of Machine Tools and Manufacture, vol. 49, Issue 10, Aug. 2009, pp. 781-787.

Liu, Jing et al., "Dynamic Modeling for Rigid Rotor Bearing Systems with a Localized Defect Considering Additional Deformations at the Sharp Edges", Journal of Sound and Vibration, vol. 398, https://www.researchgate.net/figure/A-rigid-rotorA-angular-contact-ball-bearings-system_fig1_315434621, 2017, pp. 84-102.

Machine-assisted English language abstract and machine-assisted English translation for EP 3 181 275 A1 extracted from espacenet.com database on Oct. 6, 2021, 15 pages.

Pardo, "Crank Bearings", http://pardo.net/bike/pic/fail-008/000.html, 2020, 10 pages.

Practical Machinist, "Thread: Surface Grinder, Angular Contact Bearings", https://www.practicalmachinist.com/vb/machine-reconditioning-scraping-and-inspection/surface-grider-angular-contact-bearings-303234/, 2015, 10 pages.

(56)               References Cited

OTHER PUBLICATIONS

Santora, Mike, "Why is Preload Necessary in Some Bearing Applications?", Bearing Tips, https://www.bearingtips.com/preload-necessary-bearing-applications/Mar. 21, 2016, 12 pages.
International Search Report for Application No. PCT/US2021/051992 dated Jan. 21, 2022, 2 pages.

* cited by examiner

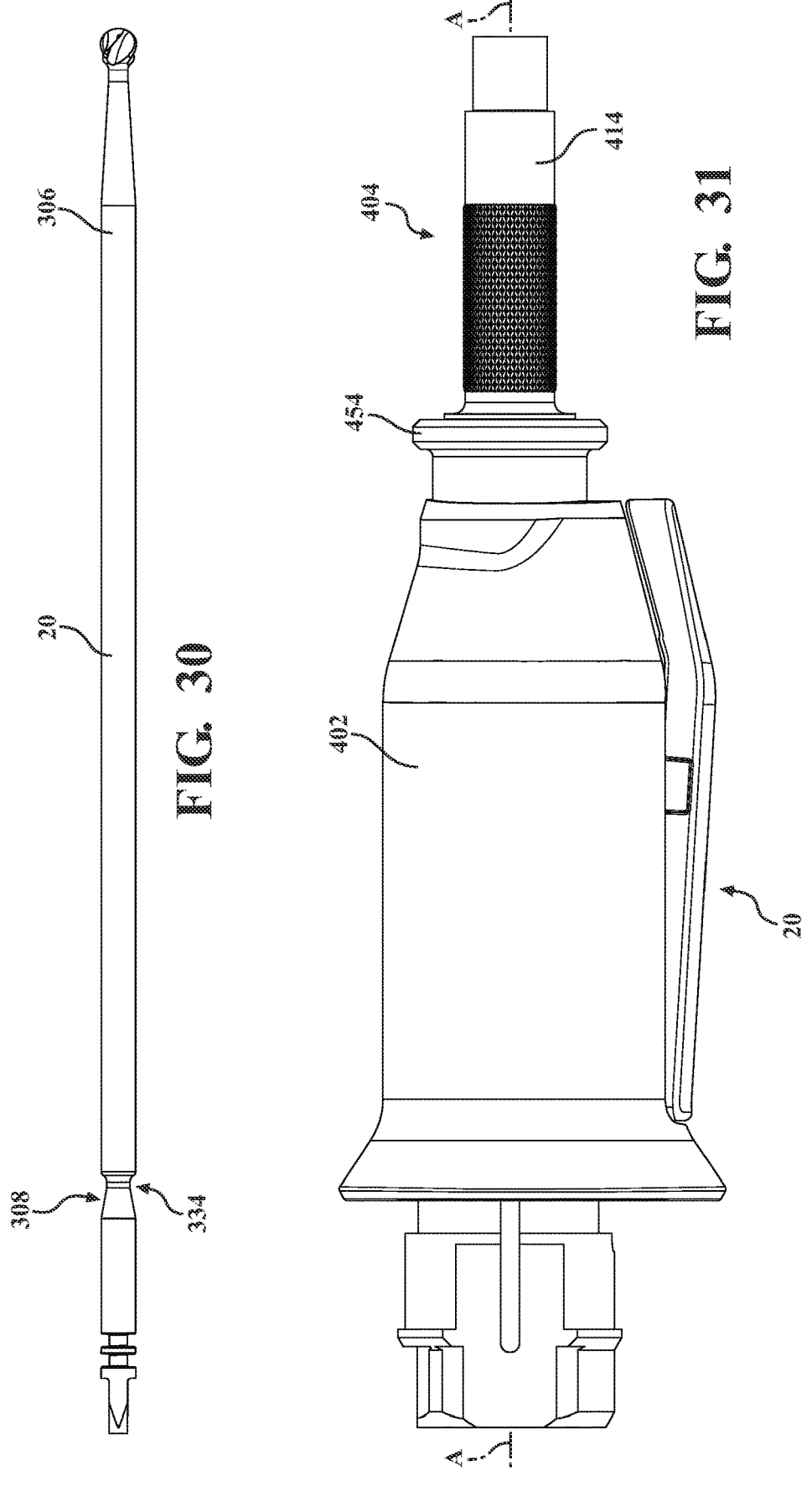

INTERLOCKING COLLET SYSTEM FOR A SURGICAL DEVICE

CROSS-REFERENCE TO RELATED APPLICATIONS

This patent application claims priority to and all advantages of U.S. Provisional Patent Application No. 63/082,514 filed Sep. 24, 2020, the entire contents of which are incorporated herein by reference.

BACKGROUND

Robotic systems are commonly used to perform surgical procedures and typically include a robot comprising a robotic arm and an end effector coupled to an end of the robotic arm and presenting a tool. The end effector includes a handle for manipulating the position of the tool.

In some conventional systems, the end effectors utilize a collet to couple the tool with end effector. While the collets do permit coupling, they often include a single locking mechanism that facilitates retention of the tool in a single direction. However, it is beneficial to provide retention in opposing directions along the axis of rotation of the tool to prevent movement along the axis. Movement along the axis alters the location at which the tool cuts a workpiece (such as bone). Furthermore, the use of a single locking mechanism retaining the tool in a single direction imparts a single bending moment on the tool at the locking mechanism when a lateral load is exerted on the tool. In addition to stress exerted on the tool, the single bending moment may space a portion of the locking mechanism from the tool, causing the tool to slip when rotated.

As such, there is a need in the art for collets that address at least the aforementioned problems.

SUMMARY

According to a first aspect, an interlocking collet system is provided. The interlocking collet system comprises an attachment comprising first and second attachment surfaces spaced from one another. The system further comprises a collet for selectively retaining the attachment. The collet comprises a housing configured to extend along an axis between first and second ends. The housing defines a bore along the axis for selectively disposing and retaining the attachment therein in an installed position. The collet further comprises first and second locking members disposed within the bore of the housing and each being moveable along the axis. The collet further comprises at least one bias member disposed within the bore of the housing. The at least one bias member is arranged to position the first locking member along the axis in a first position in which the first locking member is configured to contact the first attachment surface of the attachment. The at least one bias member is arranged to position the second locking member along the axis in a second position in which the second locking member is configured to contact the second attachment surface of the attachment. The first and second locking members in the first and second positions, respectively, are configured to exert opposing axial forces on the attachment.

According to a second aspect, a collet for selectively retaining an attachment is provided. The collet comprises a housing configured to extend along an axis between first and second ends. The housing defines a bore along the axis for selectively disposing and retaining the attachment therein in an installed position. The collet further comprises first and second locking members disposed within the bore of the housing and each being moveable along the axis. The collet further comprises at least one bias member disposed within the bore of the housing. The at least one bias member is arranged to position the first locking member along the axis in a first position in which the first locking member is configured to contact the first attachment surface of the attachment. The at least one bias member is arranged to position the second locking member along the axis in a second position in which the second locking member is configured to contact the second attachment surface of the attachment. The first and second locking members in the first and second positions, respectively, are configured to exert opposing axial forces on the attachment.

According to a third aspect, an attachment is provided which is configured for selective retention to a collet having first and second locking members. The attachment comprises first and second attachment surfaces spaced from one another, which when contacting the first and second locking members, are configured to exert opposing axial forces on the attachment for axially retaining the attachment.

According to a fourth aspect, an end effector is provided comprising a nose tube collet for selectively retaining a surgical tool. The surgical tool comprising first and second attachment surfaces spaced from one another. The nose tube collet comprises a housing configured to extend along an axis between first and second ends. The housing defines a bore along the axis for selectively disposing and retaining the surgical tool therein in an installed position. The nose tube collet further comprises first and second locking members disposed within the bore of the housing and each being moveable along the axis. The nose tube collet further comprises at least one bias member disposed within the bore of the housing. The at least one bias member is arranged to position the first locking member along the axis in a first position in which the first locking member is configured to contact the first attachment surface of the surgical tool. The at least one bias member is arranged to position the second locking member along the axis in a second position in which the second locking member is configured to contact the second attachment surface of the surgical tool. The first and second locking members in the first and second positions, respectively, are configured to exert opposing axial forces on the surgical tool.

According to a fifth aspect, a robotic system is provided, comprising: an end effector being configured to receive a surgical tool, and a plurality of links and joints being configured to support the end effector; the end effector comprising a nose tube collet for selectively retaining the surgical tool. The surgical tool comprising first and second attachment surfaces spaced from one another. The nose tube collet comprises a housing configured to extend along an axis between first and second ends. The housing defines a bore along the axis for selectively disposing and retaining the surgical tool therein in an installed position. The nose tube collet further comprises first and second locking members disposed within the bore of the housing and each being moveable along the axis. The nose tube collet further comprises at least one bias member disposed within the bore of the housing. The at least one bias member is arranged to position the first locking member along the axis in a first position in which the first locking member is configured to contact the first attachment surface of the surgical tool. The at least one bias member is arranged to position the second locking member along the axis in a second position in which the second locking member is configured to contact the second attachment surface of the surgical tool. The first and second locking members in the first and second positions, respectively, are configured to exert opposing axial forces on the surgical tool.

According to a sixth aspect, an interlocking collet system comprising: a housing configured to extend along an axis between first and second ends and an outer surface defining a first attachment surface and a second attachment surface; a slider defining a second bore for receiving the first and second locking members disposed within the bore of the slider and each being moveable along the axis; and wherein the first attachment surface and the second attachment surface each comprise a first portion and a second portion defining a recess in the outer surface of the housing; wherein the first portion of the first attachment surface and the second attachment surface is oriented at a first slope relative to the outer surface, and the second portion of the first attachment surface and the second attachment surface is oriented at a second slope relative to the outer surface.

According to a seventh aspect, an interlocking collet system comprising: a housing configured to extend along an axis between first and second ends and an outer surface defining a first attachment surface and a second attachment surface; a slider defining a second bore for receiving the first and second locking members disposed within the bore of the slider and each being moveable along the axis; and wherein the first attachment surface and the second attachment surface each comprise a first portion and a second portion defining a recess in the outer surface of the housing; wherein the first portion of the first attachment surface is positioned closer to the second end of the housing than the second portion of first attachment surface; and wherein the first portion of the second attachment surface is positioned closer to the first end of the housing than the second portion of second attachment surface.

According to a eighth aspect, an interlocking collet system comprising: a housing configured to extend along an axis between first and second ends and an outer surface defining a first attachment surface and a second attachment surface; a slider defining a second bore for receiving the first and second locking members disposed within the bore of the slider and each being moveable along the axis; and wherein the first attachment surface and the second attachment surface each comprise a first portion and a second portion defining a recess in the outer surface of the housing; wherein the first portion of the first attachment surface is positioned closer to the second end of the housing than the second portion of first attachment surface; and wherein the first portion of the second attachment surface is positioned closer to the first end of the housing than the second portion of second attachment surface.

Any of the above aspects can be utilized individually, or in combination.

Any of the above aspects can be utilized with any of the following implementations:

In one implementation, the interlocking collet system can be used with a first surgical component and a second surgical component, wherein the collet is coupled to the first surgical component and the attachment is coupled to the second surgical component. In one implementation, the first surgical component is any one of a surgical navigation tracker, a surgical guide component, a powered surgical instrument component, a surgical hand tool component, a surgical robot component, a passive arm component, a surgical table component, and an imaging device component, and the second surgical component is any one of a surgical navigation tracker, a surgical guide component, a powered surgical instrument component, a surgical hand tool component, a surgical robot component, a passive arm component, a surgical table component, and an imaging device component.

In one implementation, the interlocking collet system can be used with an end effector whereby the housing of the collet is further defined as a nose tube of the end effector and the attachment is further defined as a surgical tool that can be inserted into the nose tube. In one implementation, at least one of the first and second attachment surfaces are skewed relative to the axis to facilitate the opposing axial forces on the attachment.

In one implementation, the at least one bias member has a stiffness that is configured to exert the opposing axial forces on the attachment through the first and second locking members to retain the attachment in the installed position. In one implementation, the stiffness of the at least one bias member maintains the first locking member in the first position and the second locking member in the second position to prevent removal of the attachment from the bore.

In one implementation, the housing comprises first and second housing surfaces spaced from one another and disposed at least partially within the bore, with the first locking member configured to contact both of the first attachment surface and the first housing surface in the first position and the second locking member configured to contact both of the second attachment surface and the second housing surface in the second position.

In one implementation, the first housing surface is proximate to the first end of the housing and the second housing surface is proximate to the second end of the housing. In one implementation, at least one of the first housing surface and the first attachment surface is skewed relative to the axis and at least one of the second housing surface and the second attachment surface is skewed relative to the axis to facilitate the opposing axial forces on the attachment.

In one implementation, the first housing surface and the first attachment surface define a first orthogonal distance therebetween perpendicular to the axis and the second housing surface and the second attachment surface define a second orthogonal distance therebetween perpendicular to the axis, with the skewed configuration of at least one of the first housing surface and the first attachment surface configured to facilitate a reduction in the first orthogonal distance when the attachment moves from the installed position in a first direction along the axis and wedges the first locking member between the housing and the attachment to prevent removal of the attachment from the bore in the first direction, and with the skewed configuration of at least one of the second housing surface and the second attachment surface configured to facilitate a reduction in the second orthogonal distance when the attachment moves from the installed position in a second direction along the axis, opposite the first direction, and wedges the second locking member between the housing and the attachment to prevent removal of the attachment from the bore in the second direction.

In one implementation, the first housing surface and the first attachment surface define a first axial distance therebetween parallel to the axis, with the skewed configuration of both of the first housing surface and the first attachment surface configured to facilitate a reduction in the first axial distance when the attachment moves from the installed position in the first direction along the axis and wedges the first locking member between the housing and the attachment to prevent removal of the attachment from the bore in the first direction.

In one implementation, the second housing surface and the second attachment surface define a second axial distance therebetween parallel to the axis, with the skewed configuration of both of the second housing surface and the second attachment surface configured to facilitate a reduction in the second axial distance when the attachment moves from the installed position in the second direction along the axis and wedges the second locking member between the housing and the attachment to prevent removal of the attachment from the bore in the second direction.

In one implementation, the attachment comprises at least one attachment unlock surface adjacent the first and second attachment surfaces and the housing comprises at least one housing unlock surface adjacent the first and second housing surfaces, with the attachment and housing unlock surfaces concentrically spaced from one another and configured to dispose the first and second locking members therebetween to facilitate movement of the attachment, independent of the housing, along the axis.

In one implementation, the at least one attachment unlock surface is disposed between the first and second attachment surfaces and the at least one housing unlock surface is disposed between the first and second housing surfaces. In one implementation, the first and second attachment surfaces face opposing directions along the axis, with the first locking member disposed along the axis between the first attachment surface and one of the first and second ends of the housing, and with the second locking member configured to be disposed along the axis between the second attachment surface and the other one of the first and second ends of the housing.

In one implementation, the first and second attachment surfaces are symmetric about a plane orthogonal to the axis. In one implementation, the first attachment surface extends inwardly toward the axis such that the first attachment surface defines a first recess configured to receive the first locking member therein. In one implementation, the second attachment surface extends outwardly away from the axis. In one implementation, the second attachment surface extends inwardly toward the axis such that the second attachment surface defines a second recess configured to receive the second locking member therein.

In one implementation, each of the first and second locking members comprise a frame and a plurality of spheres retained by the frame and radially disposed around the axis, with each of the spheres being movable, relative to the frame, transverse to the axis.

In one implementation, the at least one bias member is further defined as at least one compression spring. In one implementation, the at least one bias member is a single bias member disposed between the first and second locking members and configured to bias the locking members away from one another.

In one implementation, a slide is disposed along the housing and movable along the axis, with the slide configured to engage and move the first and second locking members along the axis against the bias of the at least one bias member.

In one implementation, the housing defines at least one slot extending longitudinally along the axis and opening into the bore and an exterior of the housing, with each of the first and second locking members comprising a projection extending through the at least one slot and disposed in the exterior, and with the slide configured to engage the projections to move the first and second locking members along the axis against the bias of the bias member.

In one implementation, the at least one bias member biases the first and second locking members away from one another, with the slide defining first and second abutment surfaces spaced from and facing one another along the axis and with the projections of the first and second locking members disposed between the abutment surfaces, with the first abutment surface configured to engage and move the projection of the first locking member when the slide moves in one direction along the axis and with the second abutment surface configured to engage and move the projection of the second locking member when the slide moves in another direction along the axis.

In one implementation, at least one of the first and second attachment surfaces extend outwardly away from the axis. In one implementation, the first and second locking member, that respectively correspond with the outwardly extending first and second attachment surface, have an annular configuration around the axis and define an inner diameter, with the outwardly extending first and second attachment surfaces having an outer diameter that increases as the surfaces extend further from the axis such that first and second locking member moves up the first and/or second attachment surface until the inner and outer diameters equal one another. In one implementation, the outwardly extending first and second attachment surface encircles the attachment around the axis.

Accordingly, interlocking collet system provides the advantage of symmetrically retaining the attachment along the axis through the opposing axial forces exerted by the first and second locking members. Furthermore, the symmetric configuration of the first and second locking members exerting the opposing axial forces provide the advantage of facilitating removal of attachment in either of the two opposing directions along the axis. Moreover, the utilization of the first and second locking members, provides the benefit of resisting bending moments on the attachment when a lateral load is exerted on the attachment. The first and second locking members distribute the load along the attachment. By distributing the load, the deflection of the attachment along the axis is reduced. Additional advantages will be understood from the Detailed Description and Figures.

BRIEF DESCRIPTION OF THE DRAWINGS

Advantages of the present invention will be readily appreciated as the same becomes better understood by reference to the following detailed description when considered in connection with the accompanying drawings wherein:

FIG. 30 is a side view of an exemplary configuration of the attachment removably secured by the interlocking collet system of the end effector of FIGS. 25-27.

FIG. 31 is a side view of another example of an end effector for use with the robotic system shown in FIG. 1, including a handle and an exemplary configuration of an interlocking collet system.

DETAILED DESCRIPTION

I. Robotic System Overview

Referring to the Figures, wherein like numerals indicate like or corresponding parts throughout the several views, a system 10 (hereinafter "system") is shown throughout.

Figure 1:
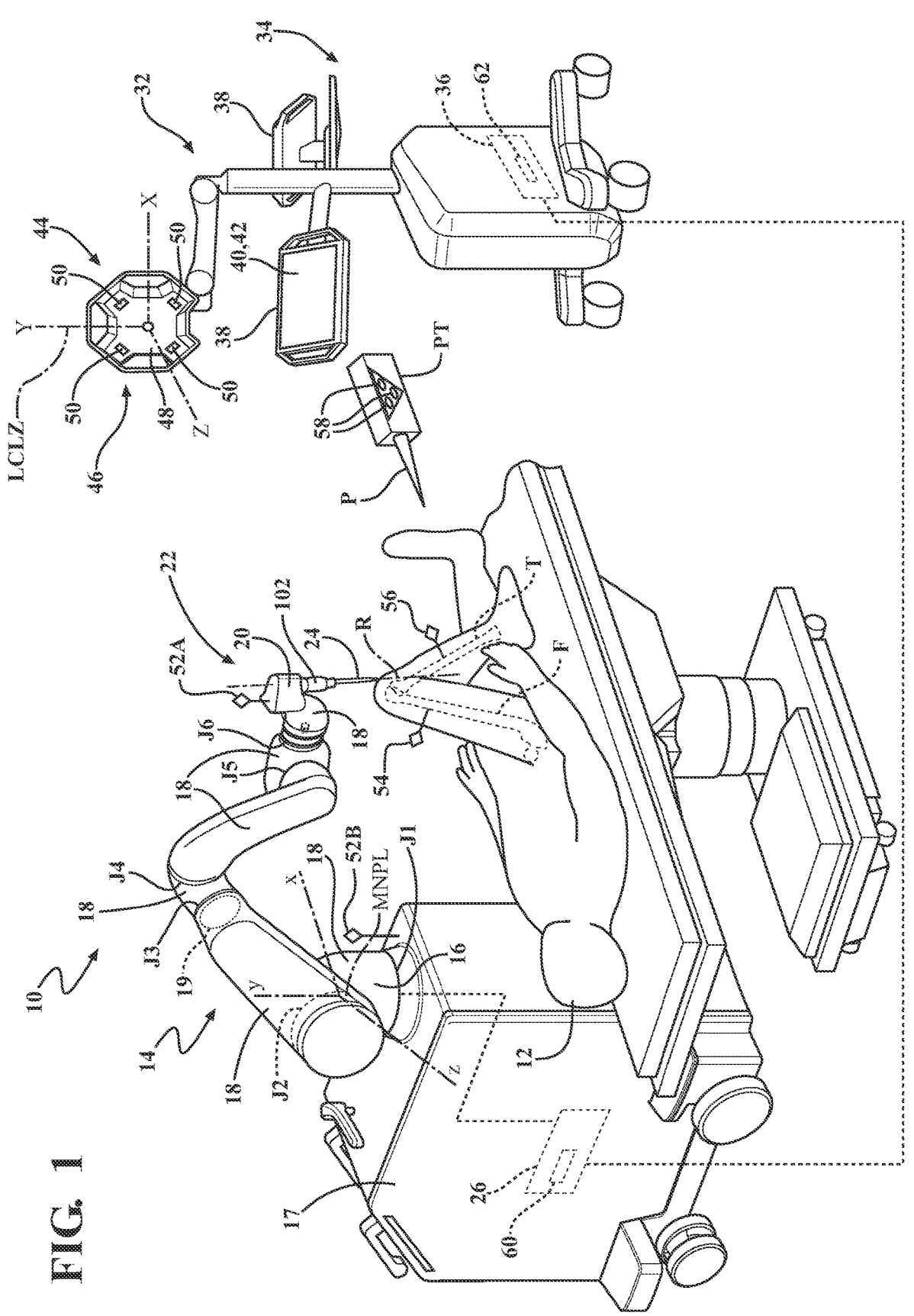
FIG. 1 is a perspective view of a robotic system for manipulating a target tissue of a patient with a tool, according to one example.

As shown in FIG. 1, the system 10 may treat an anatomy (surgical site) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants, including unicompartmental, bicompartmental, multicompartmental, or total knee implants. Some of these types of implants are shown in U.S. Pat. No. 9,937,058, entitled, "Prosthetic Implant and Method of Implantation," the disclosure of which is hereby incorporated by reference. The system 10 and method disclosed herein may be used to perform other procedures, surgical or non-surgical, or may be used in industrial applications or other applications where robotic systems are utilized.

The system 10 may include a robotic manipulator 14. The robotic manipulator 14 has a base 16 and plurality of links 18. A manipulator cart 17 supports the robotic manipulator 14 such that the robotic manipulator 14 is fixed to the manipulator cart 17. The links 18 collectively form one or more arms of the robotic manipulator 14. The robotic manipulator 14 may have a serial arm configuration (as shown in FIG. 1) or a parallel arm configuration. In other examples, more than one robotic manipulator 14 may be utilized in a multiple arm configuration. The robotic manipulator 14 may comprise a plurality of (prismatic and/or rotating) joints (J) and a plurality of motor and/or joint encoders 19 located at the joints (J) for determining position data of the joints (J). For simplicity, only one joint encoder 19 is illustrated in FIG. 1, although it is to be appreciated that the other joint encoders 19 may be similarly illustrated. The robotic manipulator 14 according to one example has six joints (J1-J6) implementing at least six-degrees of freedom (DOF) for the robotic manipulator 14. However, the robotic manipulator 14 may have any number of degrees of freedom and may have any suitable number of joints (J) and redundant joints (J).

A surgical tool 20 (hereinafter "tool") couples to the robotic manipulator 14 and is movable relative to the base 16 to interact with the anatomy in certain modes. The tool 20 is or can form part of an end effector 22. The tool 20 may be grasped by the operator. One exemplary arrangement of the robotic manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The robotic manipulator 14 and the tool 20 may be arranged in alternative configurations. The tool 20 can be like that shown in U.S. Pat. No. 9,566,121, filed on Mar. 15, 2014, entitled, "End Effector of a Surgical Robotic Manipulator," hereby incorporated by reference.

The positioning of the end effector 22 and the tool 20 is defined by the robotic manipulator 14. This positioning may not be ideally suited for the ergonomics of an operator. To that end, the end effector 22 may include a handle 102 that is rotatable about a rotational axis R. The rotatable handle 102 allows the operator to hold the tool 20 in the most comfortable position while the robotic manipulator 14 moves the tool 20 into the necessary position for robotic manipulation. Exemplary arrangements of the handle 102 rotatable about the rotational axis R are described in U.S. Pat. No. 9,566,121, entitled, "End Effector of a Surgical Robotic Manipulator," and U.S. Patent Application Publication No. 2018/0110572, filed on Oct. 21, 2016, entitled, "Systems and Tools for Use with Surgical Robotic Manipulators," the disclosures of which are hereby incorporated by reference.

The tool 20 includes an energy applicator 24 designed to contact the target site, such as the tissue of the patient 12 at the surgical site. The energy applicator 24 may be a drill, a saw blade, a bur, an ultrasonic vibrating tip, or the like.

The system 10 includes a controller 30. The controller 30 includes software and/or hardware for controlling the robotic manipulator 14. The controller 30 directs the motion of the robotic manipulator 14 and controls a state (position and/or orientation) of the tool 20 with respect to a coordinate system of the manipulator 14.

As shown in FIG. 1, the system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the robotic manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The navigation system 32 includes one or more trackers. In one example, the trackers include a pointer tracker PT, one or more manipulator trackers 52, a first patient tracker 54, and a second patient tracker 56. In the illustrated example of FIG. 1, the manipulator tracker 52 is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the robotic manipulator 14, in addition to, or other than the tool 20, such as the base 16 (i.e., tracker 52B), or any one or more links 18 of the robotic manipulator 14. The trackers 52, 54, 56, PT may be fixed to their respective components in any suitable manner.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the navigation system 32 is shown in the Figures, the navigation system 32 may have any other suitable configuration for tracking the robotic manipulator 14 and the patient 12. In one example, the navigation system 32 and/or localizer 44 are ultrasound-based. In another example, the navigation system 32 and/or localizer 44 are radio frequency (RF)-based.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

The controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the robotic manipulator 14. In one example, as shown in FIG. 1, the manipulator controller is implemented on the manipulator computer 26. The manipulator controller 60 may receive and process data from a single source or multiple sources. The controller 30 further includes a navigation controller 62 for communicating the state data relating to the femur F, tibia T, and robotic manipulator 14 to the manipulator controller 60. The manipulator controller 60 receives and processes the state data provided by the navigation controller 62 to direct movement of the robotic manipulator 14. In one example, as shown in FIG. 1, the navigation controller 62 is implemented on the navigation computer 36. The manipulator controller 60 or navigation controller 62 may also communicate states of the patient 12 and robotic manipulator 14 to the operator by displaying an image of the femur F and/or tibia T and the robotic manipulator 14 on the one or more displays 38. The manipulator computer 26 or navigation computer 36 may also command display of instructions or request information using the display 38 to interact with the operator and for directing the robotic manipulator 14.

The controller 30 includes a boundary generator 66. The boundary generator 66 is a software module that may be implemented on the manipulator controller 60. Alternatively, the boundary generator 66 may be implemented on other components, such as the navigation controller 62. The boundary generator 66 generates virtual boundaries for constraining the tool 20. Such virtual boundaries may also be referred to as virtual meshes, virtual constraints, or the like. The virtual boundaries may be defined with respect to a 3-D bone model registered to the one or more patient trackers 54, 56 such that the virtual boundaries are fixed relative to the bone model. The state of the tool 20 is tracked relative to the virtual boundaries. In one example, the state of the TCP is measured relative to the virtual boundaries for purposes of determining when and where haptic feedback force is applied to the robotic manipulator 14, or more specifically, the tool 20.

A tool path generator 69 is another software module run by the controller 30, and more specifically, the manipulator controller 60. The tool path generator 69 generates a path 100 for the tool 20 to traverse, such as for removing sections of the anatomy to receive an implant. One exemplary system and method for generating the tool path 100 is explained in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries and/or tool paths 100 may be generated offline rather than on the manipulator computer 26 or navigation computer 36. Thereafter, the virtual boundaries and/or tool paths 100 may be utilized at runtime by the manipulator controller 60.

II. Interlocking Collet System

Referring to the Figures, wherein like numerals indicate like or corresponding parts throughout the several views, an interlocking collet system 104 is generally shown in FIGS. 4-18. The interlocking collet system 104 comprises an attachment 106 comprising first and second attachment surfaces 108, 110 spaced from one another and a collet 112 for selectively retaining the attachment 106. As will be described below, the interlocking collet system 104 may be utilized with the system 10, and more specifically, for retaining the surgical tool 22 to the end effector 20. However, the interlocking collet system 104 may be utilized for other types of surgical components other than the surgical tool 22 and end effector 20.

As shown in FIGS. 5-18, the collet 112 comprises a housing 114 configured to extend along an axis A between first and second ends 116, 118. The housing 114 defines a bore 120 along the axis A for selectively disposing and retaining the attachment 106 therein in an installed position N. The collet 112 further comprises first and second locking members 122, 124 disposed within the bore 120 of the housing 114 and each being moveable along the axis A.

The collet 112 further comprises at least one bias member 126 disposed within the bore 120 of the housing 114. The least one bias member 126 is arranged to position the first locking member 122 along the axis A in a first position F in which the first locking member 122 is configured to contact the first attachment surface 108 of the attachment 106, as shown in FIGS. 5, 10, 17, and 18. Moreover, the at least one bias member 126 is arranged to position the second locking member 124 along the axis A in a second position S in which the second locking member 124 is configured to contact the second attachment surface 110 of the attachment 106. The first and second locking members 122, 124 in the first and second positions F, S, respectively, are configured to exert opposing axial forces on the attachment.

The opposing axial forces, exerted on the attachment 106 by the first and second locking members 122, 124, act along the axis A. As such, movement of the attachment 106 in one direction along the axis A causes one of the locking members 122, 124 to exert one of the opposing axial forces on the attachment 106. Similarly, movement of the attachment 106 in another (opposite) direction along the axis A causes the other one of the locking members 122, 124 to exert the other one of the opposing axial forces on the attachment 106. As such, the opposing axial forces exerted by the first and second locking members 122, 124 may provide the advantage of symmetrically retaining the attachment 106 along the axis A.

Devices using a single locking mechanism are susceptible to producing a bending moment on an attachment when a lateral load (i.e., transverse to the longitudinal axis of the attachment) is exerted on the attachment. The utilization of the first and second locking members 122, 124, as described herein, provides the benefit of resisting bending moments on the attachment 106 when a lateral load is exerted on the attachment 106. The first and second locking members 122, 124 distribute the load along the attachment 106, rather than exerting the load on a single point (as is the case with collets with single locking mechanisms). By distributing the load, the deflection of the attachment 106 along the axis A is reduced. In some examples, the attachment 106 is rotated about the axis A (e.g., when incorporated in the end effector 22, which will be described in greater detail below). Deflection of the attachment 106 can cause sudden, unintended, changes in the angular velocity of the attachment 106 (i.e., slip). When used with the end effector 22, uniform angular velocity provides benefits, such as, efficient and uniform removal of material (i.e., when the attachment 106 is configured as the tool 20) and cooler cutting temperatures.

As will be further described below, the collet 112 may be manipulated to remove the attachment 106 from the bore 120, along the axis A, when desired. Furthermore, the configuration of the first and second locking members 122, 124 exerting the opposing axial forces may provide the advantage of removing of attachment 106 in either of the two opposing directions along the axis A. More specifically, moving one of the first and second locking members 122, 124 away from the respective first/second position F, S (against the bias of the at least one bias member 126) may remove one of the opposing axial forces on the attachment 106 and allow the attachment 106 to move in one direction along the axis A. Likewise, moving the other one of the first and second locking members 122, 124 away from the respective first/second position F, S (against the bias of the at least one bias member 126) may remove the other one of the opposing axial forces on the attachment 106 and allow the attachment 106 to move in the other (opposing) direction along the axis A. Therefore, the collet 112 serves to selectively retain the attachment 106 along the axis A (i.e., axially).

Figure 4:
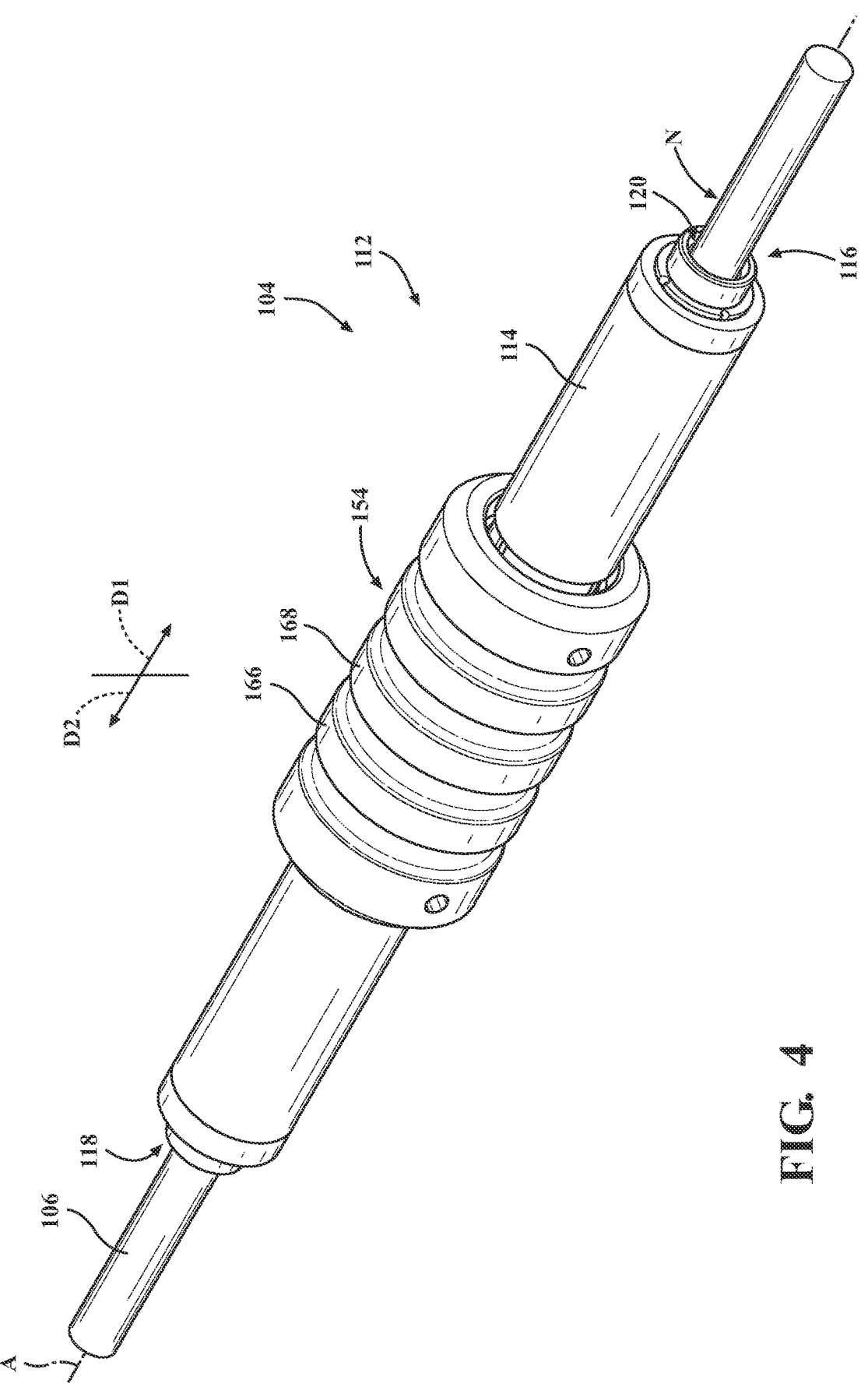
FIG. 4 is a perspective view of an interlocking collet system comprising an attachment and the collet shown in FIG. 2, with the attachment disposed in an installed position.
Figure 5:
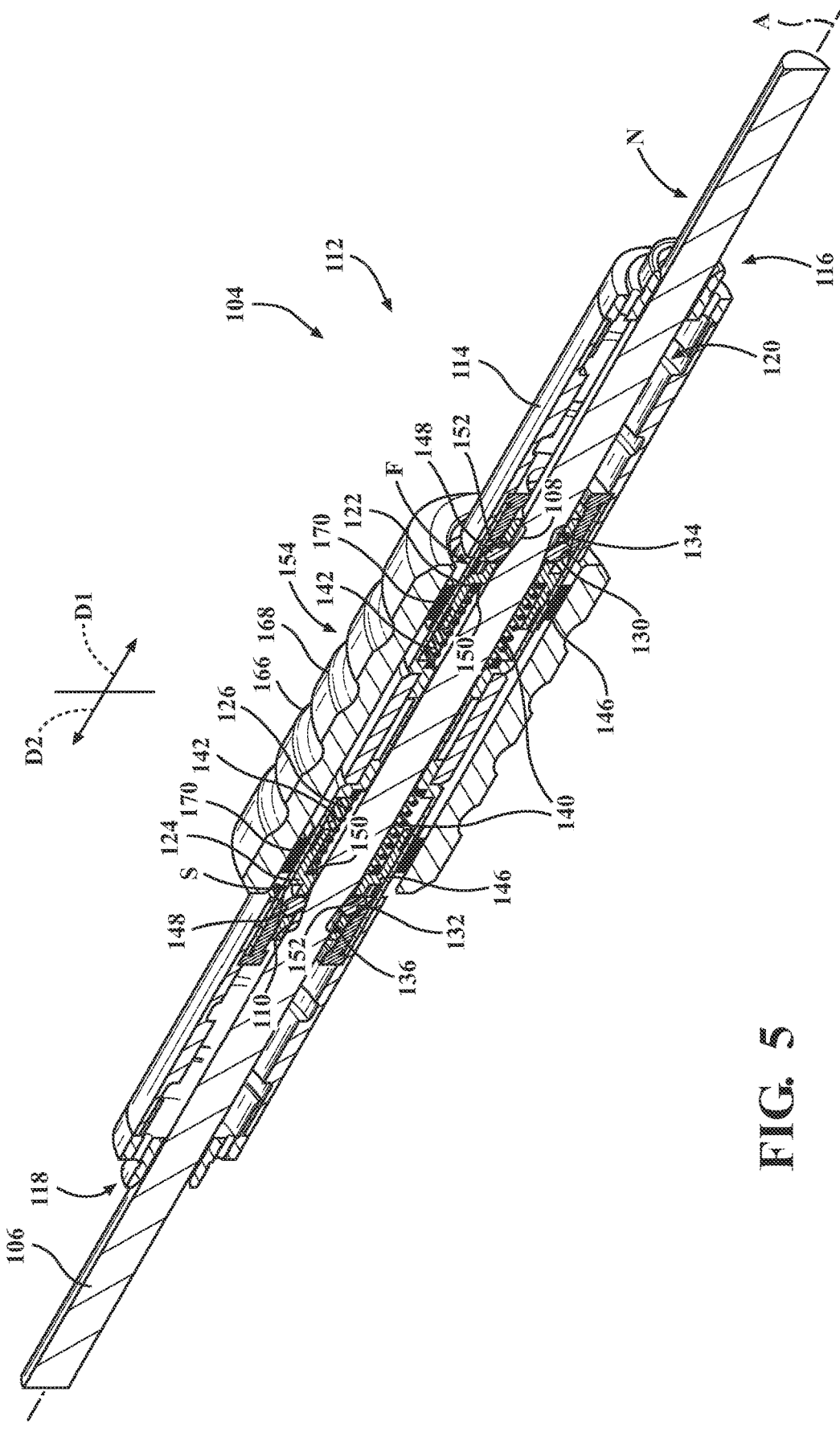
FIG. 5 is a cross-sectional perspective view of the interlocking collet system shown in FIG. 4, taken along line 5-5.
Figure 16:
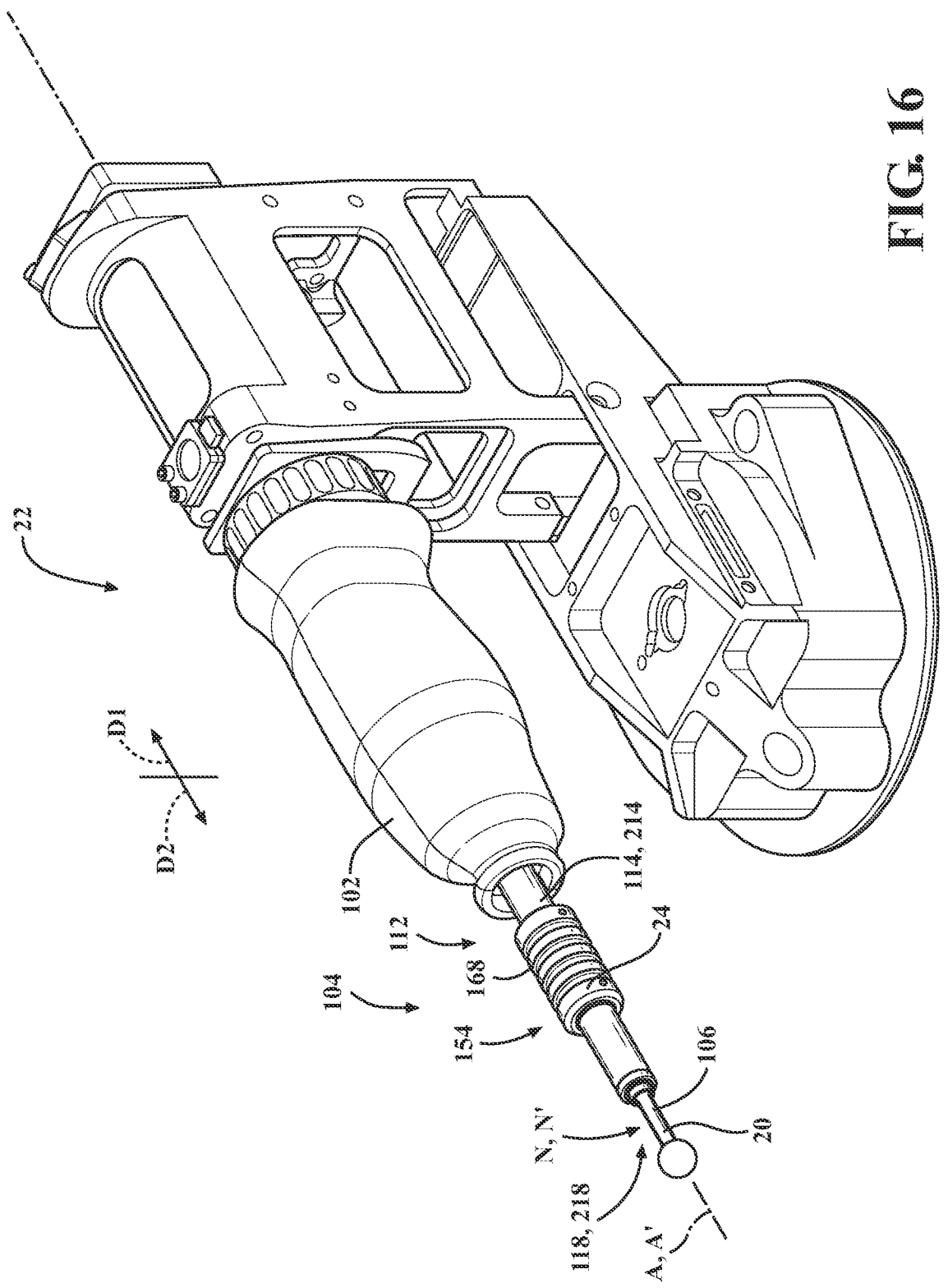
FIG. 16 is a perspective view of an end effector for use with the robotic system shown in FIG. 1, according to one example, and showing a handle and the interlocking collet system.

As shown in FIGS. 4, 5, and 16, the attachment 106 may have a generally cylindrical configuration that extends linearly along the axis A. For example, the attachment 106 can be a shaft of the surgical tool. Likewise, the bore 120 is generally configured in a corresponding cylindrical configuration extending linearly along the axis A and sized to receive the attachment 106. The corresponding cylindrical and linear configurations facilitate the selective movement of the attachment 106 along the axis A to assemble and disassemble the attachment 106 with the collet 112. More specifically, with the attachment 106 and the bore 120 of the collet 112 aligned along the axis A, the shape and size of the bore 120 allows for selective movement of the attachment 106 into and out of the bore 120. However, the attachment 106 and the bore 120 may have any configuration for receiving the attachment 106 therein. The assembly and disassembly of the attachment 106 with the collet 112 will be better understood from examples presented below.

Moreover, the attachment 106 may be configured to rotate about the axis A relative to the collet 112. For example, the generally cylindrical configuration of the attachment 106 and the bore 120 of the housing 114 allows the attachment 106 to rotate within the bore 120 without binding within the housing 114. An example of an attachment 106 that is rotatable about the axis A, relative to the collet 112, is shown in FIGS. 18-24 and will be described in greater detail below. However, the attachment 106 may be rotationally stationary relative to the collet 112. The rotation of the attachment 106 relative to the collet 112 will be better understood from examples presented below.

Figure 17:
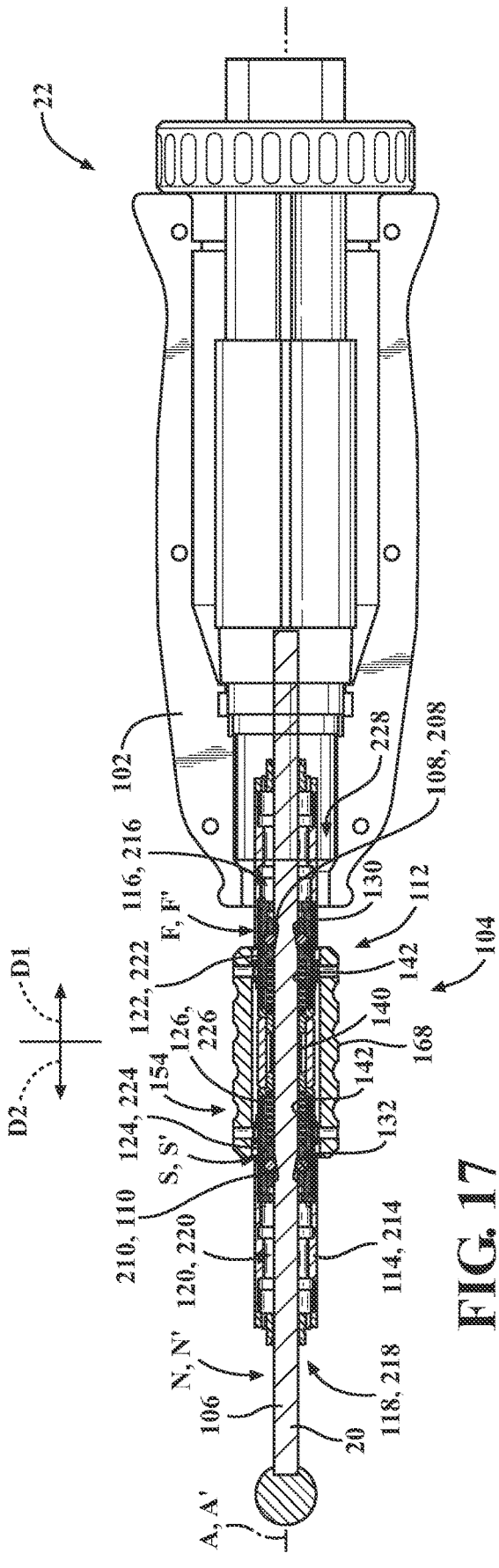
FIG. 17 is a cross-sectional view of the end effector of FIG. 16 showing the interlocking collet system used with the end effector, according to one example.
Figures 18, 19, 20:
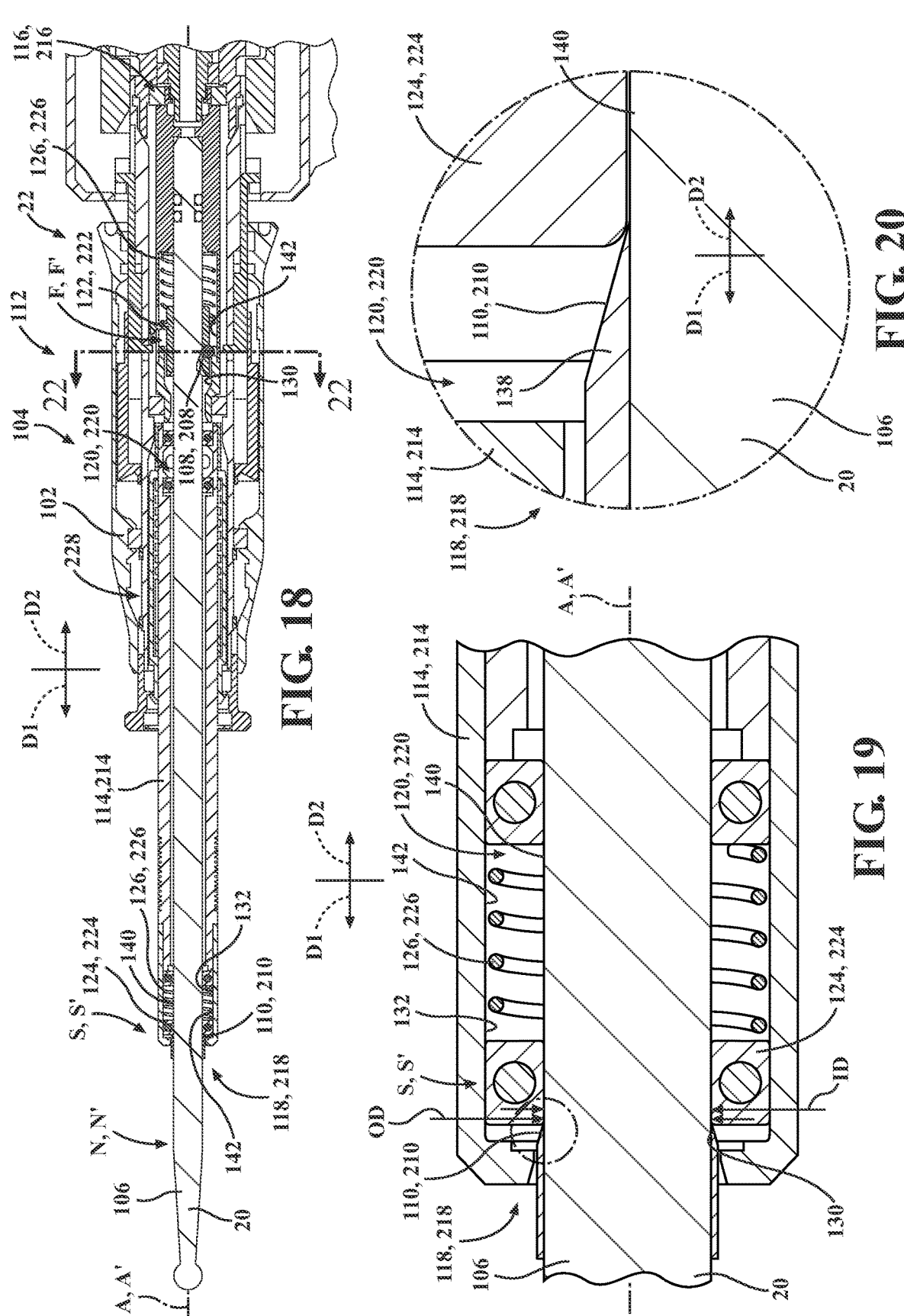
FIG. 18 is cross-sectional view of another example of an end effector using another example of an interlocking collet system.
FIG. 19 is a sectional view of the interlocking collet system shown in FIG. 18, showing a second locking member and a second attachment surface.
FIG. 20 is a sectional view of the interlocking collet system shown in FIG. 19, showing engagement between the second locking member and the second attachment surface.

In one example, the collet 112 (moreover, the interlocking collet system 104) is incorporated with the end effector 22 of the manipulator 14, as shown in FIGS. 16-18. As described above, the end effector 22 selectively retains the tool 20 (i.e., the attachment 106). The tool 20 comprises first and second tool surfaces 208, 210 (i.e., the first and second attachment surfaces 108, 110) spaced from one another.

The end effector 22 comprises a nose tube 214 (i.e., the housing 114). Like the housing 114, the nose tube 214 is configured to extend along an axis A' between first and second ends 216, 218 and defines a bore 220 along the axis A' for selectively disposing and retaining the tool 20 therein in an installed position N'. The end effector 22 also comprises first and second locking members 222, 224 disposed within the bore 220 of the nose tube 214 and each being moveable along the axis A'.

Moreover, the end effector 22 further comprises at least one bias member 226 disposed within the bore 220 of the nose tube 214. The at least one bias member 226 is arranged to position the first locking member 222 along the axis A' in a first position F' in which the first locking member 222 is configured to contact the first tool surface 208 of the tool 20. The at least one bias member 226 is arranged to position the second locking member 224 along the axis A' in a second position S' in which the second locking member is configured to contact the second tool surface 210 of the tool 20. The first and second locking members 222, 224 in the first and second positions F', S', respectively, are configured to exert opposing axial forces on the tool 20.

The nose tube 214 may be at least partially disposed within the end effector 22. In the examples shown in FIGS. 16-18, the end effector 22 comprises the handle 102 (described above) configured to be grasped by a user for directing the location and the movement of the tool 20. The handle 102 may define a handle bore 228 that extends along the axis A'. The nose tube 214 is configured to extend at least partially within the handle bore 228 and be fixed to the handle 102. However, the end effector 22 may be configured such that the nose tube 214 defines the exterior surface of the end effector 22. Said differently, the end effector 22 may not comprise the handle 102 with the nose tube 214 extending into the handle bore 228. In such a configuration, the nose tube 214 may be configured to be grasped by the user. However, the nose tube 214 may be integrated into the end effector 22 in any suitable configuration.

The details pertaining to the interlocking collet system 104 may also be applicable to the end effector 22 shown in FIGS. 16-18 (i.e., the application of the interlocking collet system 104 in the end effector 22 as described above). However, the interlocking collet system 104 is not limited solely to application with the end effector 22 as described herein. The interlocking collet system 104 may be used in any suitable application that utilizes first and second locking members 122, 124 configured to exert opposing axial forces on an attachment when the attachment is moved along an axis from an installed position N to prevent removal of the attachment from a bore.

The interlocking collet system 104 may be part of any type of surgical system other than the system 10. For example, the surgical system may comprise a first surgical component and a second surgical component, wherein the collet 112 is coupled to the first surgical component and the attachment 106 is coupled to the second surgical component. The first surgical component may be any one of a surgical navigation tracker, a surgical guide component, a powered surgical instrument component, a surgical hand tool component, a surgical robot component, a passive arm component, a surgical table component, and an imaging device component. Likewise, the second surgical component may be any one of a surgical navigation tracker, a surgical guide component, a powered surgical instrument component, a surgical hand tool component, a surgical robot component, a passive arm component, a surgical table component, and an imaging device component. Any combination of these components can be utilized with the interlocking collet system.

Additionally, the interlocking collet system 104 may be utilized in other configurations to explicitly shown in the Figures. For example, the interlocking collet system 104 may be utilized as joint between one or more of the links 18 of the robotic manipulator 14 to facilitate ease of disassembly of the links 18 ensuring reliable connection between the links 18 when assembled. Moreover, while the examples in the Figures show the attachment 106 configured to rotate about the axis A, it is to be appreciated that the collet 112 may be configured to rotate with the tool 20. Furthermore, in other examples both the attachment 106 and the collet 112 may be rotationally stationary about the axis A.

Figure 2:
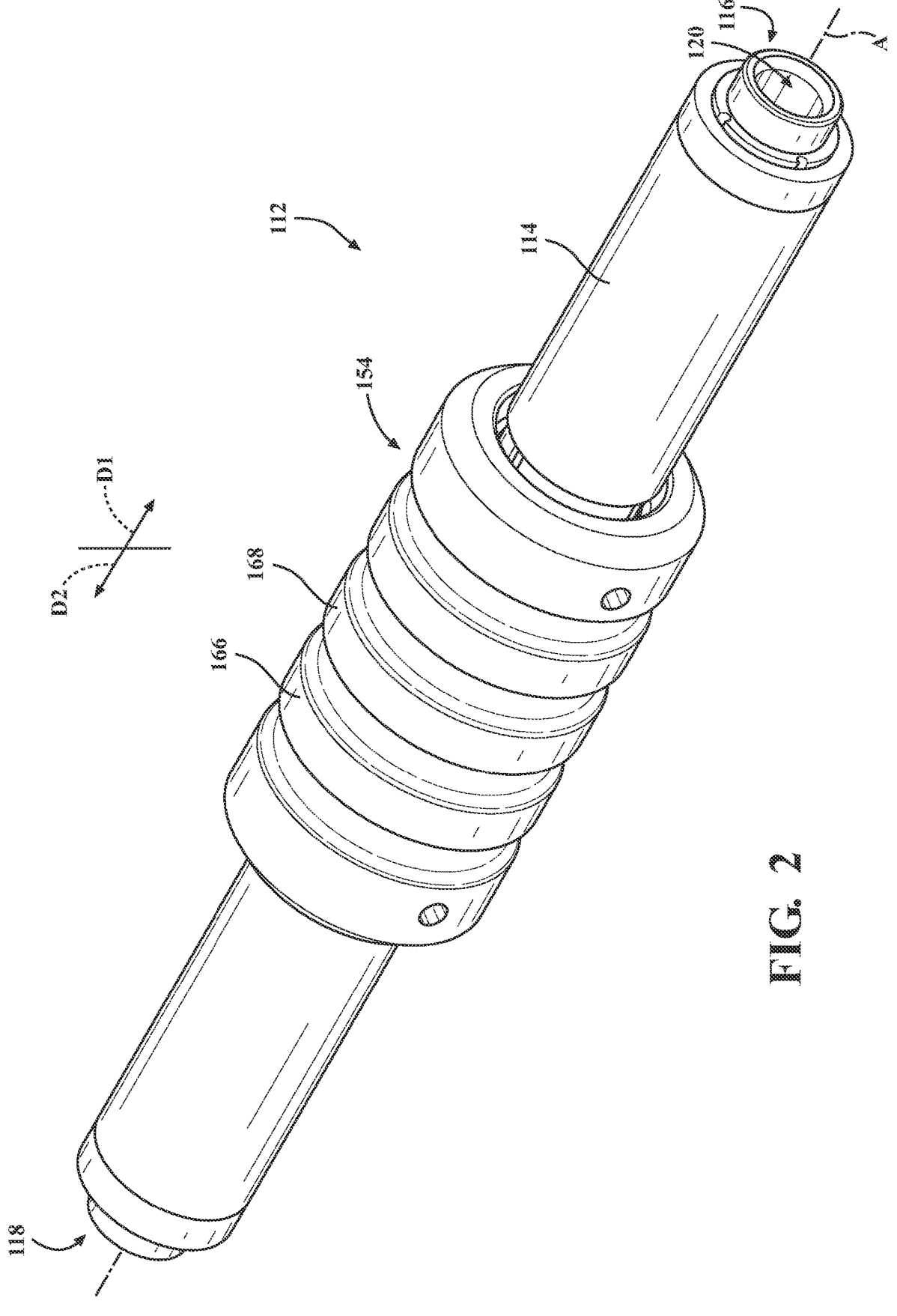
FIG. 2 is a perspective view of a collet and showing a slide.
Figure 3:
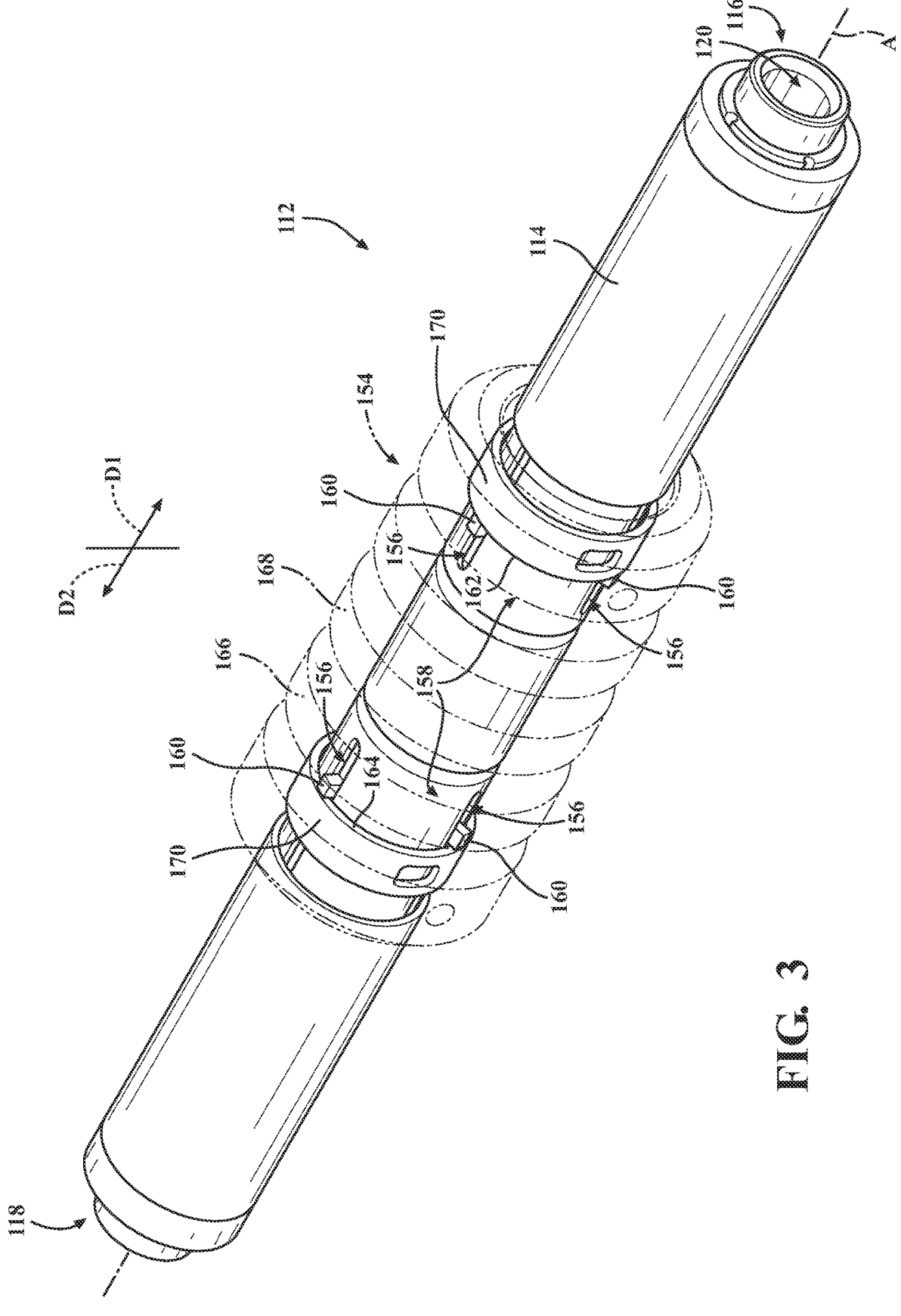
FIG. 3 is a perspective view of the collet of FIG. 2, with a grip of the slide in phantom.

As described above, the bore 120 of the housing 114 may have a generally cylindrical configuration. As such, the housing 114 may have a tubular configuration as shown in FIGS. 2 and 3. The bore 120 may be defined by a plurality of surfaces of the housing that are angled relative to one another. As such, the generally cylindrical configuration may vary in cross-sectional diameter along the axis A. However, the bore 120 may comprise any suitable configuration for receiving the attachment 106.

The housing 114 may comprise a plurality of components that are rigidly connected to one another to form the housing 114, as shown in FIGS. 5-15, 17, and 18. One or more of the components may define the bore 120. However, the housing 114 may be a single, integral component defining the bore 120 therethrough.

As described above, the at least one bias member 126 is arranged to position the first locking member 122 along the axis A in the first position F and the second locking member 124 along the axis A in the second position S, as shown in FIGS. 5, 10, 17, and 18. The disposition of the first and second locking members 122, 124 in the first and second positions F, S, respectively, configures contact between the first locking member 122 and the first attachment surface 108 and the second locking member 124 and the second attachment surface 110. The disposition of the first and second locking members 122, 124 may facilitate the opposing axial forces when the attachment 106 is moved along the axis A from the installed position N. Said differently, the mere placement of the first and second locking members 122, 124 in the first and second positions F, S may cause the opposing axial forces that retain the attachment 106 in the installed position N. As such, the at least one bias member 126 may not exert the opposing axial force on the attachment 106. Said differently, the at least one bias member 126 may have a stiffness that is sufficient to position the first and second locking members 122, 124 in contact with the first and second attachment surfaces 108, 110, respectively, and prevent movement of the locking members 122, 124 away from the attachment surfaces 108, 110, without exerting force on the attachment surfaces 108, 110. Furthermore, in this example the stiffness facilitates coupling while limiting the force needed to insert the attachment 106 into the housing 114 (i.e., due to deflection of the bias member 126 when the first and/or second locking member 122, 124 is moved to allow insertion of the attachment 106). The resistance exerted by the bias member 126 during insertion of the attachment 106 is commonly referred to in the art as pre-load. By reducing the pre-load, the effort required to insert the attachment 106 is reduced, thereby easing the assembly of the interlocking collet system 104. Furthermore, reducing the pre-load also reduces or eliminates the need of using external tools or devices that provide a mechanical advantage on the bias member 126 to facilitate insertion of the attachment 106.

In another example, the stiffness of the at least one bias member 126 is configured to exert the opposing axial forces on the attachment 106 through the first and second locking members 122, 124 to retain the attachment 106 in the installed position N. Furthermore, the stiffness of the at least one bias member 126 may maintain the first locking member 122 in the first position F and the second locking member 124 in the second position S to prevent removal of the attachment 106 from the bore 120. As such, the bias exerted by the at least one bias member 126 on the first and/or second locking member 122, 124 may at least partially exert the opposing axial force on the attachment 106. Said differently, the contact of the first and second locking members 122, 124 with the first and second attachment surfaces 108, 110, respectively, may exert the opposing axial force on the attachment 106 and be supplemented with additional force from the at least one bias member 126. On the other hand, the at least one bias member 126 may exert all of the opposing axial force on the first and second attachment surfaces 108, 110 to retain the attachment 106.

The at least one bias member 126 may be further defined as at least one compression spring, as shown in FIGS. 5-15 and 17-19. More specifically, the at least one bias member 126 may be configured as at least one helical spring. The at least one compression spring may extend along the axis A. The at least one compression spring may be radially spaced about the axis A such that the attachment 106 extends through the at least one compression spring along the axis A. In the example shown in FIGS. 5-10 and 17, the at least one bias member 126 is a single bias member 126 disposed between the first and second locking members 122, 124 and configured to bias the locking members 122, 124 away from one another. As such, the single bias member 126 extends to a pair of opposing ends, with one of the ends abutting the first locking member 122 and the other one of the ends abutting the second locking member 124. The single bias member 126 is sized to bias against both of the first and second locking members 122, 124. Movement of either of the first and second locking members 122, 124 toward one another must overcome the bias of the single bias member 126. However, it will be appreciated that the at least one bias member 126 may comprise any number of bias members 126 in any suitable configuration for biasing the first the first and second locking members 122, 124 in any suitable direction. For example, as shown in FIG. 18, the at least one bias member 126 is further defined as a pair of bias members 126, with one of the bias members 126 engaging and biasing the first locking member 122 and the other one of the bias members 126 engaging and biasing the second locking member 124. As shown in FIG. 18, the pair of bias members 126 may be spaced from one another. Each of the pair of bias members 126 bias their respective locking members 122, 124 in the same direction along the axis A to facilitate the exertion of the opposing axial forces on the attachment 106 when the attachment 106 is moved along the axis A from the installed position N to prevent removal of the attachment 106 from the bore 120. The biasing of the locking members 122, 124 in the same direction along the axis A will be better understood from the description presented below. However, the pair of bias members 126 may bias the locking members 122, 124 in opposite directions, transverse directions, or in any other suitable direction for facilitating the exertion of the opposing axial forces on the attachment 106 when the attachment 106 is moved along the axis A from the installed position N.

The housing 114 may comprise first and second housing surfaces 130, 132 spaced from one another and disposed at least partially within the bore 120. More specifically, in the examples shown in the Figures, the first and second housing surfaces 130, 132 are spaced from one another longitudinally along the axis A. However, the first and second housing surfaces 130, 132 may be spaced from one another in any suitable configuration within the bore 120. The first housing surface 130 may be proximate the first end 116 of the housing 114 and the second housing surface 132 may be proximate the second end 118 of the housing 114. The first and second housing surfaces 130, 132 may be disposed about the axis A. Moreover, the first and second housing surfaces 130, 132 may encircle the axis A within the bore 120 in an annular configuration about the axis A. The first and second housing surfaces 130, 132 may continuously encircle the axis A. On the other hand, the first and second housing surfaces 130, 132 may be segmented around the axis A. The first and second housing surfaces 130, 132 may be disposed in any suitable shape, size, and configuration within the bore 120.

As shown in FIGS. 5, 10, 17, and 18, the first housing surface 130 may be configured to be aligned with the first attachment surface 108 and the second housing surface 132 may be configured to be aligned with the second attachment surface 110 in the installed position N. Said differently, the first attachment and housing surfaces 108, 130 and the second attachment and housing surfaces 110, 132 may be proximate one another. More specifically, the first attachment and housing surfaces 108, 130 and the second attachment and housing surfaces 110, 132 may face one another orthogonal to the axis A. The first locking member 122 may be configured to contact both of the first attachment surface 108 and the first housing surface 130 in the first position F. Likewise, the second locking member 124 may be configured to contact both of the second attachment surface 110 and the second housing surface 132 in the second position S. Said differently, the first locking member 122 may be biased into contact with both of the first attachment and housing surfaces 108, 130 and the second locking member 124 may be biased into contact with both of the second attachment and housing surfaces 110, 132. As such, the first locking member 122 contacting both of the first attachment and housing surfaces 108, 130 provides rigid intermediate contact between the first attachment and housing surfaces 108, 130. Likewise, the second locking member 124 contacting both of the second attachment and housing surfaces 110, 132 provides rigid intermediate contact between the second attachment and housing surfaces 110, 132. Therefore, the first and second locking members 122, 124 facilitate a rigid connection between the attachment 106 and the housing 114. In doing so, the housing 114 exerts the opposing axial forces on the attachment 106 through the first and second locking members 122, 124 when the attachment 106 is moved along the axis A from the installed position N to prevent removal of the attachment 106 from the bore 120.

At least one of the first housing surface 130 and the first attachment surface 108 may be skewed relative to the axis A and at least one of the second housing surface 132 and the second attachment surface 110 may be skewed relative to the axis A to facilitate the opposing axial forces on the attachment 106. The term "skewed" commonly refers to a component that deviates from a straight line or a right angle. As such, the first attachment and housing surfaces 108, 130 and the second attachment and housing surfaces 110, 132 may deviate from a colinear, concentric, or parallel configuration relative to the axis A. The skewed configuration may be angular (i.e., straight), curved or a combination of both. Furthermore, the skewed configuration may be a combination of several different angular and/or curved surfaces. The skewed configurations position the surfaces 108, 110, 130, 132 transverse to the axis A, which allows the contact between the locking members 122, 124 and the surfaces 108, 110, 130, 132 to stop movement along the axis A. The skewed configurations of the housing surfaces 130, 132 facilitate the rigid connection between the housing 114 and the attachment 106.

In the example shown in FIGS. 5-17, both of the first and second housing surfaces 130, 132 are skewed relative to the axis A to facilitate the opposing axial forces on the attachment 106. As such, the housing 114 exerts the opposing axial forces on the attachment 106 through the first and second locking members 122, 124 when the attachment 106 is moved along the axis A from the installed position N to prevent removal of the attachment 106 from the bore 120. However, only one of the first and second housing surfaces 130, 132 may be skewed relative to the axis A, such as in the example shown in FIGS. 18-20. In that example, the first housing surface is skewed and exerts one of the opposing axial forces on the attachment 106 through the first locking member. The second housing surface is concentric with the axis A. In that example, the second housing surface does not exert the other one of the opposing axial forces. Instead, the stiffness of the bias member 126 biasing the second locking member into the second attachment surface is large enough to exert the other one of the opposing axial forces (as described above).

At least one of the first and second attachment surfaces 108, 110 may be skewed relative to the axis A to facilitate the opposing axial forces on the attachment 106. More specifically, in the examples shown in FIGS. 5-15, 17, and 18, each of the first and second attachment surfaces 108, 110 are skewed relative to the axis A to facilitate the opposing axial forces on the attachment 106. As such, the attachment 106 is configured to receive the opposing axial forces from the first and second locking members 122, 124 when the attachment 106 is moved along the axis A from the installed position N. The first and second attachment surfaces 108, 110 may face opposing directions along the axis A, with the first locking member 122 disposed along the axis A between the first attachment surface 108 and one of the first and second ends 116, 118 of the housing 114, and with the second locking member 124 configured to be disposed along the axis A between the second attachment surface 110 and the other one of the first and second ends 116, 118 of the housing 114. In the example shown in FIGS. 5-15 and 17, the first and second attachment surfaces 108, 110 are symmetric about a plane orthogonal to the axis. Moreover, the first and second attachment surfaces 108, 110 face away from one another. In the example shown in FIG. 18, the first and second attachment surfaces 108, 110 face toward one another. In either example, the first and second attachment surfaces 108, 110 face opposite directions along the axis A. As such, the first and second attachment surfaces 108, 110 provide retention of the attachment 106 in the direction along the axis A that the first and second attachment surfaces 108, 110 face. Because the first and second attachment surfaces 108, 110 face in opposing directions along the axis A, the surfaces 108, 110 provide retention along the axis A.

As shown in FIGS. 5-15, 17, and 18, the first attachment surface 108 may extend inwardly toward the axis A such that the first attachment surface 108 defines a first recess 134 configured to receive the first locking member 122 therein. Likewise, the second attachment surface 110 may extend inwardly toward the axis A such that the second attachment surface 110 defines a second recess 136 configured to receive the second locking member 124 therein, as shown in FIGS. 5-15 and 17. The first locking member 122 is disposed in the first recess 134 and the second locking member 124 is disposed in the second recess 136 when the attachment 106 is disposed in the installed position N. The disposition of the first and second locking members 122, 124 in the first and second recesses 134, 136 facilitates the opposing axial forces on the attachment 106, as will be better understood in the description below.

In another example, at least one of the first and second attachment surfaces 108, 110 extend outwardly away from the axis A. The outwardly extending first and/or second attachment surface 108, 110 encircles the attachment 106 around the axis A. More specifically, the second attachment surface 110 extends outwardly away from the axis A in the example shown in FIGS. 18-20. Said differently, the second attachment surface 110 may be configured as a ramp 138 that rises above the exterior surface of the attachment 106. The second locking member 124 is disposed on the second attachment surface 110 (above the exterior surface of the attachment 106) when the attachment 106 is disposed in the installed position N. The disposition of the second locking member 124 on the risen second attachment surface 110 facilitates the opposing axial forces on the attachment 106, as will be better understood in the description below. Moreover, it will be appreciated that the first attachment surface 108 may extend outwardly away from the axis A.

Figure 10:
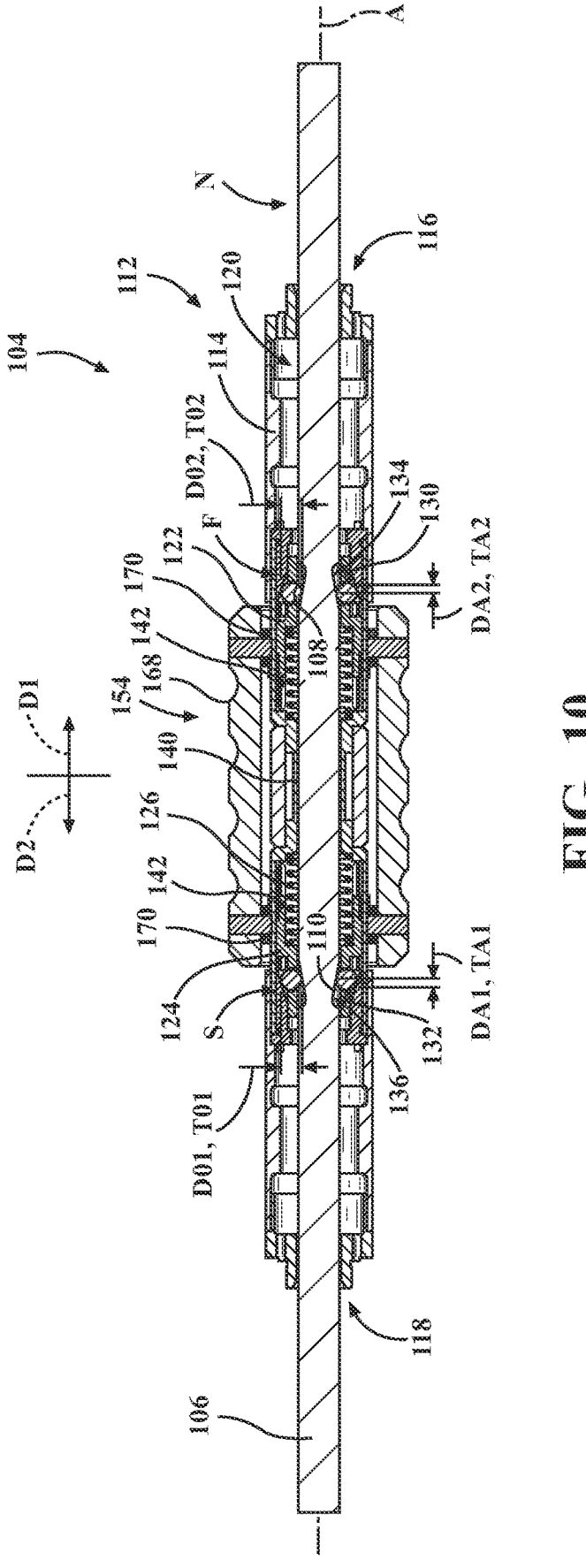
FIG. 10 is a cross-sectional view of the interlocking collet system shown in FIG. 4, taken along line 10-10.

As generally shown in FIG. 10, the first housing surface 130 and the first attachment surface 108 may define a first orthogonal distance DO1 therebetween perpendicular to the axis A. The second housing surface 132 and the second attachment surface 110 may define a second orthogonal distance DO2 therebetween perpendicular to the axis A. The skewed configuration of at least one of the first housing surface 130 and the first attachment surface 108 may facilitate a reduction in the first orthogonal distance DO1 when the attachment 106 moves from the installed position N in a first direction D1 along the axis A and wedges the first locking member 122 between the housing 114 and the attachment 106 to prevent removal of the attachment 106 from the bore 120 in the first direction D1. Similarly, the skewed configuration of at least one of the second housing surface 132 and the second attachment surface 110 may facilitate a reduction in the second orthogonal distance DO2 when the attachment 106 moves from the installed position N in a second direction D2 along the axis A, opposite the first direction D1, and wedges the second locking member 124 between the housing 114 and the attachment 106 to prevent removal of the attachment 106 from the bore 120 in the second direction D2.

More specifically, the first locking member 122 shown in the Figures has a substantially rigid construction that is resistant to compression. As such, the first locking member 122 has an orthogonal thickness TO1 that is defined between the first attachment and housing surfaces 108, 130 that is substantially constant, as generally shown in FIG. 10. With the attachment 106 disposed in the installed position N, and with the first locking member 122 disposed along the first attachment surface 108, the first orthogonal distance DO1 is greater than or equal to the orthogonal thickness TO1 of the first locking member 122. When the housing 114 is moved in the first direction D1, the first attachment surface 108 moves closer to the first housing surface 130. As such, the first orthogonal distance DO1 reduces. The first orthogonal distance DO1 attempts to become less than the orthogonal thickness TO1 of the first locking member 122. However, the rigidity of the first locking member 122 prevents further reduction in the first orthogonal distance DO1 (less than the orthogonal thickness TO1 of the first locking member 122). As such, the first locking member 122 prevents further movement of the attachment 106 in the first direction D1.

Likewise, the second locking member 124 shown in the Figures has a substantially rigid construction that is resistant to compression. As such, the second locking member 124 has an orthogonal thickness TO2 that is defined between the second attachment and housing surfaces 110, 132 that is substantially constant, as generally shown in FIG. 10. With the attachment 106 disposed in the installed position N, and with the second locking member 124 disposed along the second attachment surface 110, the second orthogonal distance DO2 is greater than or equal to the orthogonal thickness TO2 of the second locking member 124. When the housing 114 is moved in the second direction D2, the second attachment surface 110 moves closer to the second housing surface 132. As such, the second orthogonal distance DO2 reduces. The second orthogonal distance DO2 attempts to become less than the orthogonal thickness TO2 of the second locking member 124. However, the rigidity of the second locking member 124 prevents further reduction in the second orthogonal distance DO2 (less than the orthogonal thickness TO2 of the second locking member 124). As such, the second locking member 124 prevents further movement of the attachment 106 in the second direction D2.

Because both of the first housing surface 130 and the first attachment surface 108 are skewed relative to the axis A, the first housing surface 130 and the first attachment surface 108 define a first axial distance DA1 therebetween parallel to the axis A, as generally shown in FIG. 10. Likewise, because both of the second housing surface 132 and the second attachment surface 110 are skewed relative to the axis A, the second housing surface 132 and the second attachment surface 110 define a second axial distance DA2 therebetween parallel to the axis A. The skewed configuration of both of the first housing surface 130 and the first attachment surface 108 may facilitate a reduction in the first axial distance DA1 when the attachment 106 moves from the installed position N in the first direction D1 along the axis A and wedges the first locking member 122 between the housing 114 and the attachment 106 to prevent removal of the attachment 106 from the bore 120 in the first direction D1. Likewise, the skewed configuration of both of the second housing surface 132 and the second attachment surface 110 may facilitate a reduction in the second axial distance DA2 when the attachment 106 moves from the installed position N in the second direction D2 along the axis A and wedges the second locking member 124 between the housing 114 and the attachment 106 to prevent removal of the attachment 106 from the bore 120 in the second direction D2.

More specifically, the first locking member 122 has an axial thickness TA1 that is defined between the first attachment and housing surfaces 108, 130 that is substantially constant, as generally shown in FIG. 10. With the attachment 106 disposed in the installed position N, and with the first locking member 122 disposed along the first attachment surface 108, the first axial distance DA1 is greater than or equal to the axial thickness TA1 of the first locking member 122. When the housing 114 is moved in the first direction D1, the first attachment surface 108 moves closer to the first housing surface 130. As such, the first axial distance DA1 reduces. The first axial distance DA1 attempts to become less than the axial thickness TA1 of the first locking member 122. However, the rigidity of the first locking member 122 prevents further reduction in the first axial distance DA1 (less than the axial thickness TA1 of the first locking member 122). As such, the first locking member 122 prevents further movement of the attachment 106 in the first direction D1.

Likewise, the second locking member 124 has an axial thickness TA2 that is defined between the second attachment and housing surfaces 110, 132 that is substantially constant, as generally shown in FIG. 10. With the attachment 106 disposed in the installed position N, and with the second locking member 124 disposed along the second attachment surface 110, the second axial distance DA2 is greater than or equal to the axial thickness TA2 of the second locking member 124. When the housing 114 is moved in the second direction D2, the second attachment surface 110 moves closer to the second housing surface 132. As such, the second axial distance DA2 reduces. The second axial distance DA2 attempts to become less than the axial thickness TA2 of the second locking member 124. However, the rigidity of the second locking member 124 prevents further reduction in the second axial distance DA2 (less than the axial thickness TA2 of the second locking member 124). As such, the second locking member 124 prevents further movement of the attachment 106 in the second direction D2.

As shown in FIGS. 5-15, 17, and 18, the attachment 106 may comprise at least one attachment unlock surface 140 adjacent the first and second attachment surfaces 108, 110. Likewise, the housing 114 may comprise at least one housing unlock surface 142 adjacent the first and second housing surfaces 130, 132.

The first and second attachment surfaces 108, 110 may transition to the at least one attachment unlock surface 140. Said differently, the each of the first and second attachment surfaces 108, 110 are configured such that they converge with the at least one attachment unlock surface 140. As such, the first locking member 122 may move between the first attachment surface 108 and the at least one attachment unlock surface 140. Likewise, the second locking member 124 may move between the second attachment surface 110 and the at least one attachment unlock surface 140.

The first and second housing surfaces 130, 132 may transition to the at least one housing unlock surface 142. Said differently, the each of the first and second housing surfaces 130, 132 are configured such that they converge with the at least one housing unlock surface 142. As such, the first locking member 122 may move between the first housing surface 130 and the at least one housing unlock surface 142. Likewise, the second locking member 124 may move between the second housing surface 132 and the at least one housing unlock surface 142.

The attachment and housing unlock surfaces 140, 142 may be concentrically spaced from one another. Moreover, the attachment and housing unlock surfaces 140, 142 may be concentrically disposed around the axis A. As such, the attachment and housing unlock surfaces 140, 142 may be configured to dispose the first and second locking members 122, 124 therebetween to facilitate movement of the attachment, independent of the housing 114, along the axis A. Said differently, each of the first and second locking members 122, 124 may be configured to be selectively disposed along the attachment and housing unlock surfaces 140, 142 to facilitate movement of the attachment 106, independent of the housing 114, along the axis A. As such, the at least one attachment unlock surface 140 and the at least one housing unlock surface 142 define a gap 144 therebetween. The first and second locking members 122, 124 are configured and sized to be completely disposed within the gap 144. More specifically, the first locking member 122 may be moved away from the first attachment surface 108 (against the bias of the at least one bias member 126) and into the gap 144. Likewise, the second locking member 124 may be moved away from the second attachment surface 110 (against the bias of the at least one bias member 126) and into the gap 144. The disposition of either of first and/or second locking members 122, 124 in the gap 144 allows for movement of the attachment 106 along the axis A. More specifically, the displacement of either of the first and second locking members 122, 124 in the gap 144 eliminates the contact of the first and/or second locking (which exert the opposing axial forces on the attachment 106). Eliminating one or both of the opposing axial forces on the attachment 106 creates an unbalanced force, or no force, on the attachment 106. As such, the attachment 106 may move along the axis A. The movement of the attachment 106 along the axis A when the first and/or second locking member 124 is disposed in the gap 144 will be described in greater detail below.

The at least one attachment unlock surface 140 may be disposed between the first and second attachment surfaces 108, 110 and the at least one housing unlock surface 142 may be disposed between the first and second housing surfaces 130, 132, as shown in FIGS. 5-15 and 17. In this example, the at least one attachment unlock surface 140 is further defined as a single attachment unlock surface 140, with the first and second locking members 122, 124 configured to interact with the singled attachment unlock surface 140. On the other hand, the at least one housing unlock surface 142 is further defined as a pair of housing unlock surfaces 142 spaced from one another along the axis A, with the first locking member 122 configured to interact with one the pair of housing unlock surfaces 142 and the second locking member 124 configured to interact with the other one of the pair housing unlock surfaces 142. However, the at least one attachment unlock surface 140 and the at least one housing unlock surface 142 may comprise any suitable number of surfaces to interact with the first and second locking members 122, 124. In the example shown in FIG. 18, at least one attachment unlock surface 140 is further defined as a pair of attachment unlock surfaces 140 spaced from one another along the axis A, and the at least one housing unlock surface 142 is further defined as a pair of housing unlock surfaces 142 spaced from one another along the axis A. The first locking member 122 is configured to interact with one of the pair of attachment unlock surfaces 140 and one the pair of housing unlock surfaces 142. The second locking member 124 configured to interact with the other one of the pair of attachment unlock surfaces 140 and the other one of the pair housing unlock surfaces 142.

In the example shown in FIG. 5 each of the first and second locking members 122, 124 comprise a frame 146 and a plurality of spheres 148 retained by the frame 146 and radially disposed around the axis A, with each of the spheres 148 being movable, relative to the frame 146, transverse to the axis A. Each of the frames 146 has a generally tubular configuration extending along the axis A and configured to receive the attachment 106 therethrough. Each of the frames 146 may have a shoulder 150 transverse to the axis A and configured to engage the at least one bias member 126. The at least one bias member 126 engages and biases each of the frames 146 through the engagement with the shoulder 150.

Each of the frames 146 may define a plurality of apertures 152 radially spaced about the axis A. The apertures 152 extend orthogonal to the axis A. However, the apertures 152 may be arranged in any suitable configuration. Each of the apertures 152 are configured to receive one of the plurality of spheres 148 therein. Moreover, each of the apertures 152 are sized and shaped to retain one of the plurality of spheres 148 along the axis A. However, because each of the apertures 152 extends orthogonal to the axis A, each of the spheres 148 may move orthogonal to the axis A (i.e., along the longitudinal axis of each of the apertures 152). As such, the spheres 148 are configured to move "up and down" within the apertures 152 such that the spheres 148 ride along the surfaces of the attachment 106 and/or the housing 114 as the first and second locking members 122, 124 move along the axis A. Moreover, because the spheres 148 may move orthogonal to the axis A, the spheres 148 may move along the skewed first and second attachment surfaces 108, 110 and/or the skewed first and second housing surfaces 130, 132, without requiring movement of the frames 146 orthogonal to the axis A.

The first and/or second locking member 122, 124, that respectively correspond with the outwardly extending first and/or second attachment surface 108, 110, may have an annular configuration around the axis A and define an inner diameter ID. The outwardly extending first and/or second attachment surface 108, 110 may have an outer diameter OD that increases as the surfaces 108, 110 extend further from the axis A such that first and/or second locking member 122, 124 moves up the first and/or second attachment surface 108, 110 until the inner and outer diameters ID, OD equal one another. More specifically, in the example shown in FIGS. 18-20, the second locking member 124 has the annular configuration and is configured to move up the second attachment surface 110 when the attachment 106 moves in the second direction (i.e., toward the end effector 22). The second locking member 124 has a substantially rigid configuration. The second locking member 124 has the inner diameter ID. As the attachment 106 is inserted into the housing 114/nose tube 214, a member disposed on the OD of the shaft of the attachment 106 may contact the distal portion of the second locking member 124, 224. The member disposed on the OD of the shaft of the attachment 106 is sized to be slightly larger than the ID of the second locking member 124. As the attachment 106 is inserted into the housing 114/nose tube 214, the member on the attachment contacts the second locking member 124, 224, urging the distal portion of the second locking member 124, 224 in the proximal direction. Because of the taper of the shaft of the attachment 106, as the second locking member 124, 224 travels proximally up the shaft of the attachment 106, the second locking member 124, 224 tightens on the OD of the shaft of the attachment 106 to contact the second attachment surface 110 and assist in securing the attachment to the end effector 22. The second locking member 124 is configured to move up the second attachment surface 110 until the inner and outer diameters ID, OD equal one another. As such, the entire second locking member 124 is configured to ride along the surfaces of the attachment 106.

In the example shown in FIGS. 18-20, the second locking member 124 is configured as a bearing. As commonly known in the art, a bearing is configured to facilitate rotation between two adjacent components. In this example, the bearing configuration of the second locking member 124 facilitates rotation of the attachment 106 about the axis A, relative to the housing 114 (i.e., rotation of the tool 20 of the end effector 22). However, the second locking member 124 shown in FIGS. 18-20 may have any suitable configuration for contacting the second attachment surface 110.

Figures 21, 22, 23:
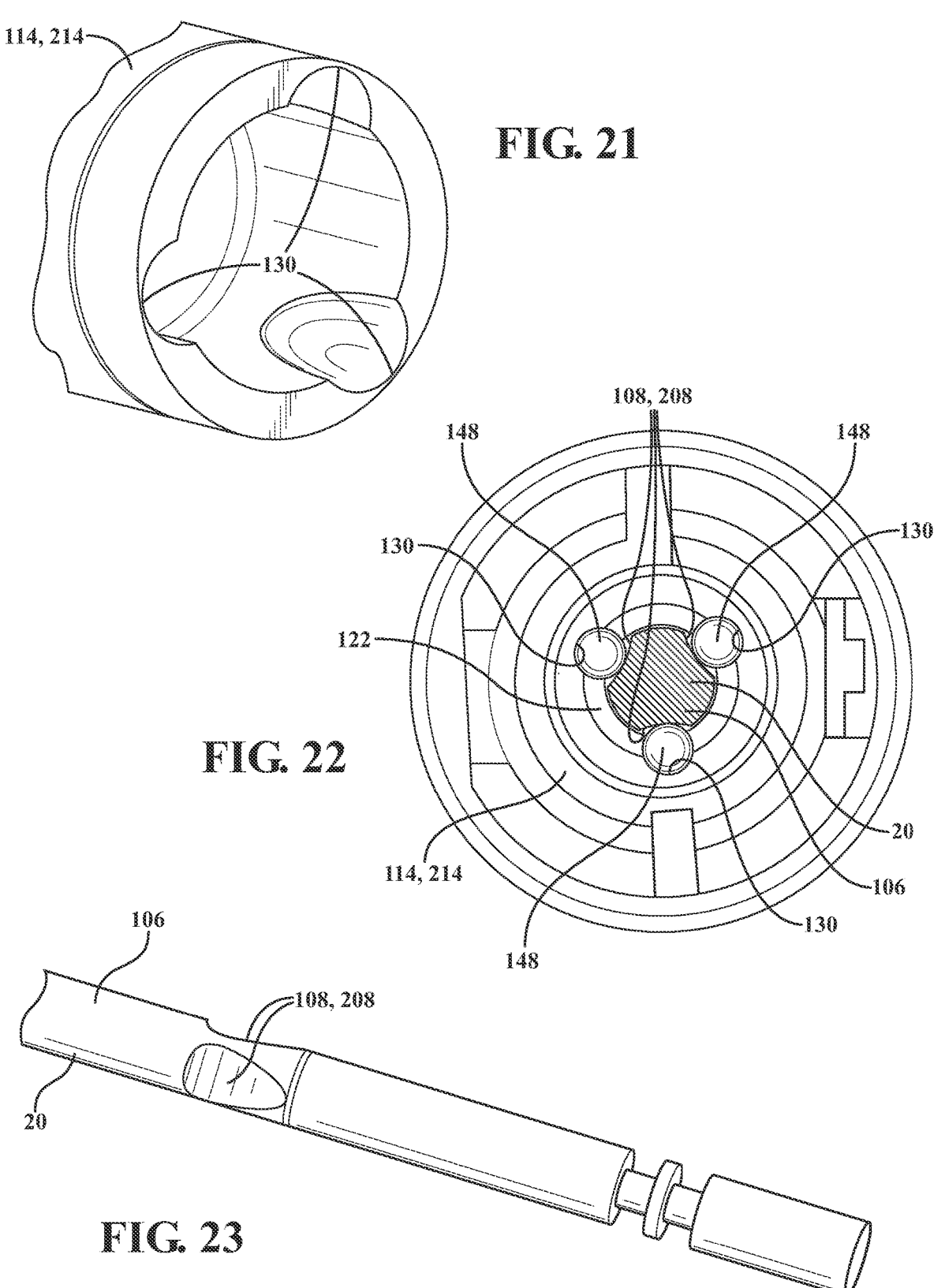
FIG. 21 is a sectional view of the housing of the interlocking collet system of FIG. 18, showing a plurality of first housing surfaces.
FIG. 22 is a cross-sectional view of the end effector of FIG. 18, taken along line 22-22 and showing the first locking member between the housing and the attachment.
FIG. 23 is a perspective view of the attachment of the interlocking collet system of FIG. 18, showing a plurality of first attachment surfaces.

As described above, FIGS. 18-24 show the attachment 106 being configured to rotate about the axis A, relative to the collet 112. More specifically, as shown in FIGS. 21 and 22, the first housing surface 130 may be further defined as a plurality of first housing surfaces 130 radially spaced about the axis A. Likewise, as shown in FIGS. 22 and 23, the first attachment surface 108 may be further defined as a plurality of first attachment surfaces 108 radially spaced about the axis A. The plurality of spheres 148 of the first locking member 122 are configured such that a single sphere 148 is disposed between a single first housing surface 130 and a single first attachment surface 108 for each of the plurality of first housing surfaces 130 and the plurality of first attachment surfaces 108. As shown in FIG. 22, the first housing surfaces 130 have a generally curved configuration across the housing 114 while the first attachment surfaces 108 have generally linear configuration across the attachment 106. The shapes of the first housing surfaces 130 and the first attachment surfaces 108 facilitate wedging of the spheres 148 between the housing 114 and the attachment 106 when the housing 114 and the attachment 106 rotate independent of one another about the axis A. As such, the first locking member is configured as a rotational clutch between the housing 114 and the attachment 106 in the example shown in FIGS. 18-24. Accordingly, the end effector 22 may be configured to rotate the housing 114 about the axis A. When the attachment 106 is disposed in the attached position N (as shown in FIG. 18), the housing 114 is configured to drive the attachment 106 rotatably about the axis A. Said differently, the spheres 148 are configured to drive rotation of the attachment 106/tool 20 about the axis A when the housing 114 is rotated (e.g., by an electric motor). As such, the spheres 148 transmit torque to the attachment 106/tool 20 that, when in contact with the target site (as mentioned above), may facilitate the removal of tissue. However, the end effector 22 may be configured to rotate the attachment 106 in any other suitable way, including independent of the housing 114.

Figures 11, 12:
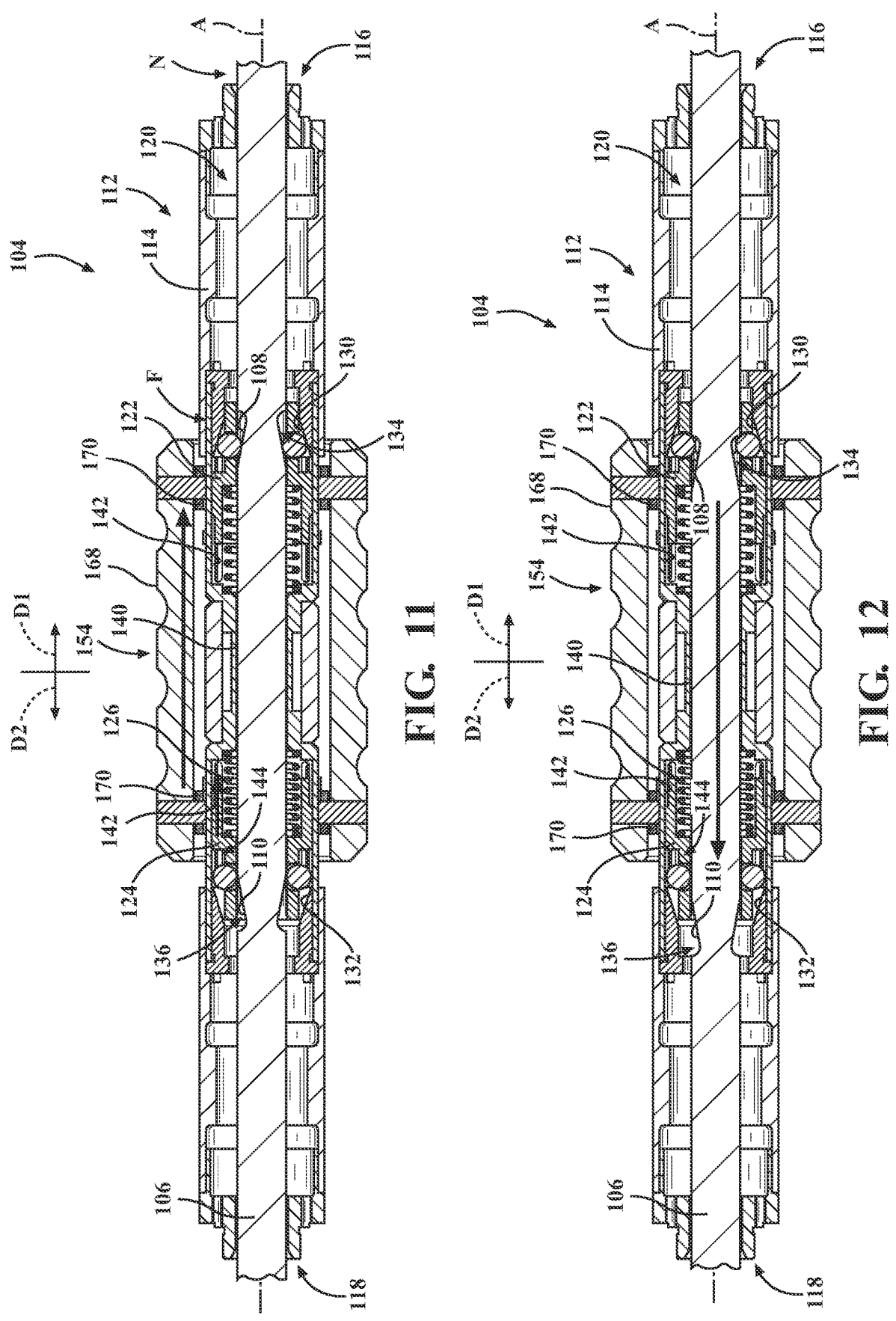
FIG. 11 is a cross-sectional view of the interlocking collet system, showing the attachment disposed in the installed position and the slide moving the second locking member in the first direction along the axis.
FIG. 12 is a cross-sectional view of the interlocking collet system, showing the attachment moving in the second direction along the axis.

As shown in FIGS. 2-4, the collet 112 may further comprise a slide 154 disposed along the housing 114 and movable along the axis A. The slide 154 is configured to engage and move the first and second locking members 122, 124 along the axis A against the bias of the bias member 126. More specifically, the slide 154 is configured to engage and move the first locking member 122 along the axis A away from the first attachment surface 108 and into the gap 144 between the attachment unlock surface 140 and the housing unlock surface 142 (i.e., remove the first locking member 122 from contact with the first attachment surface 108 and or the first housing surface 130). Likewise, the slide 154 is configured to engage and move the second locking member 124 along the axis A away from the second attachment surface 110 and into the gap 144 between the attachment unlock surface 140 and the housing unlock surface 142 (i.e., remove the second locking member 124 from contact with the second attachment surface 110 and or the second housing surface 132). As mentioned above, moving either of the first and second locking members 122, 124 into the gap 144 will facilitate movement of the attachment 106 along the axis A and disassembly of the attachment 106 from the collet 112. More specifically, when the second locking member 124 is moved in the first direction and into the gap 144 (as shown in FIG. 11), the attachment 106 may move in the second direction (as shown in FIG. 12). When the first locking member 124 is moved in the second direction and into the gap 144, the attachment 106 may move in the first direction. As such, the slide 154 facilitates bidirectional disassembly of the attachment 106 from the collet 112 in the example shown in FIGS. 2-17.

As shown in FIG. 3, the housing 114 may define at least one slot 156 extending longitudinally along the axis A and opening into the bore 120 and an exterior 158 of the housing 114. Each of the first and second locking members 122, 124 may comprise a projection 160 extending through the at least one slot 156 and disposed in the exterior 158. The slide 154 may be configured to engage the projections 160 to move the first and second locking members 122, 124 along the axis A against the bias of the bias member 126. The longitudinal extension of the at least one slot 156 allows the projection 160 (and the corresponding first and/or second locking member 122, 124) to move along the axis A within the slot 156. In the example shown in FIG. 3, each of the first and second locking members 122, 124 include three projections 160 radially spaced about the axis A. Moreover, the housing 114 defines six slots 156 individually corresponding with the projections 160 of the first and second locking members 122, 124. However, the housing 114 may comprise any suitable number of slots 156 and the first and second locking members 122, 124 may comprise any suitable number of projections 160 that facilitate movement of the first and second locking members 122, 124 along the axis A.

In the example shown in FIGS. 5-15 and 17, the at least one bias member 126 biases the first and second locking members 122, 124 away from one another. The slide 154 defines first and second abutment surfaces 162, 164 spaced from and facing one another along the axis A. The projections 160 of the first and second locking members 122, 124 are disposed between the abutment surfaces. The first abutment surface 162 is configured to engage and move the projection 160 of the first locking member 122 when the slide 154 moves in one direction along the axis A. The second abutment surface 164 is configured to engage and move the projection 160 of the second locking member 124 when the slide 154 moves in another direction along the axis A.

More specifically, as illustrated in FIGS. 11-15, when the slide 154 moves in the first direction, the second abutment surface 164 engages the projection 160 of the second locking member 124 and moves the projection 160 within the slot 156. Moreover, the second locking member 124 moves in the first direction against the bias of the bias member 126. Movement of the slide 154 in the first direction spaces the first abutment surface 162 further from the projection 160 of the first locking member 122. As such, movement of the slide 154 in the first direction moves the second locking member 124, but not the first locking member 122. The first locking member 122 remains adjacent the first attachment surface 108. Movement of the slide 154 allows in the first direction allows the attachment 106 to move in the second direction to remove the attachment 106 from the bore 120 of the housing 114.

When the slide 154 moves in the second direction, the first abutment surface 162 engages the projection 160 of the first locking member 122 and moves the projection 160 within the slot 156. Moreover, the first locking member 122 moves in the second direction against the bias of the bias member 126. Movement of the slide 154 in the second direction spaces the second abutment surface 164 further from the projection 160 of the second locking member 124. As such, movement of the slide 154 in the second direction moves the first locking member 122, but not the second locking member 124. The second locking member 124 remains adjacent the second attachment surface 110. Movement of the slide 154 allows in the second direction allows the attachment 106 to move in the first direction to remove the attachment 106 from the bore 120 of the housing 114.

As such, the slot 156 and the projection 160 facilitate movement of the first locking member 122 by the slide 154 along the axis A in a single direction. Likewise, the slot 156 and the projection 160 facilitates movement of the second locking member 124 by the slide 154 along the axis A in a single direction. However, in other configurations the slots 156 and projections 160 may facilitate movement of the first and second locking directions in more than one direction. Moreover, in the examples shown herein the first and second locking members 122, 124 contact the slide 154 when the slide 154 is moved in a certain direction. It is to be appreciated that the first and second locking members 122, 124 may be in continuous contact with the slide 154.

As shown in FIG. 3, the slide 154 may comprise an external surface 166 configured to be grasped by a user. As such, the user may actuate the slide 154 to facilitate disassembly of the attachment 106 from the collet 112. More specifically, the slide 154 may comprise a grip 168 comprising the external surface 166 and configured to be gripped by the user. The slide 154 may further comprise at least one ring 170 disposed around the housing 114 and the axis A and configured to engage at least one of the projections 160. In the example shown in FIG. 3, the at least one ring 170 is further defined as a pair of rings 170 spaced from one another along the axis A and mounted to the grip 168 such that the rings 170 move with the grip 168 along the axis A. One of the pair of rings 170 comprises the first abutment surface 162 while the other one of the pair of rings 170 comprises the second abutment surface 164. The projections 160 of the first and second locking members 122, 124 are disposed between the pair of rings 170.

Figure 24:
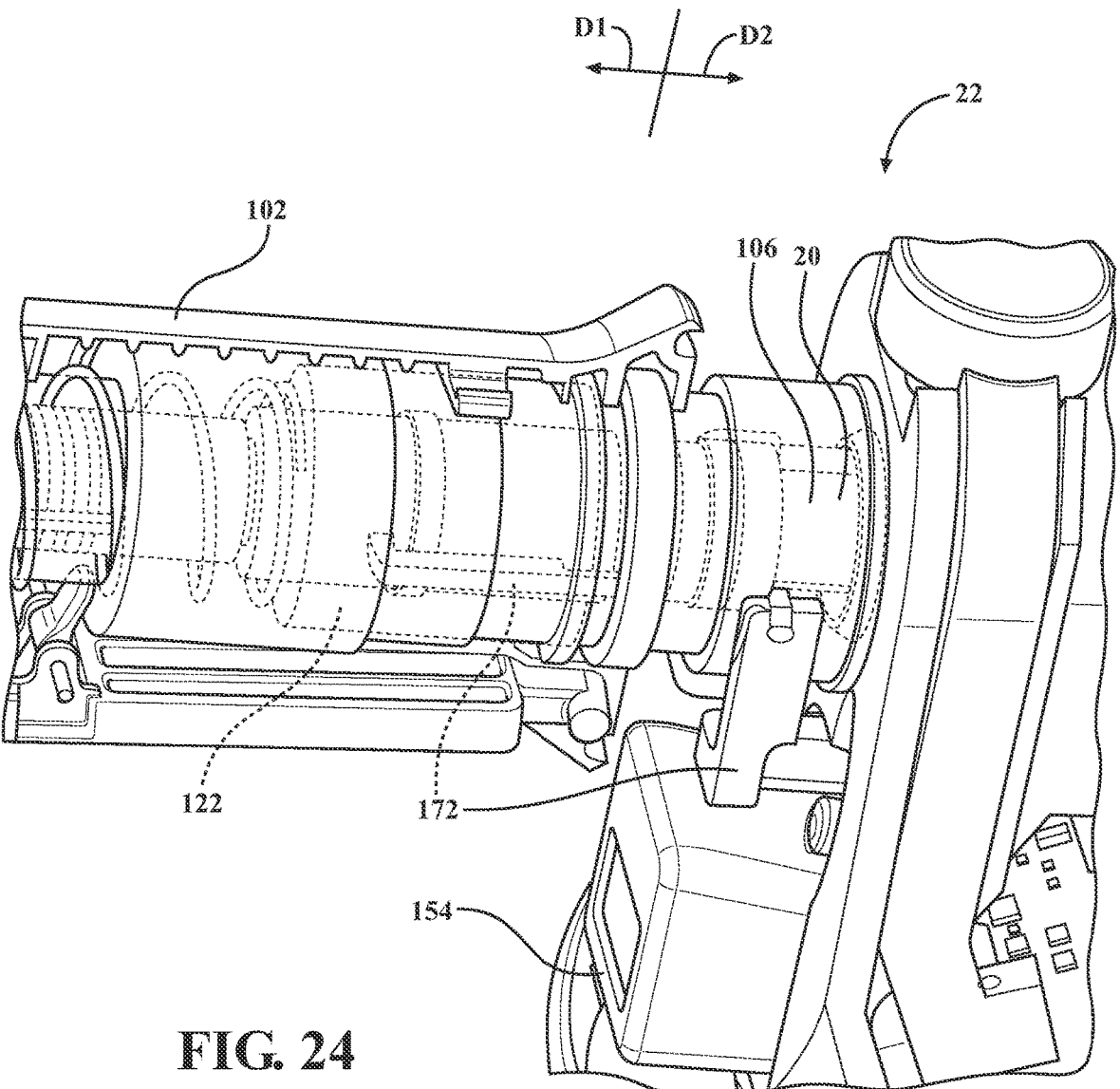
FIG. 24 is a perspective view of the end effector of FIG. 18, showing a slide for moving the first locking member.
Figure 25:
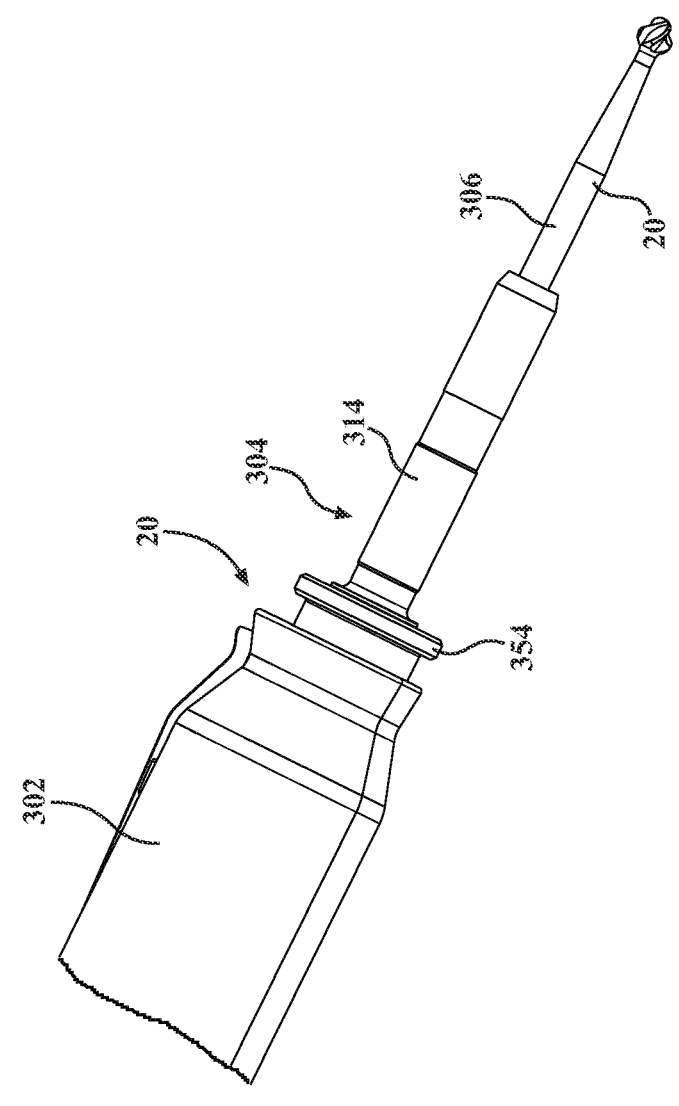
FIG. 25 is a perspective view of another example of an end effector for use with the robotic system shown in FIG. 1, including a handle and an exemplary configuration of an interlocking collet system for removably securing an attachment to the handle of the end effector.

In the example show in FIG. 24, the slide 154 is configured as a button spaced from the collet 112 and configured to be pressed by the user in a direction parallel to the axis A. A plurality of linkages 172 are couple the slide 154 with the first locking member 122. When the slide 154 is pressed, the linkages 172 move the first locking member 122 in the second direction D2 to space the first locking member 122 from each of the first housing surface 130 and the first attachment surface 108 and facilitate removal of the attachment 106 from the housing 114 in the first direction D1.

The operation of inserting the attachment 106 into (and coupling with) the collet 112 in the example shown in FIGS. 6-15 will be discussed below for illustrative purposes only.

Figures 6, 7:
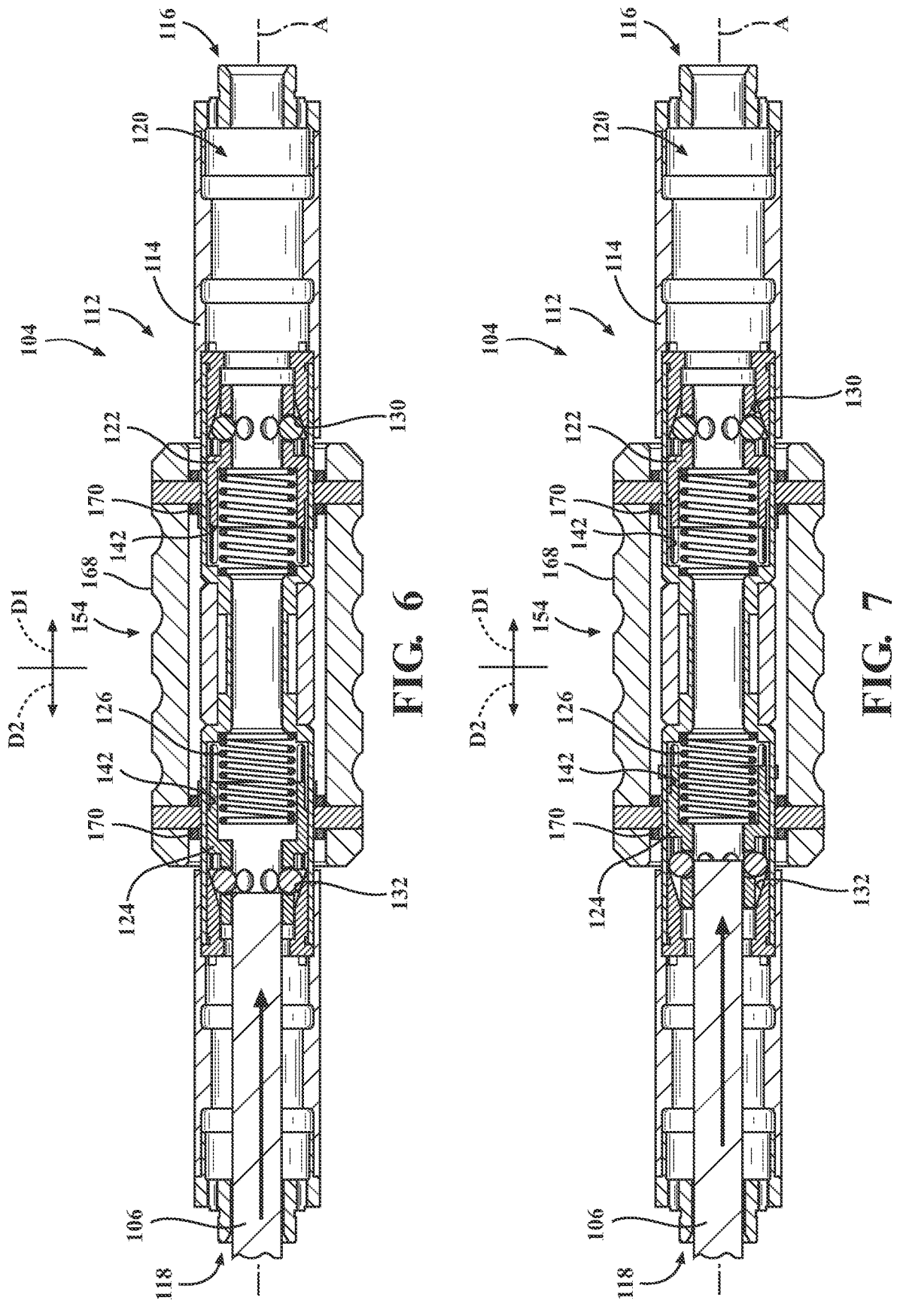
FIG. 6 is a cross-sectional view of the interlocking collet system, showing the attachment entering a bore of a housing at a second end.
FIG. 7 is a cross-sectional view of the interlocking collet system, showing the attachment moving a second locking member along the axis in a first direction.
Figures 8, 9:
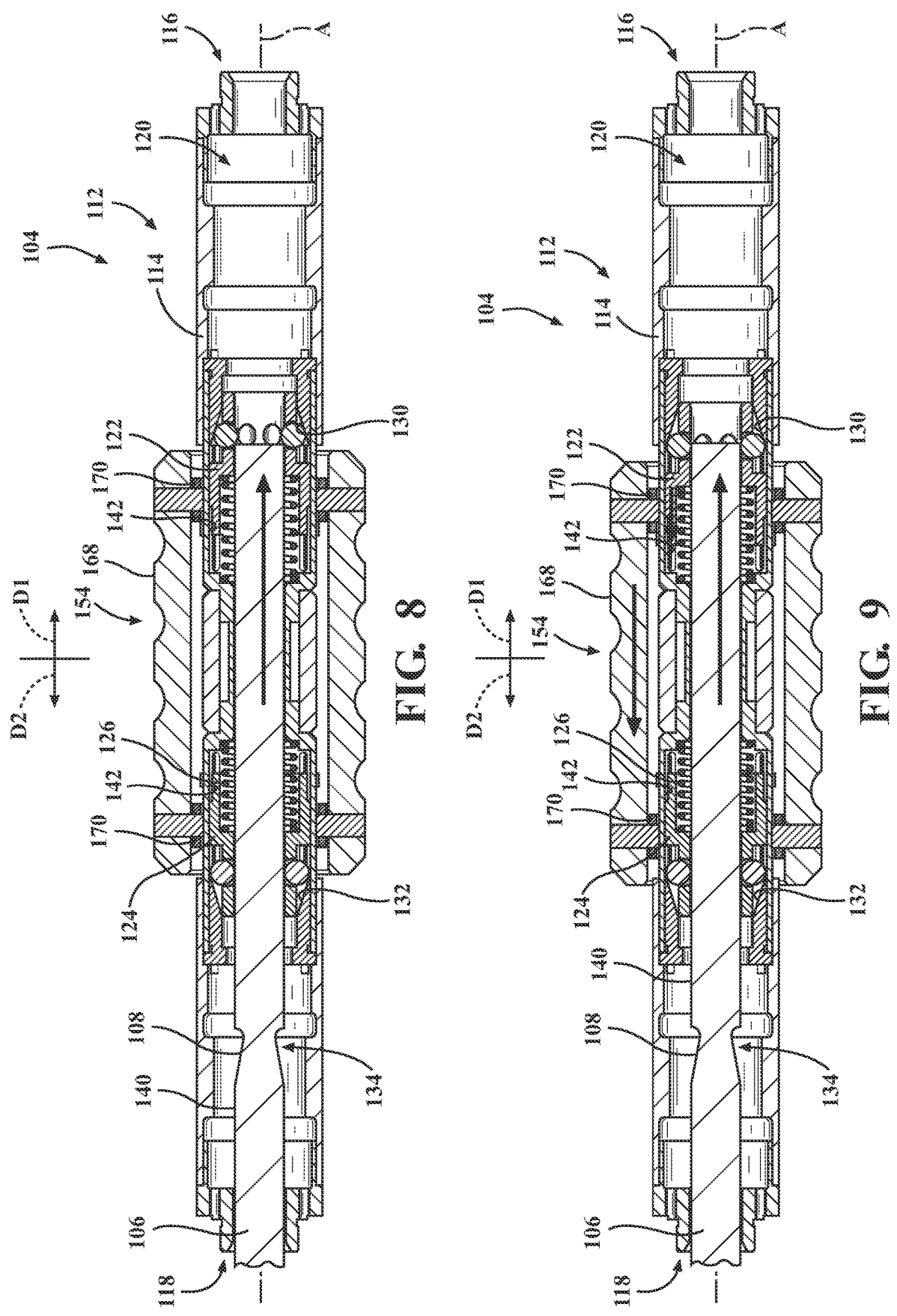
FIG. 8 is a cross-sectional view of the interlocking collet system, showing the attachment engaging a first locking member along the axis.
FIG. 9 is a cross-sectional view of the interlocking collet system, showing the slide moving the first locking member in a second direction along the axis.

As shown in FIG. 6, the attachment 106 enters the bore 120 at the second end 118 of the housing 114. The attachment 106 moves within the bore 120 toward the first end 116 of housing 114. As shown in FIG. 7, the attachment 106 contacts the spheres 148 of the second locking member 124. The force exerted by the attachment 106 along the axis A pushes the spheres 148 (moreover, the entire second locking member 124) along the second housing surface 132 to the housing unlock surface 142. When the spheres 148 of the second locking member 124 are disposed along the housing unlock surface 142, the spheres 148 roll along the attachment 106 as the attachment 106 continues to move in the first direction toward the first end 116, as shown in FIG. 8. The spheres 148 are maintained along the housing unlock surface 142.

The attachment 106 continues to move in the first direction until the attachment 106 contacts the spheres 148 of the first locking member 122. Further movement of the attachment 106 in the first direction urges the spheres 148 into the first housing surface 130. As such, the user grasps and moves the slide 154 in the second direction, as shown in FIG. 9. Movement of the slide 154 in the second direction moves the spheres 148 of the first locking member 122 along the first housing surface 130 to the housing unlock surface 142. When the spheres 148 of the first locking member 122 are disposed along the housing unlock surface 142, the spheres 148 roll along the attachment 106 as the attachment 106 continues to move in the first direction toward the first end 116, as shown in FIG. 9. With the spheres 148 maintained along the housing unlock surface 142, the slide 154 may be released.

The attachment 106 continues to move in the first direction until the first attachment surface 108 aligns with the first housing surface 130, and the second attachment surface 110 aligns with the second housing surface 132, as shown in FIG. 10. Said differently, the attachment 106 moves in the first direction until the attachment 106 is disposed in the installed position N. The bias of the bias member 126 urges the first and second locking members 122, 124 away from one another. The spheres 148 of the first locking member 122 move toward the axis A and are disposed between the first attachment surface 108 and the first housing surface 130. The spheres 148 of the second locking member 124 move toward the axis A and are disposed between the second attachment surface 110 and the second housing surface 132. The first and second locking members 122, 124 retain the attachment 106 in the installed position N.

In addition, the operation of removing the attachment 106 and the collet 112 in the example shown in FIGS. 11-15 will be discussed below for illustrative purposes only.

To remove the attachment 106 from the collet 112 in the second direction out of the bore 120 at the second end 118 of the housing 114, the user grasps and moves the slide 154 in the first direction, as shown in FIG. 11. Movement of the slide 154 in the first direction moves the spheres 148 of the second locking member 124 along the second housing surface 132 to the housing unlock surface 142 and along the second attachment surface 110 to the attachment unlock surface 140. When the spheres 148 of the first locking member 122 are disposed along the housing unlock surface 142, the spheres 148 roll along the attachment 106 as the attachment 106 moves in the second direction toward the second end 118, as shown in FIG. 12.

Figures 13, 14:
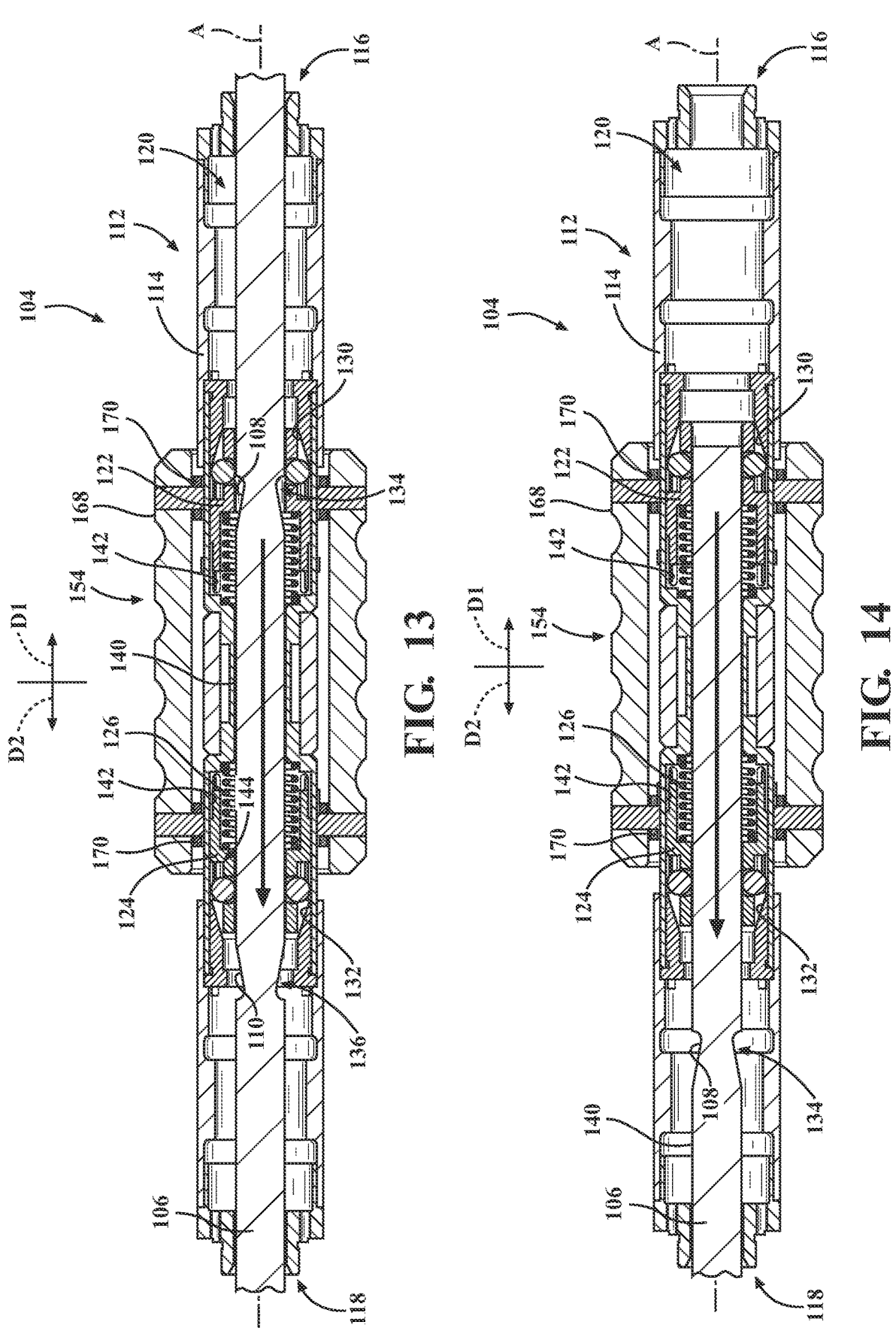
FIG. 13 is a cross-sectional view of the interlocking collet system, showing the attachment moving the first locking member along the axis in the second direction.
FIG. 14 is a cross-sectional view of the interlocking collet system, showing moving the attachment along the axis in the second direction.
Figure 15:
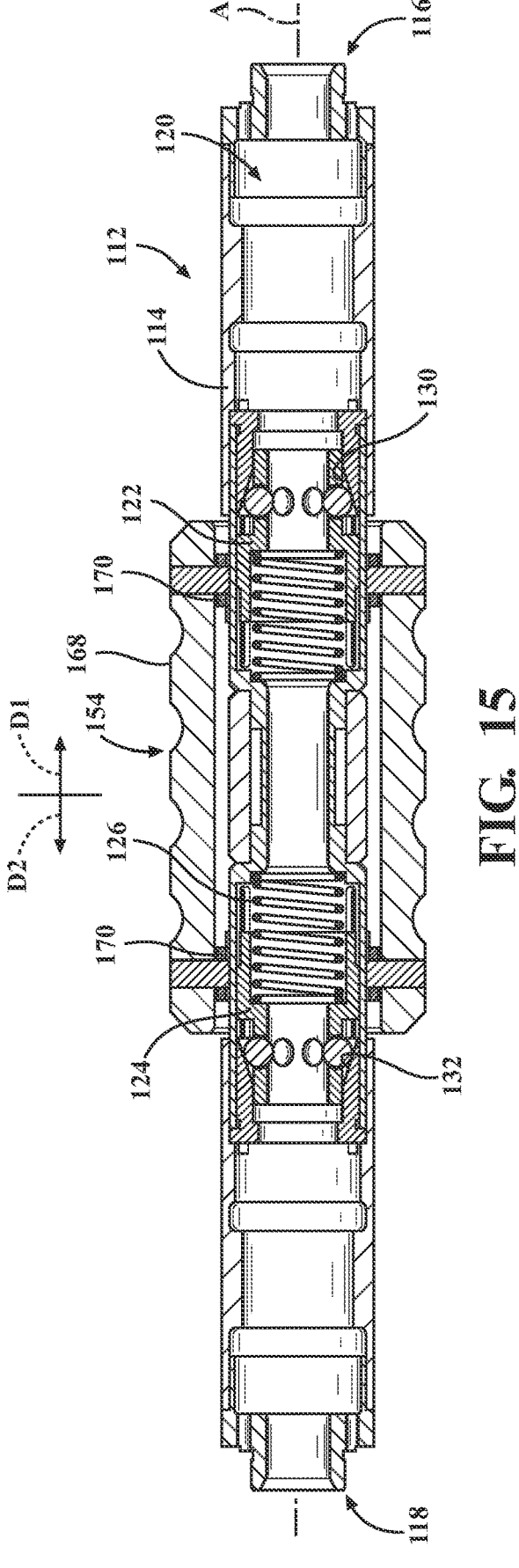
FIG. 15 is a cross-sectional view of the collet of the interlocking collet system, with the attachment removed from the bore of the housing.

As shown in FIG. 13, the attachment 106 moves within the bore 120 toward the second end 118 of housing 114. The attachment 106 contacts the spheres 148 of the first locking member 122. The force exerted by the attachment 106 along the axis A pushes the spheres 148 (moreover, the entire first locking member 122) along the first housing surface 130 to the housing unlock surface 142. When the spheres 148 of the first locking member 122 are disposed along the housing unlock surface 142, the spheres 148 roll along the attachment 106 as the attachment 106 continues to move in the second direction toward the second end 118, as shown in FIG. 14. The spheres 148 are maintained along the housing unlock surface 142. The attachment 106 continues to move in the second direction along the axis A until the attachment 106 is removed from the second end 118 of the housing 114, as shown in FIG. 15.

Although the operation above describes inserting the attachment 106 into the bore 120 at the second end 118 of the housing 114 and the subsequent coupling of the attachment 106 to the collet 112, the attachment 106 may also be inserted into the bore 120 at the first end 116 to couple the attachment 106 with the collet 112. When inserted into the first end 116, the operation described above is mirrored between the "first" and "second" components. Furthermore, although the operation above describes removing the attachment 106 from the bore 120 at the second end 118 of the housing 114, the attachment 106 may also be removed from the bore 120 at the first end 116. When removed from the bore 120 at the first end 116, the operation described above is mirrored between the "first" and "second" components.

III. Alternative Configuration of Interlocking Collet System

Similar to the interlocking collet system 104 described above, where the locking members are a part of the housing 114 and or nose tube 214, and the attachment includes the locking surfaces, it is also contemplated that the collet itself may include the locking surfaces to allow the housing 114 and/or nose tube 214 to be separated from the slider 154. In this configuration, the housing 314, 414, as will be described in greater detail below may be fixed to the attachment 106, 306, such that the housing 314, 414 of the collet 312, 412 may be configured to removably secure the attachment to the slider 354, 454, and by extension the attachment 306 or the surgical tool 22 to the end effector 20.

Referring to the Figures, wherein like numerals indicate like or corresponding parts throughout the several views, an exemplary interlocking collet system 304 is generally shown in FIGS. 25-30. The interlocking collet system 304 may be configured to receive an attachment 306, similar to those described in more detail above. The interlocking collet system may also comprise a collet 312 defining an attachment surface(s) 310A, 310B spaced from one another along the collet 312 for selectively retaining the attachment 306. Similar to as described above, the interlocking collet system 304 may be utilized with the system 10, and more specifically, for retaining the surgical tool 22 to the end effector 20. However, the interlocking collet system 304 may also be utilized for other types of surgical components other than the surgical tool 22 and end effector 20.

As shown in FIGS. 25-30, the collet 312 comprises a housing 314 configured to extend along an axis A between first and second ends 316, 318. The housing 314 defines a bore 320 along the axis A for selectively disposing and retaining the attachment 306 therein in an installed position N. The collet 312 further comprises locking members 324 disposed within the bore 320 of the housing 314 and each being moveable along the axis A.

Figure 26:
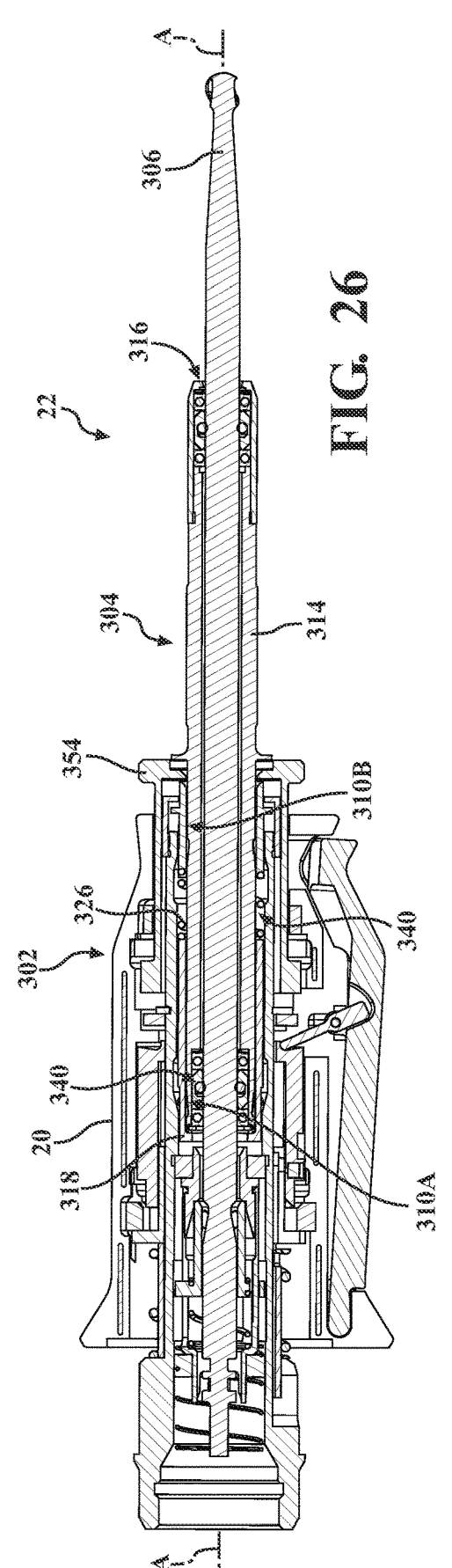
FIG. 26 is a sectional view of the end effector of FIG. 31.

The collet 312 further comprises at least one bias member 326 disposed within the bore 320 of the housing 314. The least one bias member 326 is arranged to position the locking member 324 along the axis A in a first position F in which the locking member 324 is configured to contact the first attachment surface 308 of the attachment 306, as shown in FIGS. 26 and 30. Moreover, the at least one bias member 326 is arranged to position the locking member 324 along the axis A in a second position S in which the locking member 324 is configured to contact the attachment surface(s) 310 of the attachment 306. The locking members 324 in the first and second positions F, S, respectively, are configured to exert opposing axial forces on the housing 314 of the collet 312.

The opposing axial forces, exerted on the housing 314 by the locking members 324, act along the axis A. As such, movement of the housing 314 in one direction along the axis A causes one of the locking members 324 to exert one of the opposing axial forces on the housing 314. Similarly, movement of housing 314 and/or the attachment 106 in another (opposite) direction along the axis A causes the other one of the locking members 324 to exert the other one of the opposing axial forces on the housing 314. As such, the opposing axial forces exerted by the locking members 324 may provide the advantage of symmetrically retaining the housing 314 and the attachment 106 along the axis A.

Devices using a single locking mechanism are susceptible to producing a bending moment on an attachment when a lateral load (i.e., transverse to the longitudinal axis of the attachment) is exerted on the attachment. The utilization of the multiple arrangements of locking members 324, as described herein, provides the benefit of resisting bending moments on the housing 314, and by extension the attachment 306, when a lateral load is exerted on the housing 314 and/or attachment 306. The locking members 324 distribute the load along the housing 314, rather than exerting the load on a single point (as is the case with collets with single locking mechanisms). By distributing the load, the deflection of the housing 314 and the attachment 106 along the axis A is reduced. In some examples, the attachment 306 is rotated about the axis A (e.g., when incorporated in the end effector 22, as described above). Deflection of the housing 314 and/or the attachment 306 can cause sudden, unintended, changes in the angular velocity of the attachment 306 (i.e., slip). When used with the end effector 22, uniform angular velocity provides benefits, such as, efficient and uniform removal of material (i.e., when the attachment 306 is configured as the tool 20) and cooler cutting temperatures.

The collet 312 may further comprise a slide 354 configured to receive the housing 314 and being movable along the axis A. The slide 354 is configured to engage and move the locking members 324 along the axis A against the bias of the bias member 326. More specifically, the slide 354 is configured to engage and move the locking member(s) 324 along the axis A away from the attachment surface 310 and into a gap 340 between unlock surface of the slider 354 and the housing 314 (i.e., remove the locking member 324 from contact with the attachment surface 310A of the housing 314). Likewise, the slide 354 is configured to engage and move the locking member 324 along the axis A away from the attachment surface 310B and into the gap 340 between the attachment unlock surface and the housing unlock surface 142 (i.e., remove the locking member 324 from contact with the attachment surface 310B of the housing 314). As mentioned above, moving either of the locking members 324 into the gap 340 will facilitate movement of the housing 314, and by extension the attachment 306 along the axis A and disassembly of the housing 314 and the attachment 306 from the slider 354 of the collet 312. More specifically, when the locking member 324 is moved in the first direction and into the gap 340, the housing 314 and the attachment 306 may move in the second direction and be separated from the slider 354, and by extension from the handle 20 and/or the end effector 22. the collet 312 may be manipulated to remove the housing 314 and the attachment 306 from the slider 354, along the axis A, when desired. Therefore, the collet 312 serves to selectively retain the housing 314 and the attachment 306 along the axis A (i.e., axially).

Figure 29:
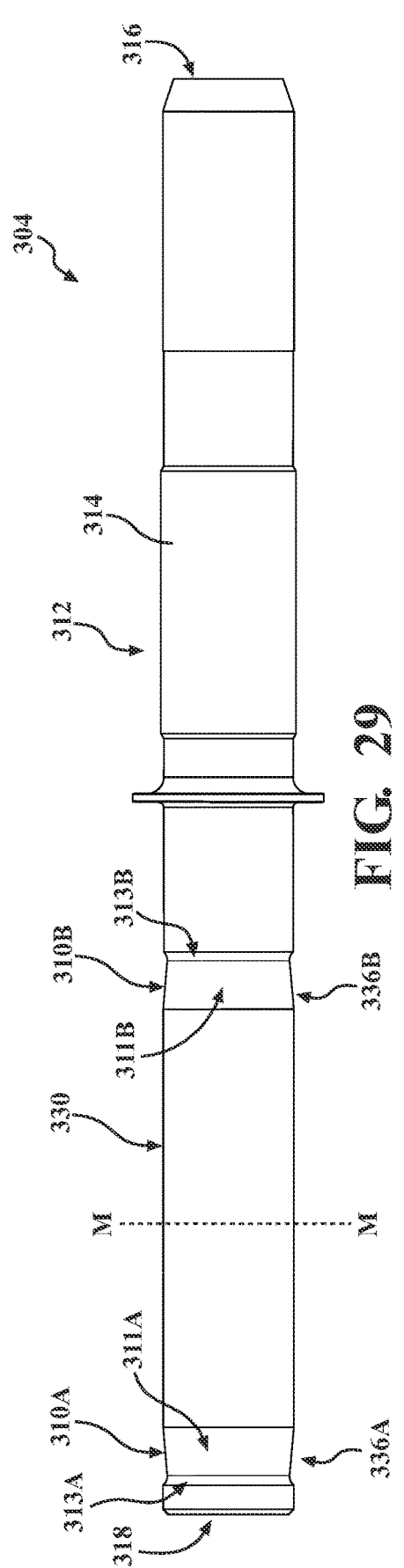
FIG. 29 is side view of an exemplary configuration of the nose tube of the interlocking collet system of FIGS. 27 and 28.
Figures 32, 33:
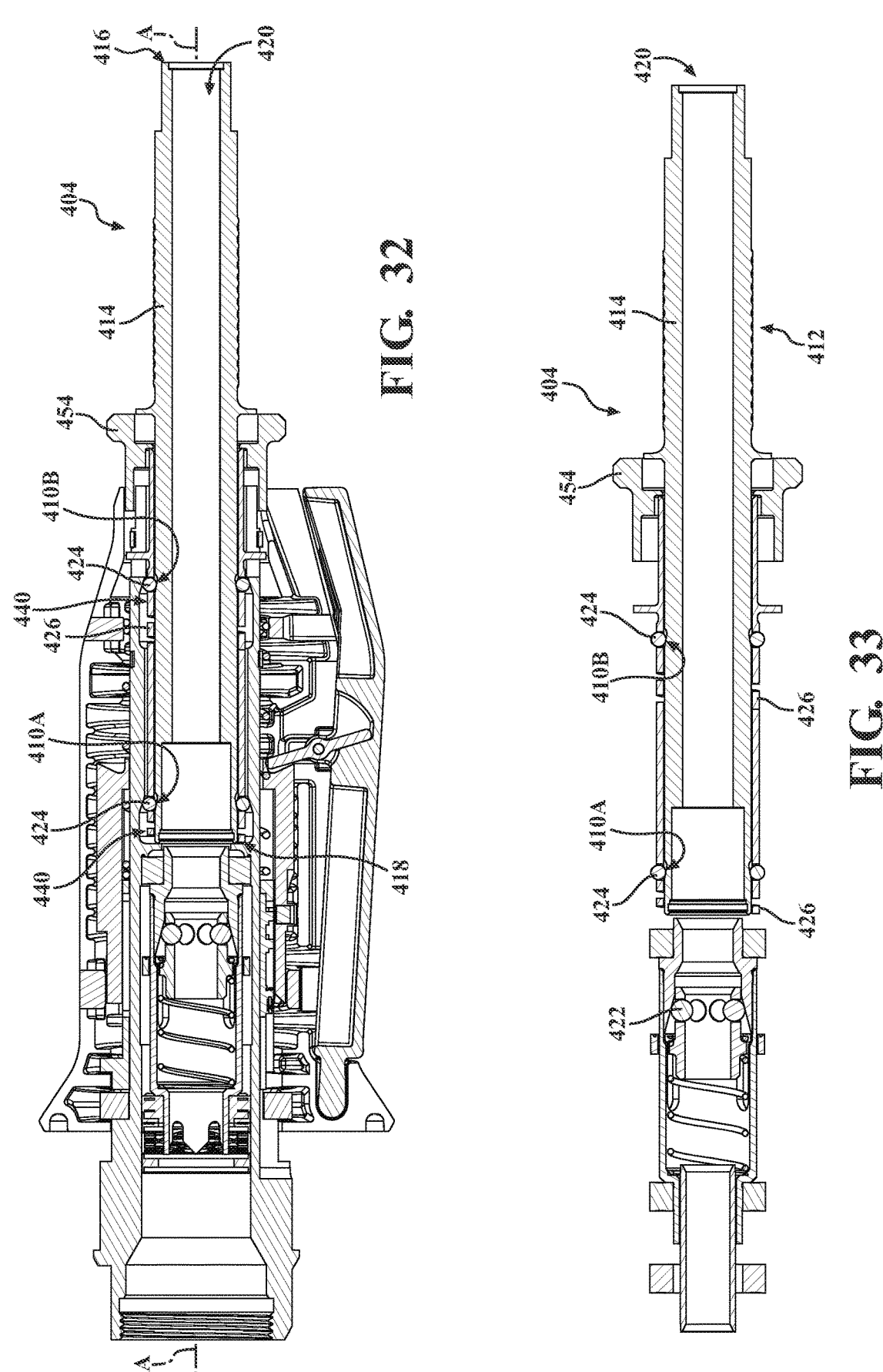
FIG. 32 is a sectional view of the end effector of FIG. 31.
FIG. 33 is a partial sectional view of the end effector of FIGS. 31 and 32, including the of the interlocking collet system and an attachment mechanism for removably securing the attachment to the end effector.
Figure 34:
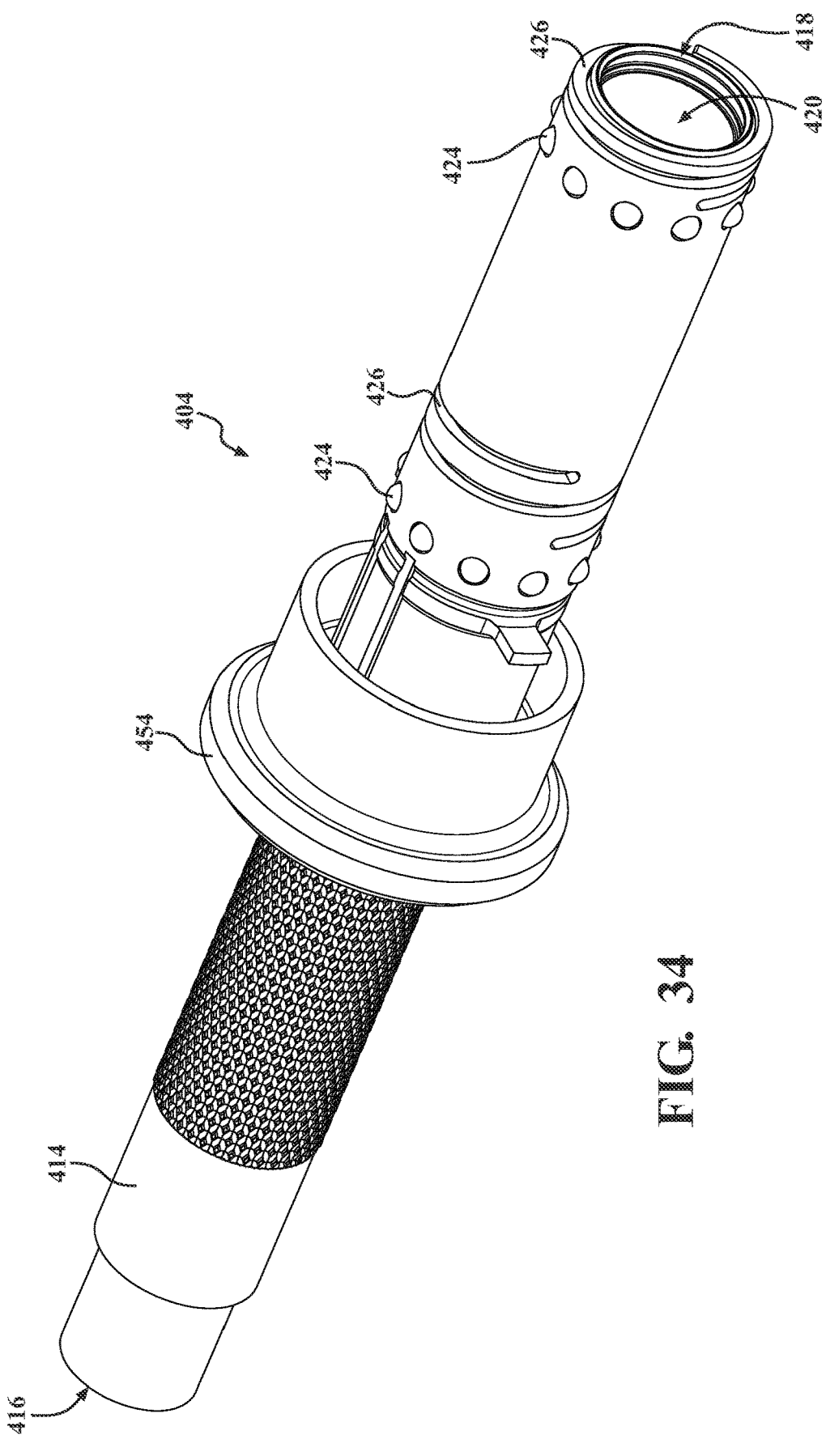
FIG. 34 is a perspective view of the interlocking collet system and attachment of the end effector of FIGS. 31-33.

Referring to FIG. 29, an exemplary configuration of the housing 324 of the collet 112 described above is illustrated. The housing 314 includes a first and second recesses 336A, 336B disposed on opposing sides a midline M. The first and second recesses 336A, 336B in the outer surface of the housing 314 define the first and second attachment surfaces 310A, 310B. Each of the first and second recesses 336A, 336B comprises a first portion 311A, 311B, and a second portion 313A, 313B. As illustrated in FIG. 29, the first portion 311A, 311B of each of the first and second recesses 336A, 336B has a first slope relative to the outer surface 330 of the housing 314. The second portion 313A, 313B of each of the first and second recesses 336A, 336B has a second slope relative to the outer surface 330 of the housing 314. The first and second recesses 336A, 336B are defined such that the first slope of the first portion 311A, 311B of the first and second recesses 336A, 336B is shallower than the second slope of the second portion 313A, 313B of the first and second recesses 336A, 336B. Furthermore, as illustrated in FIG. 29, the first portion 311A, 311B of the first and second recesses 336A, 336B is closer to the midline M than the second portion 313A, 313B of the first and second recesses 336A, 336B. This creates a mirrored profile of the first and second recesses 336A, 336B mirrored about the midline M.

In operation, when inserting the housing 314 including the mirrored profile of the first and second recesses 336A, 336B mirrored about the midline M, the slider 354 will need to be slid axially along the axis A in the direction of insertion of the housing 314 when inserting the housing 314 into the slider 354 to move the locking member(s) 324 along the axis A away from the attachment surface 310 of the housing 314 and into a gap 340 between unlock surface of the slider 354 and the housing 314. This will allow the housing 314 to be inserted into bore defined by the slider 354. Once the housing 314 is property positioned within the slider 354, the slider may be released, allowing the biasing member 326 to move the slider axially along axis A in the direction of removal. This will move the locking member(s) 324 along the axis A toward the attachment surface(s) 310A, 310B of the housing 314, seating the locking member(s) 324 in the respective first and second recesses 336A, 336B defining the attachment surface(s) 310A, 310B and securing the housing 314 to the slider 354, and by extension retaining the attachment 306 to the end effector 20. To remove the housing 314, the slider 354 may similarly be slid axially along the axis A in the direction of insertion to move the locking member(s) 324 along the axis A away from the attachment surface 310 of the housing 314 and into a gap 340 between unlock surface of the slider 354 and the housing 314. This will disengage the locking member(s) 324 from the attachment surface(s) 310 of the housing 314 allow the housing 314 to be removed. Once the housing 314 is removed from the slider 354, the slider 354 may be released, allowing the biasing member 326 to move the slider axially along axis A in the direction of removal.

Figure 27:
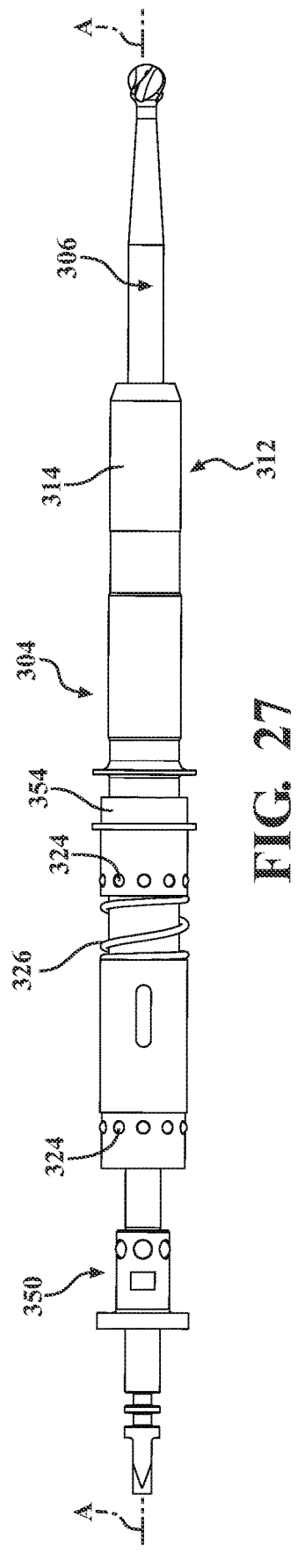
FIG. 27 is a side view of the interlocking collet system and attachment of the end effector of FIGS. 25 and 26.
Figure 28:
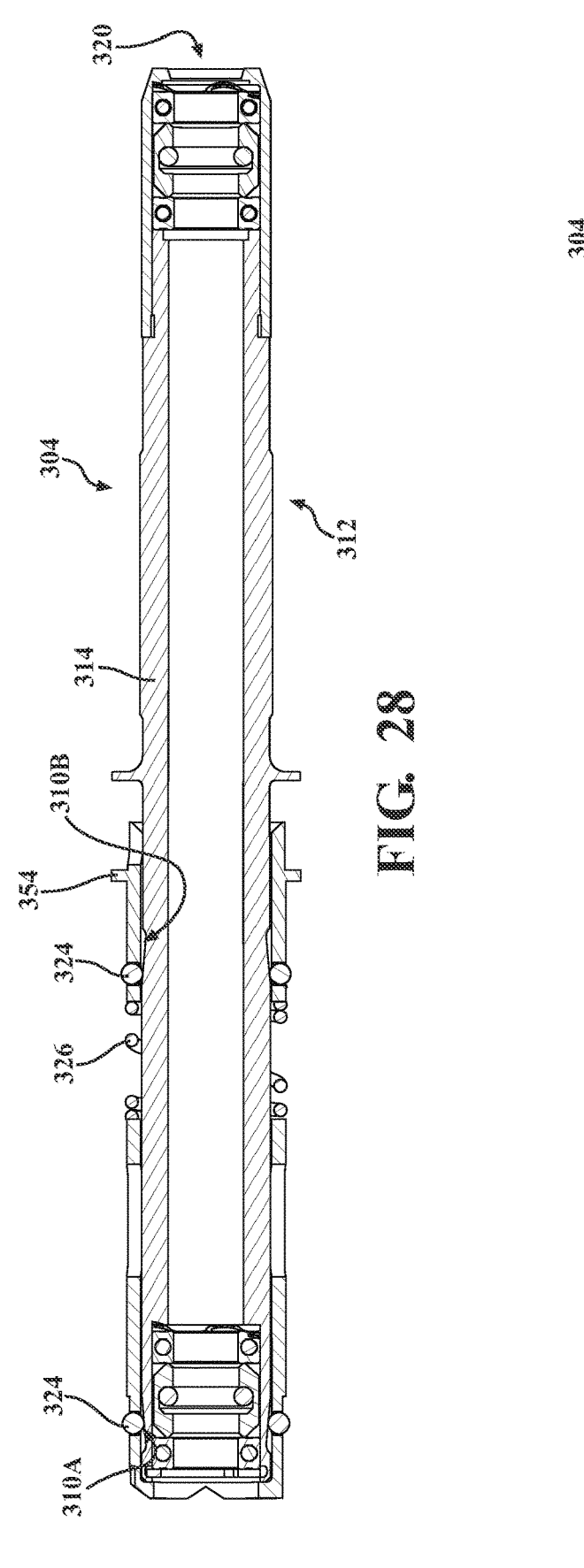
FIG. 28 is a sectional view of the interlocking collet system and attachment of the end effector of FIGS. 25-27.

As described above, the housing 314 may define a bore 320 for receiving the attachment 306. The bore 320 may be a through bore that allows the attachment 306 to extend completely through the housing and be coupled directly to the surgical tool 20 and/or end effector 22. Referring to FIGS. 27 and 30, an exemplary configuration of an arrangement for securing the attachment 306 to the end effector is illustrated. Similar to the collet 112 and attachment 106 coupling features described above, attachment 306 may comprise an attachment surface 308. The attachment surface 308 defines a first recess 334 configured to receive a locking member 322 of the end effector 22. As described above, the locking member 322 may be manipulated to be seated in the attachment surface of the attachment 306 when coupled to the end effector 22. The exemplary configuration of the attachment surface illustrated in FIG. 30, in combination with the exemplary locking member 322 illustrated in FIG. 27 may be configured to allow the attachment 306 to be rotated by the end effector 22 while securing the position of the attachment 306 axially along the axis A. Alternatively, the attachment 306 and the locking member 322 may be configured similar to the configurations described and illustrated in FIGS. 19 to 23, which may also rotate the attachment 306 while securing it axially to the end effector 22.

IV. Alternative Configuration of Interlocking Collet System

Referring to the Figures, wherein like numerals indicate like or corresponding parts throughout the several views, an interlocking collet system 104, 304 is generally shown in FIGS. 31-36. While not illustrated in the Figures, the interlocking collet system 404 may be utilized with the system 10, and more specifically, for retaining the surgical tool 22 to the end effector 20. However, the interlocking collet system 404 may be utilized for other types of surgical components other than the surgical tool 22 and end effector 20.

As shown in FIGS. 31-36, the collet 412 comprises a housing 414 configured to extend along an axis A between first and second ends 416, 418. The housing 414 defines a bore 420 along the axis A for selectively disposing and retaining an attachment 106, 306 (not shown). The collet 412 further comprises locking members 424 disposed within the bore 120 of the housing 414 and each being moveable along the axis A.

The collet 412 further comprises at least one bias member 426 disposed within the bore 420 of the housing 414. The least one bias member 426 is arranged to position the locking member(s) 424 along the axis A in a first position F in which the first locking member 424 is configured to contact the first attachment surface 408 of the attachment 406, as shown in FIGS. 26 and 30. Moreover, the at least one bias member 426 is arranged to position the locking member 424 along the axis A in a second position S in which the locking member 424 is configured to contact the attachment surface(s) 410 of the attachment 406. The locking members 424 in the first and second positions F, S, respectively, are configured to exert opposing axial forces on the housing 414 of the collet 412.

The opposing axial forces, exerted on the housing 414 by the locking members 424, act along the axis A. As such, movement of the housing 414 in one direction along the axis A causes one of the locking members 424 to exert axial forces on the housing 414 resisting removal of the housing 414 when the locking members 424 are in contact with the housing 414.

Devices using a single locking mechanism are susceptible to producing a bending moment on an attachment when a lateral load (i.e., transverse to the longitudinal axis of the attachment) is exerted on the attachment. The utilization of the multiple arrangements of locking members 424, as described herein, provides the benefit of resisting bending moments on the housing 414 when a lateral load is exerted on the housing 414. The locking members 424 distribute the load along the housing 414, rather than exerting the load on a single point (as is the case with collets with single locking mechanisms). By distributing the load, the deflection of the housing 414, and/or an attachment 106, 306 if instilled, along the axis A is reduced. In some examples, the housing 414 is rotated about the axis A (e.g., when incorporated with the attachment 106, 306, as described above). Deflection of the housing 314 can cause sudden, unintended, changes in the angular velocity of an attached attachment 106, 306 (i.e., slip). When used with the end effector 22, uniform angular velocity provides benefits, such as, efficient and uniform removal of material (i.e., when the attachment 106, 306 is configured as the tool 20) and cooler cutting temperatures.

The collet 412 may further comprise a slide 454 configured to receive the housing 414 and being movable along the axis A. The slide 454 is configured to engage and move the locking members 424 along the axis A against the bias of the bias member 426. More specifically, the slide 454 is configured to engage and move the locking member(s) 424 along the axis A away from the attachment surface 410 and into a gap 440 between unlock surface of the slider 454 and the housing 414 (i.e., remove the locking member 424 from contact with the attachment surface 410A of the housing 414). Likewise, the slide 454 is configured to engage and move the locking member 424 along the axis A away from the attachment surface 410B and into the gap 440 between the unlock surface and the attachment surface 410 (i.e., remove the locking member 424 from contact with the attachment surface 410B of the housing 414). As mentioned above, moving either of the locking members 424 into the gap 440 will facilitate movement of the housing 414 along the axis A and disassembly of the housing 414 and/or an included attachment 106, 306 from the slider 454 of the collet 412. More specifically, when the locking member 424 is moved in the first direction and into the gap 440, the housing 414 and the included attachment 106, 306 may move in the second direction and be separated from the slider 454, and by extension from the handle 20 and/or the end effector 22. The collet 412 may be manipulated to remove the housing 414 and the included attachment 106, 306 from the slider 454, along the axis A, when desired. Therefore, the collet 412 serves to selectively retain the housing 414 and the optionally included attachment 106, 306 along the axis A (i.e., axially).

Figures 35, 36:
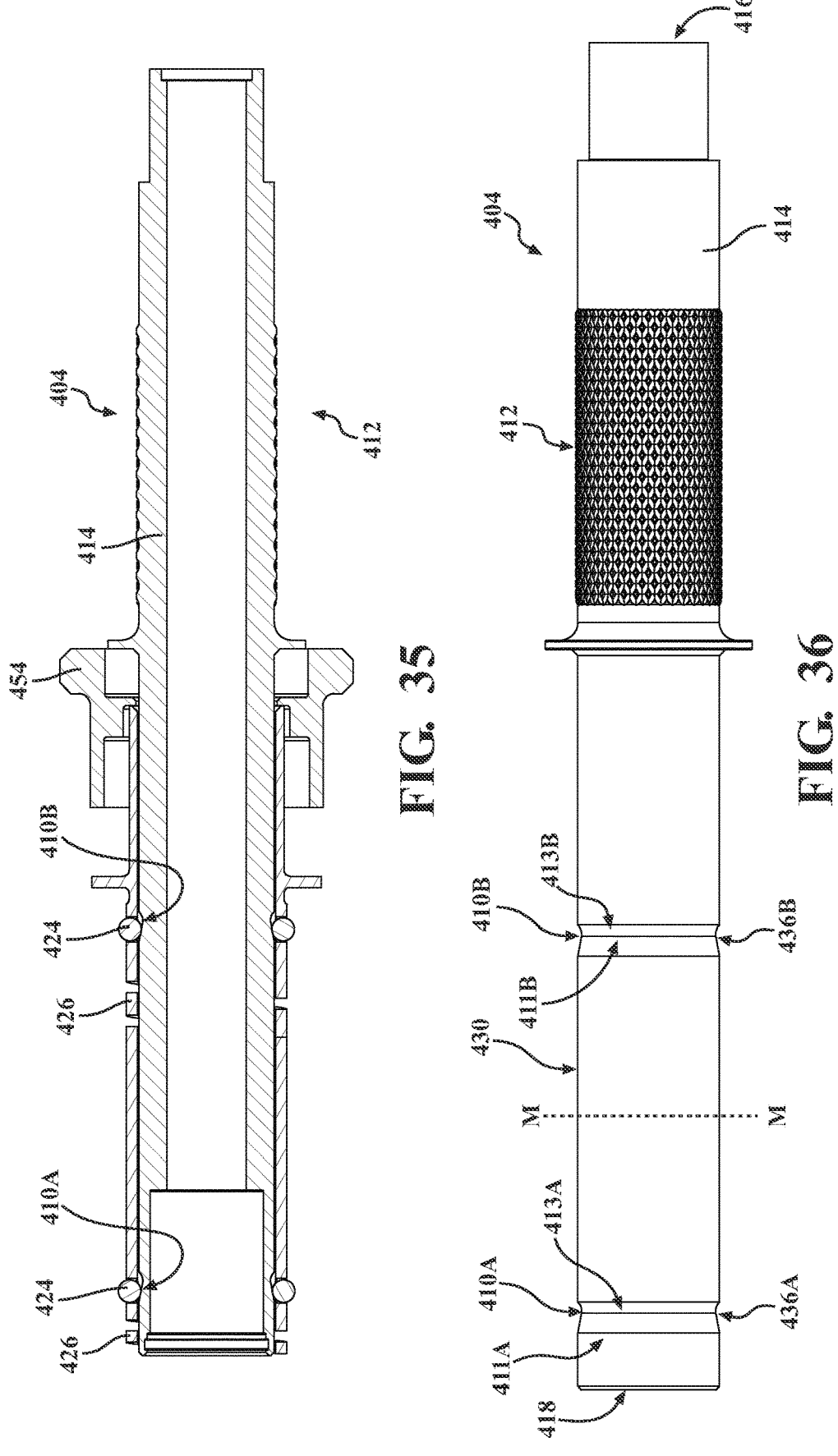
FIG. 35 is a sectional view of the interlocking collet system and attachment of the end effector of FIGS. 31-34
FIG. 36 is a side view of an exemplary configuration of the nose tube of the interlocking collet system of FIGS. 27 and 28.

Referring to FIG. 36, an alternative exemplary configuration of the housing 424 of the collet 112, 312 described above is illustrated. The housing 414 includes a first and second recesses 436A, 436B disposed on opposing sides a midline M. The first and second recesses 436A, 436B in the outer surface of the housing 414 define the first and second attachment surfaces 410A, 410B. Each of the first and second recesses 436A, 436B comprises a first portion 411A, 411B, and a second portion 413A, 413B. As illustrated in FIG. 36, the first portion 411A, 411B of each of the first and second recesses 436A, 436B has a first slope relative to the outer surface 430 of the housing 414. The second portion 413A, 413B of each of the first and second recesses 436A, 436B has a second slope relative to the outer surface 430 of the housing 414. The first and second recesses 436A, 436B are defined such that the first slope of the first portion 411A, 411B of the first and second recesses 436A, 436B is shallower than the second slope of the second portion 413A, 413B of the first and second recesses 436A, 436B. Furthermore, as illustrated in FIG. 36, the first portion 411A, 411B of the respective first and second recesses 436A, 436B are closer to the second end 418 of the housing 414 than the second portion 413A, 413B of the respective first and second recesses 436A, 436B, which are closer to the first end 416 of the housing 414. This results in the first and second recesses 436A, 436B having the same the profile on both sides of the midline M.

In operation, when inserting the housing 414 including the first and second recesses 436A, 436B with the same profile, it is not necessary to manipulate the slider 454 axially along the axis A in the direction to insert the housing 414. The profile of the first and second recesses 436A, 436B of the attachment surfaces 410A, 410B allows the housing 414 to be inserted into the bore of the slider 454 with needing to maneuver the slider 454 and/or the locking member(s) 424. The profile and arrangement of the attachment surfaces 410A, 410B is such that the locking member(s) 424 will not inhibit insertion, and once the housing 414 is properly positioned within the slider 454, the locking member(s) 424 will naturally and automatically seat within the attachment surfaces 410A, 410B and prevent removal of the housing 414 and/or the included attachment 106, 306 from the end effector 20 without manipulation of the slider 454. The process to remove and/or separate the housing 414 from the slider 454 is similar to the processes described above. To remove the housing 414, the slider 454 may similarly be slid axially along the axis A in the direction of insertion to move the locking member(s) 424 along the axis A away from the attachment surface 410 of the housing 414 and into a gap 440 between unlock surface of the slider 454 and the housing 414. This will disengage the locking member(s) 424 from the attachment surface(s) 410 of the housing 414 allow the housing 414 to be removed. Once the housing 414 is removed from the slider 454, the slider 454 may be released, allowing the biasing member 426 to move the slider axially along axis A in the direction of removal.

Clauses directed to additional configurations of the invention.

I. An interlocking collet system comprising:

an attachment comprising first and second attachment surfaces spaced from one another; and a collet for selectively retaining the attachment, the collet comprising:

a housing configured to extend along an axis between first and second ends and defining a bore along the axis for selectively disposing and retaining the attachment therein in an installed position;

first and second locking members disposed within the bore of the housing and each being moveable along the axis; and at least one bias member disposed within the bore of the housing, with the at least one bias member arranged to position the first locking member along the axis in a first position in which the first locking member is configured to contact the first attachment surface of the attachment and with the at least one bias member arranged to position the second locking member along the axis in a second position in which the second locking member is configured to contact the second attachment surface of the attachment, and wherein the first and second locking members in the first and second positions, respectively, are configured to exert opposing axial forces on the attachment.

II. The interlocking collet system as set forth in any one of the preceding clauses, wherein at least one of the first and second attachment surfaces are skewed relative to the axis to facilitate the opposing axial forces on the attachment.

III. The interlocking collet system of any one of the preceding clauses, wherein the at least one bias member has a stiffness that is configured to exert the opposing axial forces on the attachment through the first and second locking members to retain the attachment in the installed position.

IV. The interlocking collet system of clause III, wherein the stiffness of the at least one bias member maintains the first locking member in the first position and the second locking member in the second position to prevent removal of the attachment from the bore.

V. The interlocking collet system of any one of the preceding clause 1, wherein the housing comprises first and second housing surfaces spaced from one another and disposed at least partially within the bore, with the first locking member configured to contact both of the first attachment surface and the first housing surface in the first position and the second locking member configured to contact both of the second attachment surface and the second housing surface in the second position.

VI. The interlocking collet system of clause V, wherein the first housing surface is proximate to the first end of the housing and the second housing surface is proximate to the second end of the housing.

VII. The interlocking collet system of clause VI, wherein at least one of the first housing surface and the first attachment surface is skewed relative to the axis and at least one of the second housing surface and the second attachment surface is skewed relative to the axis to facilitate the opposing axial forces on the attachment.

VIII. The interlocking collet system of clause VII, wherein the first housing surface and the first attachment surface define a first orthogonal distance therebetween perpendicular to the axis and the second housing surface and the second attachment surface define a second orthogonal distance therebetween perpendicular to the axis, with the skewed configuration of at least one of the first housing surface and the first attachment surface configured to facilitate a reduction in the first orthogonal distance when the attachment moves from the installed position in a first direction along the axis and wedges the first locking member between the housing and the attachment to prevent removal of the attachment from the bore in the first direction, and with the skewed configuration of at least one of the second housing surface and the second attachment surface configured to facilitate a reduction in the second orthogonal distance when the attachment moves from the installed position in a second direction along the axis, opposite the first direction, and wedges the second locking member between the housing and the attachment to prevent removal of the attachment from the bore in the second direction.

IX. The interlocking collet system of clause VIII, wherein the first housing surface and the first attachment surface define a first axial distance therebetween parallel to the axis, with the skewed configuration of both of the first housing surface and the first attachment surface configured to facilitate a reduction in the first axial distance when the attachment moves from the installed position in the first direction along the axis and wedges the first locking member between the housing and the attachment to prevent removal of the attachment from the bore in the first direction.

X. The interlocking collet system of clause VIII, wherein the second housing surface and the second attachment surface define a second axial distance therebetween parallel to the axis, with the skewed configuration of both of the second housing surface and the second attachment surface configured to facilitate a reduction in the second axial distance when the attachment moves from the installed position in the second direction along the axis and wedges the second locking member between the housing and the attachment to prevent removal of the attachment from the bore in the second direction.

XI. The interlocking collet system of clause V, wherein the attachment comprises at least one attachment unlock surface adjacent the first and second attachment surfaces and the housing comprises at least one housing unlock surface adjacent the first and second housing surfaces, with the attachment and housing unlock surfaces concentrically spaced from one another and configured to dispose the first and second locking members therebetween to facilitate movement of the attachment, independent of the housing, along the axis.

XII. The interlocking collet system of clause XI, wherein the at least one attachment unlock surface is disposed between the first and second attachment surfaces and the at least one housing unlock surface is disposed between the first and second housing surfaces.

XIII The interlocking collet system of clause II, wherein the first and second attachment surfaces face opposing directions along the axis, with the first locking member disposed along the axis between the first attachment surface and one of the first and second ends of the housing, and with the second locking member configured to be disposed along the axis between the second attachment surface and the other one of the first and second ends of the housing.

XIV. The interlocking collet system of clause XIII, wherein the first and second attachment surfaces are symmetric about a plane orthogonal to the axis.

XV. The interlocking collet system of clause II, wherein the first attachment surface extends inwardly toward the axis such that the first attachment surface defines a first recess configured to receive the first locking member therein.

XVI. The interlocking collet system of clause II, wherein the second attachment surface extends outwardly away from the axis.

XVII. The interlocking collet system of clause II, wherein the second attachment surface extends inwardly toward the axis such that the second attachment surface defines a second recess configured to receive the second locking member therein.

XVIII. The interlocking collet system of any one of the preceding clauses, wherein each of the first and second locking members comprise a frame and a plurality of spheres retained by the frame and radially disposed around the axis, with each of the spheres being movable, relative to the frame, transverse to the axis.

XIX. The interlocking collet system of any one of the preceding clauses, wherein the at least one bias member is further defined as at least one compression spring.

XX. The interlocking collet system of any one of the preceding clauses, wherein the at least one bias member is a single bias member disposed between the first and second locking members and configured to bias the locking members away from one another.

XXI. The interlocking collet system of any one of the preceding clauses, further comprising a slide disposed along the housing and movable along the axis, with the slide configured to engage and move the first and second locking members along the axis against the bias of the at least one bias member.

XXII. The interlocking collet system of clause XXI, wherein the housing defines at least one slot extending longitudinally along the axis and opening into the bore and an exterior of the housing, with each of the first and second locking members comprising a projection extending through the at least one slot and disposed in the exterior, and with the slide configured to engage the projections to move the first and second locking members along the axis against the bias of the bias member.

XXIII. The interlocking collet system of clause XXII, wherein the at least one bias member biases the first and second locking members away from one another, with the slide defining first and second abutment surfaces spaced from and facing one another along the axis and with the projections of the first and second locking members disposed between the abutment surfaces, with the first abutment surface configured to engage and move the projection of the first locking member when the slide moves in one direction along the axis and with the second abutment surface configured to engage and move the projection of the second locking member when the slide moves in another direction along the axis.

XXIV. The interlocking collet system of clause II, wherein at least one of the first and second attachment surfaces extend outwardly away from the axis.

XXV. The interlocking collet system of clause XXIV, wherein the first and second locking member, that respectively correspond with the outwardly extending first and second attachment surface, have an annular configuration around the axis and define an inner diameter, with the outwardly extending first and second attachment surfaces having an outer diameter that increases as the surfaces extend further from the axis such that first and second locking member moves up the first and/or second attachment surface until the inner and outer diameters equal one another.

XXVI. The interlocking collet system of clause XXV, wherein the outwardly extending first and second attachment surface encircles the attachment around the axis.

XXVII. The interlocking collet system of any preceding clause, further comprising a first surgical component and a second surgical component, wherein the collet is coupled to the first surgical component and the attachment is coupled to the second surgical component.

XXVIII. The interlocking collet system of clause XXVII, wherein the first surgical component is any one of a surgical navigation tracker, a surgical guide component, a powered surgical instrument component, a surgical hand tool component, a surgical robot component, a passive arm component, a surgical table component, and an imaging device component, and the second surgical component is any one of a surgical navigation tracker, a surgical guide component, a powered surgical instrument component, a surgical hand tool component, a surgical robot component, a passive arm component, a surgical table component, and an imaging device component.

XXIX. The collet of any one of the preceding clauses.

XXX. The attachment of any one of clauses I-XXVIII.

XXXI. An end effector comprising the interlocking collet system of any one of clauses I-XXVIII, wherein the housing of the collet is further defined as a nose tube and the attachment is further defined as a surgical tool.

XXXII. A robotic system comprising:
an end effector comprising a nose tube and being configured to receive a surgical tool;
a plurality of links and joints being configured to support the end effector; and
the interlocking collet system of any one of clauses I-XXVIII, wherein the housing of the collet is further defined as the nose tube and the attachment is further defined as the surgical tool.

XXXIII. An interlocking collet system comprising:
a housing configured to extend along an axis between first and second ends and an outer surface defining a first attachment surface and a second attachment surface;
a slider defining a second bore for receiving the
first and second locking members disposed within the bore of the slider and each being moveable along the axis; and
at least one bias member disposed within the bore of the housing, with the at least one bias member arranged to position the first locking member along the axis in a first position in which the first locking member is configured to contact the first attachment surface of the housing and with the at least one bias member arranged to position the second locking member along the axis in a second position in which the second locking member is configured to contact the second attachment surface of the housing, and wherein the first and second locking members in the first and second positions, respectively, are configured to exert opposing axial forces on the housing.

XXXIV. An interlocking collet system comprising:
a housing configured to extend along an axis between first and second ends and an outer surface defining a first attachment surface and a second attachment surface;
a slider defining a second bore for receiving the
first and second locking members disposed within the bore of the slider and each being moveable along the axis; and wherein the first attachment surface and the second attachment surface each comprise a first portion and a second portion defining a recess in the outer surface of the housing;

wherein the first portion of the first attachment surface and the second attachment surface is oriented at a first slope relative to the outer surface, and the second portion of the first attachment surface and the second attachment surface is oriented at a second slope relative to the outer surface.

XXXV. The interlocking collet system of clause XXXIV, wherein the first portion of each of the first attachment surface and the second attachment surface is positioned closer to the second end of the housing than the second portion of each of the respective first and second attachment surfaces.

XXXVI. The interlocking collet system of clause XXXIV, wherein the first portion of the first attachment surface is positioned closer to the second end of the housing than the second portion of first attachment surface; and wherein the first portion of the second attachment surface is positioned closer to the first end of the housing than the second portion of second attachment surface.

XXXVII. The interlocking collet system of clause XXXIV, wherein the first attachment surface and the second attachment surface are mirror about a midline oriented perpendicular to the axis and positioned axially along the axis to be spaced equidistant between the first attachment surface and the second attachment surface;

wherein the first and second portions of each of the first attachment surface and the second attachment surface are arrange such that the first attachment surface and the second attachment surface are mirrored about the midline.

XXXVIII. The interlocking collet system of any one of clauses XXXIV to XXXVII, wherein the first slope is shallower relative to the outer surface than the second slope is relative to the outer surface.

XXXIX. The interlocking collet system of any one of clauses XXXIV to XXXVII, wherein the second slope is steeper relative to the outer surface than the first slope is relative to the outer surface.

XL. The interlocking collet system of any one of clauses XXXIV to XXXIX, further comprising at least one bias member disposed within the bore of the slider, with the at least one bias member arranged to position the first locking member along the axis in a first position in which the first locking member is configured to contact the first attachment surface of the housing and with the at least one bias member arranged to position the second locking member along the axis in a second position in which the second locking member is configured to contact the second attachment surface of the housing, and wherein the first and second locking members in the first and second positions, respectively, are configured to exert opposing axial forces on the housing.

XLI. The interlocking collet system of any one of clauses XXXIV to XL, wherein the housing is configured to removably receive an attachment.

XLII. An end effector comprising the interlocking collet system of any one of clauses XXXIV to XLI, wherein the housing of the collet is further defined as a nose tube and the attachment is further defined as a surgical tool.

XLIII. An interlocking collet system comprising:

a housing configured to extend along an axis between first and second ends and an outer surface defining a first attachment surface and a second attachment surface;

a slider defining a second bore for receiving the first and second locking members disposed within the bore of the slider and each being moveable along the axis; and wherein the first attachment surface and the second attachment surface each comprise a first portion and a second portion defining a recess in the outer surface of the housing;

wherein the first portion of the first attachment surface is positioned closer to the second end of the housing than the second portion of first attachment surface; and wherein the first portion of the second attachment surface is positioned closer to the first end of the housing than the second portion of second attachment surface.

XLIV. The interlocking collet system of clause XLIII, wherein the first portion of the first attachment surface and the second attachment surface is oriented at a first slope relative to the outer surface, and the second portion of the first attachment surface and the second attachment surface is oriented at a second slope relative to the outer surface.

XLV. An interlocking collet system comprising:

a housing configured to extend along an axis between first and second ends and an outer surface defining a first attachment surface and a second attachment surface;

a slider defining a second bore for receiving the first and second locking members disposed within the bore of the slider and each being moveable along the axis; and wherein the first attachment surface and the second attachment surface each comprise a first portion and a second portion defining a recess in the outer surface of the housing;

wherein the first portion of the first attachment surface is positioned closer to the second end of the housing than the second portion of first attachment surface; and wherein the first portion of the second attachment surface is positioned closer to the first end of the housing than the second portion of second attachment surface.

Several examples have been described in the foregoing description. However, the examples discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described. Furthermore, components described in the various configurations including the same name and/or base reference number varying by factors of 100, 200, 300, and 400 are assumed to have any all features, characteristics, and/or functionality components described earlier that share the same base number.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An interlocking collet system of a robotic surgical system, the collet system comprising:

a surgical tool comprising first and second attachment surfaces spaced from one another; and a collet for selectively coupling the surgical tool to an end effector, the collet comprising:

a housing configured to extend along an axis between first and second ends and defining a bore along the axis for selectively disposing and retaining the surgical tool therein in an installed position;

first and second locking members disposed within the bore of the housing and each being moveable along the axis within the housing; and at least one bias member disposed within the bore of the housing, with the at least one bias member arranged to position the first locking member along the axis in a first position relative to the housing in which the first locking member is configured to contact the first attachment surface of the surgical tool and with the at least one bias member arranged to position the second locking member along the axis in a second position relative to the housing in which the second locking member is configured to contact the second attachment surface of the surgical tool, and wherein the first and second locking members in the first and second positions, respectively, are configured to exert opposing axial forces on the surgical tool; and wherein in response to the collet selectively retaining the surgical tool, the first and second attachment surfaces of the surgical tool are symmetrically oriented relative to each other with respect to a plane that is orthogonal to the axis.

2. The interlocking collet system of claim 1, wherein the first and second attachment surfaces are skewed to face opposing directions along the axis or skewed to face toward one another relative to the axis to facilitate the opposing axial forces on the surgical tool to retain the surgical tool.

3. The interlocking collet system of claim 2, wherein each of the first and second locking members comprises a sphere, the sphere configured to move along the skewed first and second attachment surfaces of the surgical tool and/or first and second housing surfaces of the housing as the first and second locking members move along the axis.

4. The interlocking collet system of claim 1, wherein the at least one bias member has a stiffness that is configured to exert the opposing axial forces on the surgical tool through the first and second locking members to retain the surgical tool in the installed position.

5. The interlocking collet system of claim 4, wherein the stiffness of the at least one bias member maintains the first locking member in the first position and the second locking member in the second position to prevent removal of the surgical tool from the bore.

6. The interlocking collet system of claim 1, wherein the housing comprises first and second housing surfaces spaced from one another and disposed at least partially within the bore, with the first locking member configured to contact both of the first attachment surface and the first housing surface in the first position and the second locking member configured to contact both of the second attachment surface and the second housing surface in the second position.

7. The interlocking collet system of claim 6, wherein the first housing surface is proximate to the first end of the housing and the second housing surface is proximate to the second end of the housing.

8. The interlocking collet system of claim 7, wherein the first housing surface and the first attachment surface define a first orthogonal distance therebetween perpendicular to the axis and the second housing surface and the second attachment surface define a second orthogonal distance therebetween perpendicular to the axis, with a first skewed configuration of at least one of the first housing surface and the first attachment surface configured to facilitate a reduction in the first orthogonal distance when the surgical tool moves from the installed position in a first direction along the axis and wedges the first locking member between the housing and the surgical tool to prevent removal of the surgical tool from the bore in the first direction, and with a second skewed configuration of at least one of the second housing surface and the second attachment surface configured to facilitate a reduction in the second orthogonal distance when the surgical tool moves from the installed position in a second direction along the axis, opposite the first direction, and wedges the second locking member between the housing and the surgical tool to prevent removal of the surgical tool from the bore in the second direction.

9. The interlocking collet system of claim 8, wherein the first housing surface and the first attachment surface define a first axial distance therebetween parallel to the axis, with the first skewed configuration of both of the first housing surface and the first attachment surface configured to facilitate a reduction in the first axial distance when the surgical tool moves from the installed position in the first direction along the axis and wedges the first locking member between the housing and the surgical tool to prevent removal of the surgical tool from the bore in the first direction.

10. The interlocking collet system of claim 8, wherein the second housing surface and the second attachment surface define a second axial distance therebetween parallel to the axis, with the second skewed configuration of both of the second housing surface and the second attachment surface configured to facilitate a reduction in the second axial distance when the surgical tool moves from the installed position in the second direction along the axis and wedges the second locking member between the housing and the surgical tool to prevent removal of the surgical tool from the bore in the second direction.

11. The interlocking collet system of claim 6, wherein the surgical tool comprises at least one attachment unlock surface adjacent the first and second attachment surfaces and the housing comprises at least one housing unlock surface adjacent the first and second housing surfaces, with the at least one attachment unlock surface and the at least one housing unlock surface concentrically spaced from one another and configured to dispose the first and second locking members therebetween to facilitate movement of the surgical tool, independent of the housing, along the axis.

12. The interlocking collet system of claim 11, wherein the at least one attachment unlock surface is disposed between the first and second attachment surfaces and the at least one housing unlock surface is disposed between the first and second housing surfaces.

13. The interlocking collet system of claim 1, wherein the first and second attachment surfaces face opposing directions along the axis, with the first locking member disposed along the axis between the first attachment surface and one of the first and second ends of the housing, and with the second locking member configured to be disposed along the axis between the second attachment surface and the other one of the first and second ends of the housing.

14. The interlocking collet system of claim 1, wherein the first attachment surface extends inwardly toward the axis such that the first attachment surface defines a first recess configured to receive the first locking member therein.

15. The interlocking collet system of claim 14, wherein the second attachment surface extends inwardly toward the axis such that the second attachment surface defines a second recess configured to receive the second locking member therein.

16. The interlocking collet system of claim 1, wherein the at least one bias member is a single bias member disposed between the first and second locking members and configured to bias the locking members away from one another.

17. The interlocking collet system of claim 1, further comprising a slide disposed along the housing and movable along the axis, with the slide configured to engage and move the first and second locking members along the axis against the bias of the at least one bias member.

18. The interlocking collet system of claim 17, wherein the housing defines at least one slot extending longitudinally along the axis and opening into the bore and an exterior of the housing, with each of the first and second locking members comprising a projection extending through the at least one slot and disposed in the exterior, and with the slide configured to engage the projections to move the first and second locking members along the axis against the bias of the at least one bias member.

19. The interlocking collet system of claim 18, wherein the at least one bias member biases the first and second locking members away from one another, with the slide defining first and second abutment surfaces spaced from and facing one another along the axis and with the projections of the first and second locking members disposed between the abutment surfaces, with the first abutment surface configured to engage and move the projection of the first locking member when the slide moves in one direction along the axis and with the second abutment surface configured to engage and move the projection of the second locking member when the slide moves in another direction along the axis.

20. The interlocking collet system of claim 17, wherein the slide is further configured to move the first and second locking members in a first direction and an opposed second direction along the axis against the bias of the at least one bias member such that:

when the second locking member is moved in the first direction, the surgical tool may move in the second direction; and when the first locking member is moved in the second direction, the surgical tool may move in the first direction to provide bidirectional disassembly of the surgical tool from the collet.

21. The interlocking collet system of claim 17, wherein the slide at least partially encircles an outer surface of the housing.

22. The interlocking collet system of claim 1, wherein the first and second locking members, that respectively correspond with at least one of the first and second attachment surfaces that extend outwardly away from the axis, have an annular configuration around the axis and define an inner diameter, with the at least one of the first and second attachment surfaces that extend outwardly away from the axis having an outer diameter that increases as the at least one of the first and second attachment surfaces extend outwardly further from the axis such that first and second locking members move up the at least one of the first and second attachment surfaces until the inner and outer diameters equal one another.

23. The interlocking collet system of claim 1, further comprising a first surgical component and a second surgical component, wherein the collet is coupled to the first surgical component and the surgical tool is coupled to the second surgical component; and wherein the first surgical component is any one of a surgical navigation tracker, a surgical guide component, a powered surgical instrument component, a surgical hand tool component, a surgical robot component, a passive arm component, a surgical table component, and an imaging device component, and the second surgical component is any one of a surgical navigation tracker, a surgical guide component, a powered surgical instrument component, a surgical hand tool component, a surgical robot component, a passive arm component, a surgical table component, and an imaging device component.

24. An interlocking collet system comprising:

an attachment comprising first and second attachment surfaces spaced from one another; and a collet for selectively retaining the attachment, the collet comprising:

a housing configured to extend along an axis between first and second ends and defining a bore along the axis for selectively disposing and retaining the attachment therein in an installed position;

first and second locking members disposed within the bore of the housing and each being moveable along the axis within the housing; and at least one bias member disposed within the bore of the housing, with the at least one bias member arranged to position the first locking member along the axis in a first position relative to the housing in which the first locking member is configured to contact the first attachment surface of the attachment and with the at least one bias member arranged to position the second locking member along the axis in a second position relative to the housing in which the second locking member is configured to contact the second attachment surface of the attachment, and wherein the first and second locking members in the first and second positions, respectively, are configured to exert opposing axial forces on the attachment; and wherein the first and second attachment surfaces are skewed such that the first locking member exerts a force on the first attachment surface that is at least partially directed toward the second locking member and the second locking member simultaneously exerts a force on the second attachment surface that is at least partially directed toward the first locking member.

25. An interlocking collet system comprising:

an attachment comprising first and second attachment surfaces spaced from one another and a longitudinal axis, the first and second attachment surfaces skewed relative to the longitudinal axis and exhibit mirror symmetry relative to a plane orthogonal to the longitudinal axis of the attachment; and a collet for selectively retaining the attachment, the collet comprising:

a housing configured to extend along an axis between first and second ends and defining a bore along the axis for selectively disposing and retaining the attachment therein in an installed position;

first and second locking members disposed within the bore of the housing and each being moveable along the axis within the housing; and at least one bias member disposed within the bore of the housing, with the at least one bias member arranged to position the first locking member along the axis in a first position relative to the housing in which the first locking member is configured to contact the first attachment surface of the attachment and with the at least one bias member arranged to position the second locking member along the axis in a second position relative to the housing in which the second locking member is configured to contact the second attachment surface of the attachment, and wherein the first and second locking members in the first and second positions, respectively, are configured to simultaneously exert opposing axial forces on the first and second attachment surfaces of the attachment.

\* \* \* \* \*